(12) United States Patent
Abdel-Magid et al.

(10) Patent No.: US 11,661,429 B2
(45) Date of Patent: May 30, 2023

(54) TOPICAL PHOSPHOINOSITIDE 3-KINASE INHIBITORS

(71) Applicant: VENTHERA, INC., Palo Alto, CA (US)

(72) Inventors: Ahmed F. Abdel-Magid, Ambler, PA (US); Agis Kydonieus, Kendall Park, NJ (US); Thomas Rossi, Portsmouth, NH (US); Hock S. Tan, North Brunswick, NJ (US)

(73) Assignee: VENTHERA, INC., Palo Alto, CA (US)

( * ) Notice: Subject to any disclaimer, the term of this patent is extended or adjusted under 35 U.S.C. 154(b) by 244 days.

(21) Appl. No.: 16/783,050

(22) Filed: Feb. 5, 2020

(65) Prior Publication Data

US 2020/0247816 A1    Aug. 6, 2020

Related U.S. Application Data

(60) Provisional application No. 62/958,049, filed on Jan. 7, 2020, provisional application No. 62/802,093, filed on Feb. 6, 2019.

(51) Int. Cl.
| | | |
|---|---|---|
| *C07D 495/04* | (2006.01) | |
| *A61K 9/00* | (2006.01) | |
| *A61K 47/38* | (2006.01) | |
| *A61K 47/12* | (2006.01) | |
| *A61K 47/34* | (2017.01) | |
| *A61K 9/06* | (2006.01) | |

(52) U.S. Cl.
CPC .......... *C07D 495/04* (2013.01); *A61K 9/0014* (2013.01); *A61K 9/06* (2013.01); *A61K 47/12* (2013.01); *A61K 47/34* (2013.01); *A61K 47/38* (2013.01)

(58) Field of Classification Search
CPC ...... C07D 495/04; A61K 9/0014; A61K 9/06; A61K 47/12; A61K 47/34; A61K 47/38
See application file for complete search history.

(56) References Cited

U.S. PATENT DOCUMENTS

| 6,838,457 B2 | 1/2005 | Hayakawa et al. |
| 8,906,909 B2 | 12/2014 | Cai et al. |
| 8,921,361 B2 | 12/2014 | Cmiljanovic et al. |
| 10,864,215 B2 | 12/2020 | Baselga et al. |
| 2004/0009798 A1 | 1/2004 | Hayakawa |
| 2013/0189274 A1 | 6/2013 | Berkenblit et al. |
| 2013/0189260 A1 | 7/2013 | Hanson et al. |
| 2013/0345232 A1 | 12/2013 | Lane et al. |
| 2018/0117055 A1 | 5/2018 | Baselga et al. |
| 2021/0060031 A1 | 3/2021 | Baselga et al. |

FOREIGN PATENT DOCUMENTS

| CN | 102268014 A | 12/2011 |
| EP | 3251657 A1 | 12/2017 |
| EP | 3563840 A1 | 11/2019 |
| WO | WO-2006046040 A1 | 5/2006 |
| WO | WO-2007021933 A2 | 2/2007 |
| WO | WO-2012051416 A1 | 4/2012 |
| WO | WO-2013015833 A2 | 1/2013 |
| WO | WO-2013182668 A1 | 12/2013 |
| WO | WO-2014046617 A1 | 3/2014 |
| WO | WO-2016187157 A1 | 11/2016 |
| WO | WO-2017140828 A1 | 8/2017 |
| WO | WO-2020163525 A1 | 8/2020 |

OTHER PUBLICATIONS

Asano et al. (Tetrahedron, 68(1), 272-279, 2012). (Year: 2012).*
International Search report for International Application No. PCT/US2021/044381, dated Nov. 29, 2021, 5 pages.
Written Opinion for International Application No. PCT/US2021/044381, dated Nov. 29, 2021, 7 pages.
Yang et al., Design, synthesis, and biological evaluation of thieno[3,2-d]pyrimidine derivatives as potential simplified phosphatidylinositol 3-kinase alpha inhibitors, Chem Biol Drug Des., 2019, vol. 94, pp. 2013-2022.
Al-Olabi et al., Mosaic RAS/MAPK variants cause sporadic vascular malformations which respond to targeted therapy, The Journal of Clinical Investigation, Apr. 2018, vol. 128, No. 4, pp. 1496-1508.
Castel et al., Somatic PIK3CA mutations as a driver of sporadic venous malformations, Science Translational Medicine, Mar. 30, 2016, vol. 8, No. 332, pp. 1-10, 11 pages.
Couto et al., A Somatic MAP3K3 Mutation Is Associated with Verrucous Venous Malformation, The American Journal of Human Genetics, Mar. 5, 2015, vol. 96, pp. 480-486.
Dannemann et al., Phosphatidylinositol 4,5-bisphosphate (PIP$_2$)-specific AKT1 is oncogenic, Int J Cancer, Jul. 1, 2010, vol. 127, No. 1, pp. 239-244.

(Continued)

*Primary Examiner* — Genevieve S Alley
(74) *Attorney, Agent, or Firm* — Mintz, Levin, Cohn, Ferris, Glovsky & Popeo, P.C.

(57) ABSTRACT

The present invention provides compounds and topical formulations including the compounds for the treatment of vascular malformations, wherein the compounds are according to formula (I):

(I)

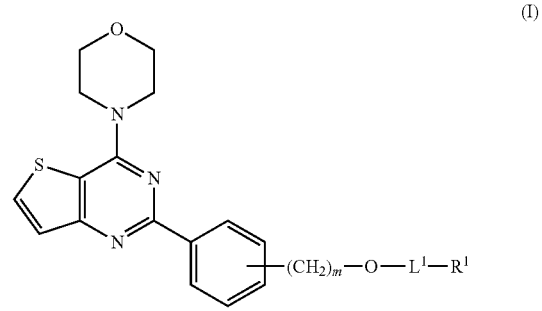

wherein subscript m, $L^1$, $R^1$, and $L^1$-$R^1$ are as described herein.

24 Claims, 14 Drawing Sheets

(56) References Cited

OTHER PUBLICATIONS

European Patent Office, extended European Search Report for European Patent Application No. 16797120.9 dated Dec. 14, 2018, 9 pages.

Fritsch et al., Characterization of the Novel and Specific PI3Kα Inhibitor NVP-BYL719 and Development of the Patient Stratification Strategy for Clinical Trials, American Association for Cancer Research Journals, Molecular Cancer Therapeutics, published online first Mar. 7, 2014, pp. 1117-1130.

Hayakawa et al., Synthesis and biological evaluation of 4-morpholino-2-phenylquinazolines and related derivatives as novel PI3 kinase p110α inhibitors, Bioorganic & Medicinal Chemistry, 2006, vol. 14, pp. 6847-6858.

Hu et al., Tie2-R849W Mutant in Venous Malformations Chronically Activates a Functional STAT1 to Modulate Gene Expression, Journal of Investigative Dermatology, 2008, vol. 128, pp. 2325-2333.

International Search Report for International Application No. PCT/US2016/032779, dated Sep. 15, 2016, 5 pages.

Kurek et al., Somatic Mosaic Activating Mutations in PIK3CA Cause CLOVES Syndrome, The American Journal of Human Genetics, Jun. 8, 2012, vol. 90, pp. 1108-1115.

Luks et al., Lymphatic and other vascular malformative/overgrowth disorders are caused by somatic mutations in PIK3CA, J. Pediatr., Apr. 2015, vol. 166, No. 4, pp. 1048-54.

Sapp et al., A dyadic genotype-phenotype approach to diagnostic criteria for Proteus syndrome, Am J Med Genet, 2019, vol. 181, pp. 565-570.

Shirley et al., Sturge-Weber Syndrome and Port-Wine Stains Caused by Somatic Mutation in GNAQ, N Engl J Med., May 23, 2013, vol. 368, No. 21, pp. 1971-1979.

Vikkula et al., Vascular Dysmorphogenesis Caused by an Activating Mutation in the receptor tyrosine Kinase TIE2, Cell, Dec. 27, 1996, vol. 87, pp. 1181-1190.

Written Opinion for International Application No. PCT/US2016/032779, dated Sep. 15, 2016, 11 pages.

International Search Report for PCT/US2020/016876, dated Jun. 15, 2020, 4 pages.

Rewcastle et al., "Biological characterization of SN32976, a selective inhibitor of PI3K and mTOR with preferential activity to PI3k, in comparison to established pan PI3kα inhibitors", Oncotarget, 2017, vol. 8, No. 29, pp. 47725-47740.

Written Opinion of the International Searching Authority for PCT/US2020/016876 dated Jun. 15, 2020, 5 pages.

Di Blasio et al., PI3K/mTOR inhibition promotes the regression of experimental vascular malformations driven by PIK3CA-activating mutations. Cell Death & Disease, 2018, vol. 9, No. 2, Article No. 25, 15 pages.

European Patent Office, Partial supplementary European search report for EP Application No. 20752673.2, dated Oct. 11, 2022, 12 pages.

Kangas et al., Development of Molecular Therapies for Venous Malformations, Basic & Clinical Pharmacology & Toxicology, 2018, vol. 123, pp. 6-19.

Tan et al., Synthesis and anticancer activities of thieno[3,2-d]pyrimidines as novel HDAC inhibitors, Bioorganic & Medicinal Chemistry, 2014, vol. 22, pp. 358-365.

* cited by examiner

Scheme 2

TOPICAL PHOSPHOINOSITIDE 3-KINASE INHIBITORS

CROSS-REFERENCES TO RELATED APPLICATIONS

This application claims priority to U.S. Provisional Application No. 62/802,093 filed Feb. 6, 2019 and U.S. Provisional Application No. 62/958,049 filed Jan. 7, 2020, each of which is incorporated herein in its entirety for all purpose.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Vascular anomalies are broadly divided into vascular tumours and malformations. These lesions are composed of abnormal vascular elements of various types, and mainly manifesting and worsening in infants, children, and young adults, and persisting through adulthood. Vascular anomalies may be painful, may be complicated by bleeding, infection, or organ dysfunction, and can have secondary effects on other tissues. Current treatment strategies include surgical excision, pulsed laser, and sclerotherapy, which are invasive, with risks of recurrence. There are growing pharmacological options for these vascular anomalies, but, to date, no specific targeted therapies have been developed.

Vascular malformations are clinically challenging because current classifications only take into account the patient outcome and the histological characterization. In fact, many efforts are focused on trying to differentiate these lesions from vascular tumors. While vascular benign tumors, such as Infantile Hemangioma, spontaneously regress and can be treated with propranolol, vascular malformations continue to grow for many years. Venous malformations are of great interest due to current lack of treatment and prognosis. Moreover, pathogenesis of these lesions remain obscure.

The Phosphoinositide 3-Kinase (PI3K) pathway has been extensively studied in tumors due its roles in promoting cellular growth and proliferation. The most common PI3K mutations are in the PIK3CA gene encoding the p110α catalytic subunit, including the "hotspot" activating mutations E545K and H1047R that can lead to constitutive signaling of the pathway. Consequently, activation of the serine/threonine kinase Akt can promote proliferative and cell growth pathways through regulation of mTOR and other intermediates. In addition to driving tumorigenesis, hotspot PIK3CA mutations have also been shown to drive a wide spectrum of non-malignant over-growth disorders collectively termed the PIK3CA-Related Overgrowth Spectrum. More recently, mutations in PIK3CA have been identified in venous malformations (VMs) (Limaye N, et al. Am J Hum Genet. 2015; 97:914-921), the most frequent form of vascular malformations with a frequency of about 1 in 5000 people in the general population. These painful and often disfiguring lesions are characterized by endothelial cell overgrowth, loss of supporting mural cells, and a disorganized extracellular matrix resulting in dilated and distended vessels in a variety of tissues, with common occurrence in the cutaneous layer of the skin (Uebelhoer M, et al. Cold Spring Harb Perspect Med. 2012; 2).

U.S. Pat. No. 6,838,457 discloses that 3-(4-morpholinothieno[3,2-d]pyrimidin-2-yl)phenol has an excellent PI3K inhibiting activity as well as a cancer cell growth inhibiting activity. However, a topical delivery of the compound through the skin for treating vascular malformations by inhibiting the Phosphoinositide 3-Kinase (PI3K) pathway is not known. Considering this, there is urgent need for the development of topical PI3K inhibitors and formulations thereof that can be delivered topically to treat vascular malformations.

BRIEF SUMMARY OF THE INVENTION

In a first aspect, the present invention provides a compound having formula (I):

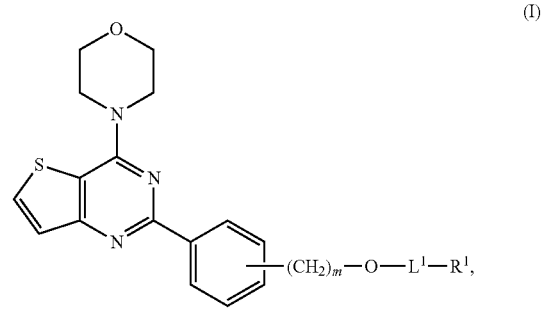

or a hydrate, solvate, and/or a pharmaceutically acceptable salt thereof, wherein:
subscript m is an integer from 0 to 2; and
i) $L^1$ is a bond, —C(O)—, —C(O)O—, —C(O)S—, or —C(O)NH—; and
$R^1$ is $C_{1-6}$ alkyl, $C_{1-6}$ hydroxyalkyl, $C_{1-6}$ haloalkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl;
ii) $L^1$-$R^1$ has the formula:

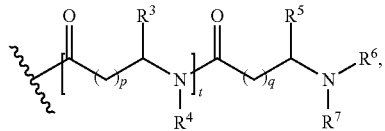

wherein
the wavy line indicates the attachment to the adjacent oxygen atom in formula (I);
subscript t is an integer from 0 to 1;
subscripts p and q are independently an integer from 0 to 2;
$R^3$ is hydrogen or a sidechain of a natural or unnatural amino acid and $R^4$ is hydrogen, or $R^3$ and $R^4$ are combined to be a sidechain of a cyclic amino acid;
$R^5$ is hydrogen or a sidechain of a natural or unnatural amino acid and $R^6$ is hydrogen, $C_{1-6}$ alkyl, or $C_{2-6}$ alkenyl, or $R^5$ and $R^6$ are combined to be a sidechain of a cyclic amino acid; and $R^7$ is hydrogen, $C_{1-6}$ alkyl, $C_{2-6}$ alkenyl, $C_{1-6}$ alkyl-C(O)—, or $C_{2-6}$ alkenyl-C(O)—, or $R^5$ is hydrogen or a sidechain of a natural or unnatural amino acid; and $R^6$ and $R^7$ are combined to form a 3-6 membered heterocycle, optionally having an additional 1-2 heteroatoms selected from O, S, and N as ring vertices; or iii) $L^1$ is —C(O)—; and $R^1$ is an aliphatic chain of a saturated fatty acid having 8-18 carbon atoms or an unsaturated fatty acid having 10-18 carbon atoms.

In a second aspect, the present invention provides a topical formulation for the treatment of vascular malformations. The topical formulation includes:

a) a compound having formula (I):

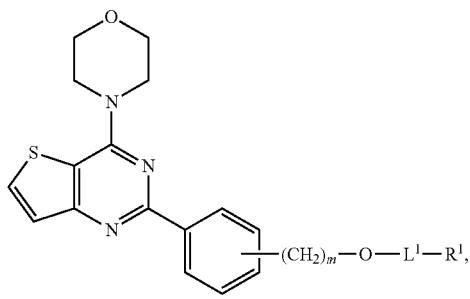

or a hydrate, solvate, and/or a pharmaceutically acceptable salt thereof;

wherein:

subscript m is an integer from 0 to 2; and i) $L^1$ is a bond, —C(O)—, —C(O)O—, —C(O)S—, or —C(O)NH—; and $R^1$ is $C_{1-6}$ alkyl, $C_{1-6}$ hydroxyalkyl, $C_{1-6}$ haloalkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl;

ii) $L^1$-$R^1$ has the formula:

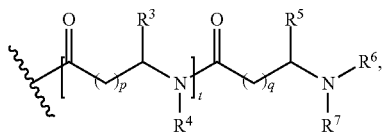

wherein the wavy line indicates the attachment to the adjacent oxygen atom in formula (I);

subscript t is an integer from 0 to 1;

subscripts p and q are independently an integer from 0 to 2;

$R^3$ is hydrogen or a sidechain of a natural or unnatural amino acid and $R^4$ is hydrogen, or $R^3$ and $R^4$ are combined to be a sidechain of a cyclic amino acid;

$R^5$ is hydrogen or a sidechain of a natural or unnatural amino acid and $R^6$ is hydrogen, $C_{1-6}$ alkyl, or $C_{2-6}$ alkenyl, or $R^5$ and $R^6$ are combined to be a sidechain of a cyclic amino acid; and $R^7$ is hydrogen, $C_{1-6}$ alkyl, $C_{2-6}$ alkenyl, $C_{1-6}$ alkyl-C(O)—, or $C_{2-6}$ alkenyl-C(O)—, or $R^5$ is hydrogen or a sidechain of a natural or unnatural amino acid; and $R^6$ and $R^7$ are combined to form a 3-6 membered heterocycle, optionally having an additional 1-2 heteroatoms selected from O, S, and N as ring vertices; or iii) $L^1$ is —C(O)—; and $R^1$ is an aliphatic chain of a saturated fatty acid having 8-18 carbon atoms or an unsaturated fatty acid having 10-18 carbon atoms; and b) one or more topical excipients.

In a third aspect, the present invention provides a method of treating a vascular malformation through inhibiting phosphoinositide-3-kinase (PI3K). The method includes administering to a subject in need thereof, an effective amount of the topical formulation including the compound of formula (I) and one or more topical excipients.

DETAILED DESCRIPTION OF THE INVENTION

I. General

Figure 1:
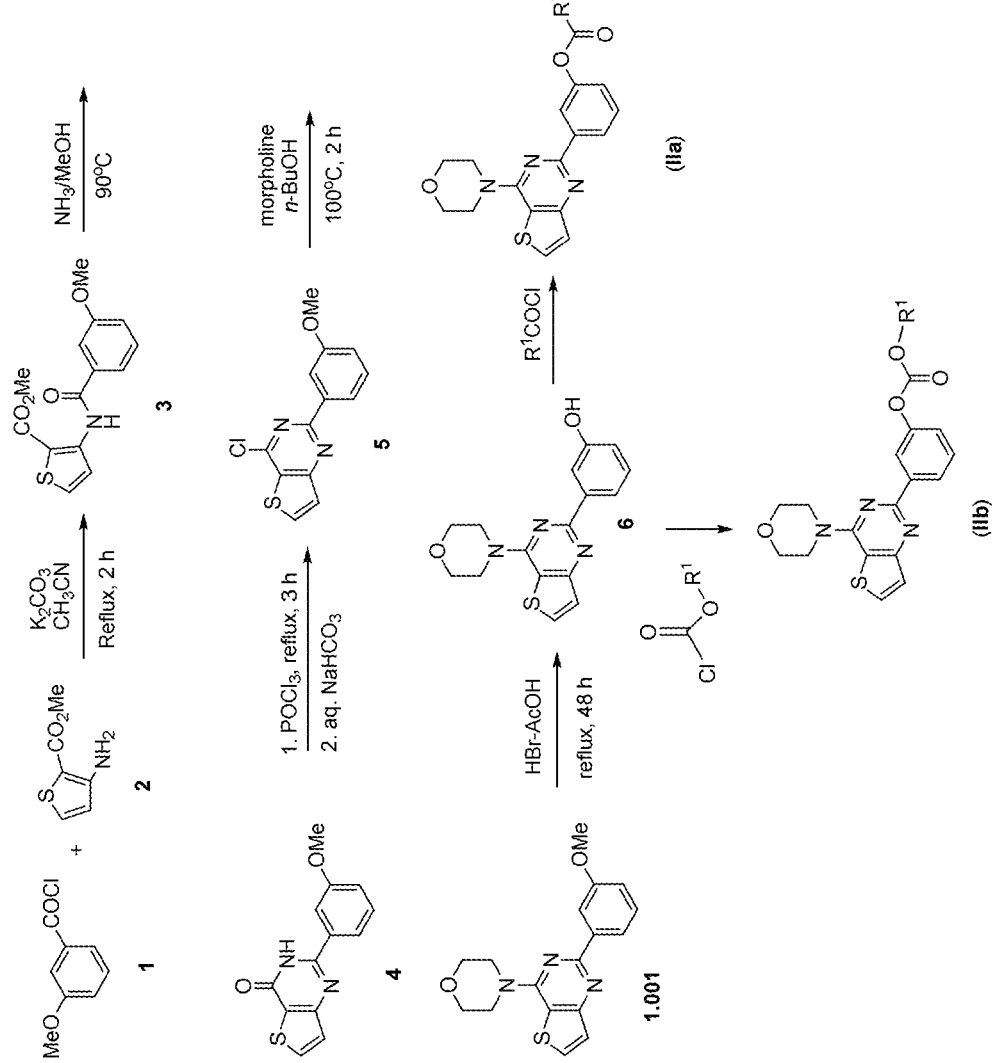
FIG. 1 shows synthesis Scheme 1 for preparing a compound of formula (IIa) or (IIb).

The present invention provides compounds of formula (I) and topical formulations including the compounds of formula (I) for the treatment of vascular malformations. After topical delivery, the compounds of the present invention are substantially converted to the corresponding compounds of formula (IV) that are capable of inhibiting one or more of the phosphoinositide 3-kinase enzymes, which are part of the PI3K/AKT pathway, thereby providing beneficial therapeutic effects for the treatment of vascular malformations. The present invention also provides methods of treating vascular malformations by inhibiting the PI3K/AKT pathway with the topical formulations of the present invention.

II. Definitions

The abbreviations used herein have their conventional meaning within the chemical and biological arts.

"Alkyl" refers to a straight or branched, saturated, aliphatic radical having the number of carbon atoms indicated (i.e., $C_{1-6}$ means one to six carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 24 carbons, such as, but not limited to heptyl, octyl, nonyl, decyl, etc.

"Alkenyl" refers to a straight chain or branched hydrocarbon having at least 2 carbon atoms and at least one double bond and having the number of carbon atom indicated (i.e., $C_{2-6}$ means to two to six carbons). Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-5}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

"Alkoxy" refers to an alkyl group having an oxygen atom that connects the alkyl group to the point of attachment: alkyl-O—. Alkoxy groups can have any suitable number of carbon atoms, such as $C_1$-$C_6$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Hydroxyalkyl" refers to an alkyl group, as defined above, where at least one of the hydrogen atoms is replaced with a hydroxy group. As for the alkyl group, a hydroxyalkyl or alkylhydroxy groups can have any suitable number of carbon atoms, such as $C_1$-$C_6$. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Halogen" or "halo" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_1$-$C_6$. For example, haloalkyl includes trifluoromethyl, fluoromethyl, 2,2,2-trifluoroethyl, etc. In some instances, the term "perfluoro" can be used to define a compound or radical where all the hydrogens are replaced with fluorine. For example, perfluoromethyl refers to 1,1,1-trifluoromethyl.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_3$-$C_8$ cycloalkyl, exemplary groups include, but are not limited to cyclopropyl, cyclobutyl, cyclopentyl, cyclohexyl, cycloheptyl and cyclooctyl. When cycloalkyl a saturated monocyclic $C_{3-6}$ cycloalkyl, exemplary groups include, but are not limited to cyclopropyl, cyclobutyl, cyclopentyl, and cyclohexyl.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

"Aryl-alkyl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of aryl-alkyl groups include, but are not limited to, benzyl (phenyl-$CH_2$—). Aryl-alkyl groups can be substituted or unsubstituted.

"Aryl-alkenyl" refers to a radical having both an alkenyl component and an aryl component, where the alkenyl component links the aryl component to the point of attachment. The alkenyl component is as defined above, except that the alkenyl component is at least divalent, an alkenylene, to link to the aryl component and to the point of attachment. The alkenyl component can include any number of carbons, such as $C_2$, $C_{2-3}$, $C_{2-4}$, $C_{2-5}$, $C_{2-6}$, $C_{2-8}$, $C_3$, $C_{3-4}$, $C_{3-5}$, $C_{3-6}$, $C_4$, $C_{4-5}$, $C_{4-5}$, $C_5$, $C_{5-6}$, and $C_6$. The alkenyl component can have any suitable number of double bonds, including, but not limited to, 1, 2, 3, 4, 5 or more. The aryl component is as defined above. Examples of aryl-alkenyl groups include, but not limited to phenyl-CH=CH—. Aryl-alkenyl groups can be substituted or unsubstituted.

"Heterocycle" or "heterocycloalkyl" refers to a saturated ring system having from 3 to 12 ring members and from 1 to 4 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

"N-linked heterocycloalkyl" or "nitrogen-linked heterocycloalkyl" refers to the heterocycloalkyl group linked via N-position on the ring. For example, N-linked aziridinyl is aziridin-1-yl, N-linked azetidinyl is azetidin-1-yl, N-linked pyrrolidinyl is pyrrolidin-1-yl, N-linked piperidinyl is piperidin-1-yl, N-linked pyrazolidinyl is pyrazolidin-1-yl or pyrazolidin-2-yl, N-linked imidazolidinyl can be imidazolidin-1-yl or imidazolidin-3-yl, N-linked piperazinyl is piperazin-1-yl or piperazin-4-yl, N-linked oxazolidinyl is oxazolidin-3-yl, N-linked isoxazolidiny is isoxazolidin-2-yl, N-linked thiazolidinyl is thiazolidin-3-yl, N-linked isothiazolidinyl is isothiazolidin-2-yl, and N-linked morpholinyl is 4-morpholinyl.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Amino acid" refers to naturally occurring and synthetic amino acids, as well as amino acid analogs and amino acid mimetics that function in a manner similar to the naturally occurring amino acids. Amino acids contain amine (—NH$_2$ or —NH) and carboxyl (—COOH) functional groups, along with a side chain (R group) specific to each amino acid. Amino acids having the amine group attached to the first (alpha-) carbon adjacent to the carboxylic acid group are referred as α-amino acids.

Amino acids may be referred to herein by either the commonly known three letter symbols or by the one-letter symbols recommended by the IUPAC-IUB Biochemical Nomenclature Commission. Examples of naturally occurring amino acids include the twenty amino acids selected from the group consisting of alanine (Ala/A), glycine (Gly/G), isoleucine (Ile/I), leucine (Leu/L), proline (Pro/P), valine (Val/V), phenylalanine (Phe/F), tryptophan (Trp/W), tyrosine (Tyr/Y), aspartic acid (Asp/D), glutamic acid (Glu/E), arginine (Arg/R), histidine (His/H), lysine (Lys/K), serine (Ser), threonine (Thr/T), asparagine (Asn/N), glutamine (Gln/Q), methionine (Met/M), and cysteine (Cys/C).

"Unnatural amino acids" refers compounds that can, but do not necessarily have the same basic structure as a naturally occurring amino acid. In some embodiments, unnatural amino acids have modified side chains (e.g., norleucine) or modified peptide backbones, but retain the same basic chemical structure as a naturally occurring amino acid. Unnatural amino acids include, but are not limited to homoserine, norleucine, methionine sulfoxide, methionine methyl sulfonium, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Alkylene glycol" refers to a compound having the formula of HO-[alkylene-O]—H, wherein the alkylene group has 2 to 6, 2 to 4, or 2 to 3 carbon atoms. In some embodiments, the alkylene glycol is a $C_{2-6}$ alkylene glycol. In some embodiments, the $C_{2-6}$ alkylene glycol is propylene glycol (1.2-propanediol).

"Di-alkylene glycol" refers to a compound having the formula of HO-(alkylene-O)$_2$—H, wherein the alkylene group has 2 to 6, 2 to 4, or 2 to 3 carbon atoms. In some embodiments, the di-alkylene glycol is a di-($C_{2-6}$ alkylene) glycol. In some embodiments, the di-($C_{2-6}$ alkylene) glycol is dipropylene glycol. Dipropylene glycol can include one or more isomers, for example 4-oxa-2,6-heptandiol, 2-(2-hydroxy-propoxy)-propan-1-ol, 2-(2-hydroxy-1-methyl-ethoxy)-propan-1-ol, and 3,3'-oxybis(propan-1-ol).

"Polyethylene glycol" refers to a polymer having the formula of HO—(CH$_2$CH$_2$O)$_n$—OH with variations in subscript "n". Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to PEG200, PEG300, PEG400, PEG600, and PEG900. The number following the "PEG" in the name refers to the average molecular weight of the polymer.

"Fatty acid" refers to a carboxylic acid with a long aliphatic chain, which is straight or branched and saturated or unsaturated. Most naturally occurring fatty acids have an unbranched chain of an even number of carbon atoms, from 8 to 24.

"Saturated fatty acid" refers to a fatty acid having an alkyl chain. The alkyl component is as defined above. The saturated fatty acid having 8-24 carbon atoms includes caprylic acid, pelargonic acid, capric acid, neodecanoic acid, undecylic acid, lauric acid, tridecylic acid, myristic acid, pentadecylic acid, palmitic acid, margaric acid, stearic acid, isostearic acid, nonadecylic acid, arachidic acid, heneicosylic acid, behenic acid, tricosylic acid, and lignoceric acid. In some embodiments, the saturated fatty acid having 8-18 carbon atoms is caprylic acid, pelargonic acid, capric acid, neodecanoic acid, undecylic acid, lauric acid, tridecylic acid, myristic acid, pentadecylic acid, palmitic acid, margaric acid, stearic acid, or isostearic acid.

"Aliphatic chain of a saturated fatty acid" refers to the alkyl chain of the corresponding saturated fatty acid as defined above. The aliphatic chain has one carbon atom less than the corresponding saturated fatty acid, for example the aliphatic chain of a saturated fatty acid having 8-18 carbon atoms has 7-17 carbon atoms.

"Unsaturated fatty acid" refers to a carboxylic acid with a long aliphatic chain having one or more C=C double bonds. The C=C double bonds can give either cis or trans isomers. A cis configuration means that the two hydrogen atoms adjacent to the double bond lie on the same side of the chain. A trans configuration, by contrast, means that the adjacent two hydrogen atoms lie on opposite sides of the chain. Unsaturated fatty acid can include 10 to 24 carbons. The unsaturated fatty acid includes mono-unsaturated fatty acids, di-unsaturated fatty acids, and poly-unsaturated fatty acids.

Mono-unsaturated fatty acids include, but are not limited to, caproleic acid, lauroleic acid, myristoleic acid, palmitoleic acid, sapienic acid, oleic acid, elaidic acid, vaccenic acid, gadoleic acid, eicosenoic acid, erucic acid, brassidic acid, and nervonic acid. In some embodiments, the unsaturated fatty acid having 10-18 carbon atoms is caproleic acid, lauroleic acid, myristoleic acid, palmitoleic acid, sapienic acid, oleic acid, elaidic acid, vaccenic acid, linoleic acid, alpha-linolenic acid, gamma-linolenic acid, columbinic acid, pinolenic acid, or stearidonic acid.

Di-unsaturated fatty acids include, but are not limited to, linoleic acid, eicosadienoic acid, and docosadienoic acid. The di-unsaturated fatty acid having 18 carbon atoms is linoleic acid.

Poly-unsaturated fatty acids include, but are not limited to, alpha-linolenic acid, gamma-linolenic acid, columbinic acid, pinolenic acid, eleostearic acid, beta-eleostearic acid, mead acid, dihomo-γ-linolenic acid, eicosatrienoic acid, stearidonic acid, arachidonic acid, eicosapentaenoic acid, docosapentaenoic acid, and docosahexaenoic acid. In some embodiments, the poly-unsaturated fatty acid having 18 carbon atoms is alpha-linolenic acid, gamma-linolenic acid, columbinic acid, pinolenic acid, or stearidonic acid.

"Aliphatic chain of an unsaturated fatty acid" refers to the aliphatic chain of the corresponding unsaturated fatty acid as defined above. The aliphatic chain has one carbon atom less than the corresponding unsaturated fatty acid, for example the aliphatic chain of an unsaturated fatty acid having 10-18 carbon atoms has 9-17 carbon atoms.

"Fatty alcohol" refers to a primary alcohol with a long aliphatic chain, which is either saturated or unsaturated. The fatty alcohol can also range from as few as 4-6 carbons to as many as 22-26 carbons. The fatty alcohol includes, but is not limited to, capric alcohol, undecyl alcohol, lauryl alcohol, tridecyl alcohol, myristyl alcohol, pentadecyl alcohol, cetyl alcohol, palmitoleyl alcohol (unsaturated), heptadecyl alcohol, stearyl alcohol, oleyl alcohol (unsaturated), nonadecyl alcohol, arachidyl alcohol, heneicosyl alcohol, behenyl alcohol, erucyl alcohol (unsaturated), and lignoceryl alcohol.

"Fatty ester" or "fatty acid ester" refers to a type of ester that results from the combination of a fatty acid with an alcohol.

"Glyceride" refers to a fatty ester when the alcohol component is glycerol. The glyceryl fatty esters (or glycerides) produced can be monoglycerides, diglycerides, or triglycerides. "Monoglyceride" is glyceride consisting of one fatty acid chain covalently bonded to a glycerol molecule through an ester linkage. "Diglyceride" is glyceride consisting of two fatty acid chains covalently bonded to a glycerol molecule through ester linkages. "Triglyceride" is glyceride consisting of three fatty acid chains covalently bonded to a glycerol molecule through ester linkages.

"Sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes products sold under names Span™ 20 (Sorbitan monolaurate), 40 (Sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

"Adipate" refers to a diester of adipic acid; "sebacate" refers to a diester of sebacic acid; "laurate" refers to an ester of lauric acid; "myristate" refers to an ester of myristic acid"; "palmitate" refers an ester of palmitic acid; and "stearate" refers an ester of stearic acid". In some embodiments, an adipate, a sebacate, a laurate, a myristate, a palmitate, or a stearate is a di-$C_{1-6}$ alkyl ester of adipic acid, a di-$C_{1-6}$ alkyl ester of sebacic acid, a $C_{1-6}$ alkyl ester of palmitic acid, or a glycol monoester of stearic acid, respectively.

"Solvate" refers to a compound provided herein or a salt thereof, that further includes a stoichiometric or non-stoichiometric amount of solvent bound by non-covalent intermolecular forces. The solvent herein refers to non-water solvent.

"Hydrate" refers to a compound that is complexed to at least one water molecule. The compounds of the present invention can be complexed with from 1 to 10 water molecules.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. Pharmaceutical excipients useful in the present invention for transdermal/topical delivery include, but are not limited to, enhancers, solubilizers, antioxidants, plastisizers, thickeners, polymers, and pressure sensitive adhesives. One of skill in the art will recognize that other pharmaceutical excipients are useful in the present invention.

"Weight of the base formulation" refers to a total weight of a formulation without a compound of formula (I) or 3-(4-morpholinothieno(3,2-d)pyrimidin-2-yl)phenol (abbreviated as MTPP) and a gelling agent.

"The fatty acid is present in an amount of about x % to about y % by weight of the base formulation" refers to the fatty acid present in an amount of about x % to about y % by weight as compared to the total weight of the base formulation without a compound of formula (I) or MTPP and a gelling agent.

"The compound of formula (I) is present in an amount of about x % by weight of the base formulation" refers the weight percentage of the compound of formula (I) as compared to the total weight of the formulation without the compound of formula (I) and a gelling agent.

"The one or more gelling agents are present in an amount of about x % to about y % by weight of the base formulation" refers the weight percentage of the gelling agents as compared to the total weight of the formulation without a compound of formula (I) or MTPP and the gelling agents. For example, "the hydroxypropyl cellulose is present in an amount of about x % to about y % by weight of the base formulation" refers the weight percentage of the hydoxypropyl cellulose as compared to the total weight of the base formulation without a compound of formula (I) or MTPP and the hydoxypropyl cellulose.

"A relative purity of the compound of formula (I) in the topical formulation" refers to the purity of the compound of formula (I) at a certain time point (e.g., day 10) stored under stressed conditions (e.g., 80° C.) or under normal storage conditions (e.g., room temperature) as compared to an initial purity of the compound of formula (I) at time zero (i.e., day 0). As always, the relative purity of the compound of formula (I) at time zero (i.e., day 0) is set as 100%.

"$IC_{50}$" refers to an amount, concentration or dosage of a particular test compound that achieves a 50% inhibition of a maximal response in an assay that measures such response.

"Inhibition", "inhibits" and "inhibitor" refer to a compound that prohibits or a method of prohibiting, a specific action or function.

"Administering" refers to topical administration, for example as a lotion, a spray, an ointment, a cream, a gel, a paste, or a patch.

"Topical" means application of a suitable compound (e.g. active agent) or composition comprising a compound (e.g. active agent) to the skin to treat diseases or conditions, for example vascular malformation. In some embodiments, "topical" means application of a suitable compound (e.g. active agent) or composition comprising a compound (e.g. active agent) to the skin with adequate penetration of the epidermis or dermis to treat the vascular malformation. In some embodiments of topical application, the compound or composition penetrates the epidermis or dermis without significant systemic exposure nor intent to treat or prevent a disease of another organ system. In some embodiments of topical application, the compound or composition is delivered by transdermal across the skin for systemic distribution. Examples include transdermal patches used for drug delivery.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

III. Compounds

In one aspect, the present invention provides a compound having formula (I):

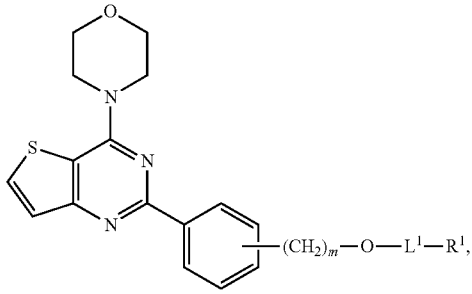

(I)

or a hydrate, solvate, and/or a pharmaceutically acceptable salt thereof,
wherein:
subscript m is an integer from 0 to 2; and
i) $L^1$ is a bond, —C(O)—, —C(O)O—, —C(O)S—, or —C(O)NH—; and
$R^1$ is $C_{1-6}$ alkyl, $C_{1-6}$ hydroxyalkyl, $C_{1-6}$ haloalkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl;
ii) $L^1$-$R^1$ has the formula:

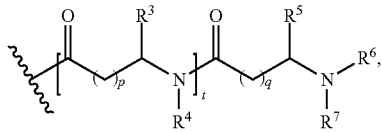

wherein
the wavy line indicates the attachment to the adjacent oxygen atom in formula (I);
subscript t is an integer from 0 to 1;
subscripts p and q are independently an integer from 0 to 2;
$R^3$ is hydrogen or a sidechain of a natural or unnatural amino acid and $R^4$ is hydrogen, or $R^3$ and $R^4$ are combined to be a sidechain of a cyclic amino acid;
$R^5$ is hydrogen or a sidechain of a natural or unnatural amino acid and $R^6$ is hydrogen, $C_{1-6}$ alkyl, or $C_{2-6}$ alkenyl, or $R^5$ and $R^6$ are combined to be a sidechain of a cyclic amino acid; and
$R^7$ is hydrogen, $C_{1-6}$ alkyl, $C_{2-6}$ alkenyl, $C_{1-6}$ alkyl-C(O)—, or $C_{2-6}$ alkenyl-C(O)—, or
$R^5$ is hydrogen or a sidechain of a natural or unnatural amino acid; and
$R^6$ and $R^7$ are combined to form a 3-6 membered heterocycle, optionally having an additional 1-2 heteroatoms selected from O, S, and N as ring vertices; or
iii) $L^1$ is —C(O)—; and
$R^1$ is an aliphatic chain of a saturated fatty acid having 8-18 carbon atoms or an unsaturated fatty acid having 10-18 carbon atoms.

In some embodiments, subscript m is 0 or 1. In some embodiments, subscript m is 1. In some embodiments, subscript m is 0.

In some embodiments, subscript m is 0 and the compound is represented by formula (II):

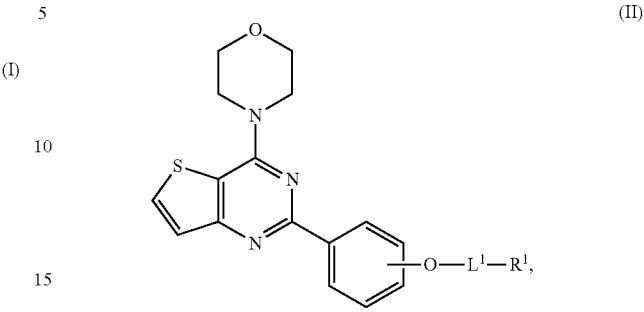

(II)

wherein $L^1$, $R^1$, and $L^1$-$R^1$ are as defined herein in any aspect or embodiments described herein.

In some embodiments, subscript m is 1 and the compound is represented by formula (III):

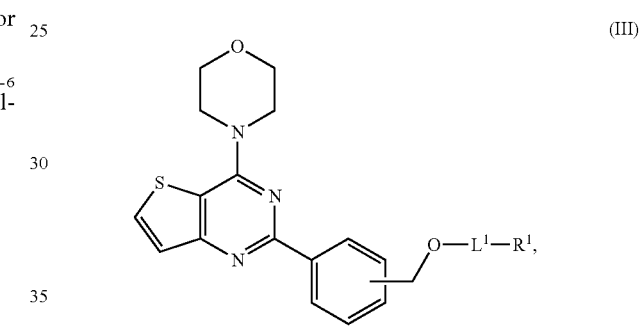

(III)

wherein $L^1$, $R^1$, and $L^1$-$R^1$ are as defined herein in any aspect or embodiments described herein.

In some embodiments of any one of formulae (I), (II), and (III), $L^1$ is a bond. In some embodiments, $L^1$ is —C(O)—. In some embodiments, $L^1$ is —C(O)O—. In some embodiments, $L^1$ is —C(O)NH—. In some embodiments, $L^1$ is —C(O)S—.

In some embodiments of formula (II), $L^1$ is —C(O)— and the compound is represented by formula (IIa):

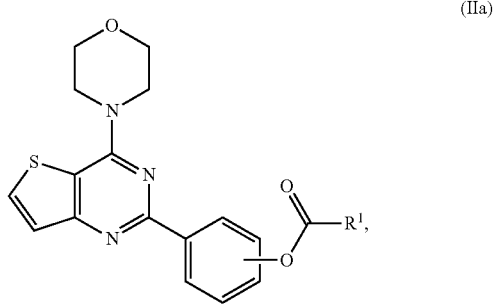

(IIa)

wherein $R^1$ or —C(O)—$R^1$ as $L^1$-$R^1$ are as defined herein in any aspect or embodiments described herein.

In some embodiments of formula (II), the compound is represented by any one of formulae (IIb), (IIc), and (IId):

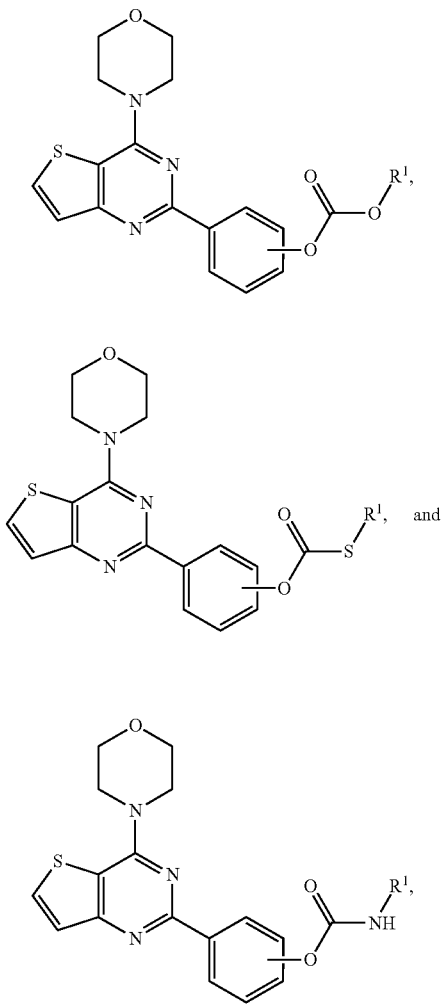

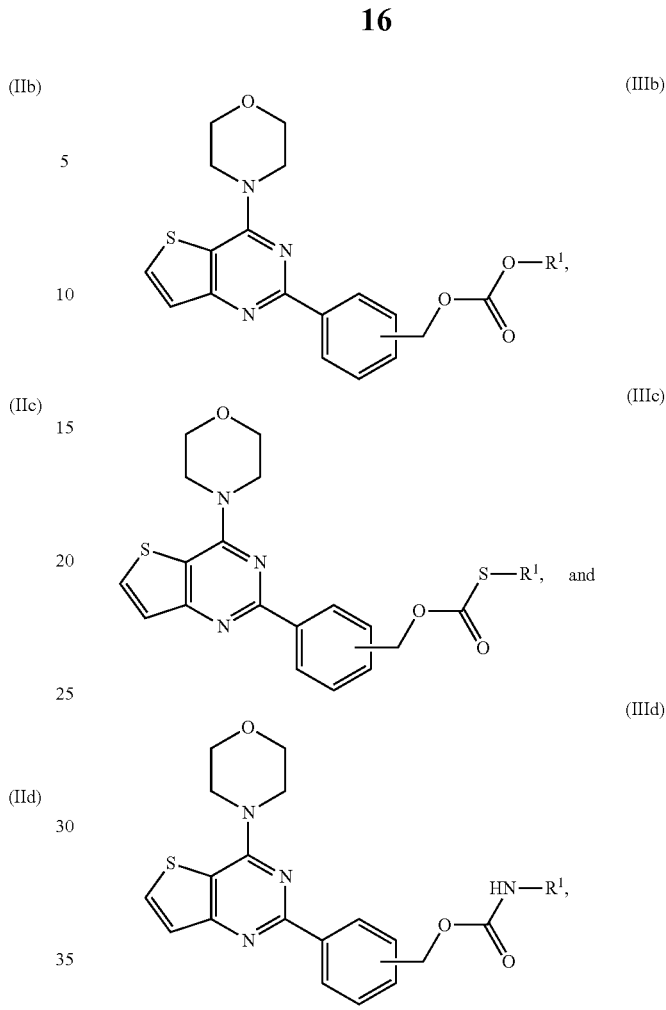

wherein $R^1$ is $C_{1-6}$ alkyl, $C_{1-6}$ hydroxyalkyl, $C_{1-6}$ haloalkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl.

In some embodiments of formula (III), $L^1$ is —C(O)— and the compound is represented by formula (IIIa):

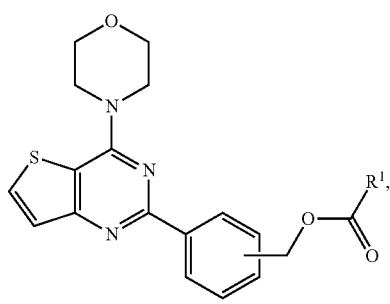

wherein $R^1$ or —C(O)—$R^1$ as $L^1$-$R^1$ are as defined herein in any aspect or embodiments described herein.

In some embodiments of formula (III), the compound is represented by any one of formulae (IIIb), (IIIc), and (IIId):

wherein $R^1$ is $C_{1-6}$ alkyl, $C_{1-6}$ hydroxyalkyl, $C_{1-6}$ haloalkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl.

With reference to any one of formulae (I) to (III), (IIa) to (IId), and (IIIa) to (IIId), in some embodiments, $R^1$ is $C_{1-6}$ alkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl.

In some embodiments of any one of formulae (I) to (III), (IIa) to (IId), and (IIIa) to (IIId), $R^1$ is $C_{1-6}$ alkyl. In some embodiments, $R^1$ is methyl, ethyl, propyl, isopropyl, butyl, isobutyl, sec-butyl, tert-butyl, pentyl, isopentyl, or hexyl. In some embodiments, $R^1$ is methyl. In some embodiments, $R^1$ is ethyl.

In some embodiments of any one of formulae (I) to (III), (IIa) to (IId), and (IIIa) to (IIId), $R^1$ is $C_{2-6}$ alkenyl. In some embodiments, $R^1$ is vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. In some embodiments, $R^1$ is propenyl.

In some embodiments of any one of formulae (I) to (III), (IIa) to (IId), and (IIIa) to (IIId), $R^1$ is $C_{6-10}$ aryl-$C_{2-6}$ alkenyl. In some embodiments, $R^1$ is phenyl-$C_{2-6}$ alkenyl. In some embodiments, $R^1$ is phenyl-CH=CH—.

With reference to any one of formulae (I), (II), (IIa), (III), and (IIIa), $L^1$-$R^1$ or —C(O)$R^1$ has the formula:

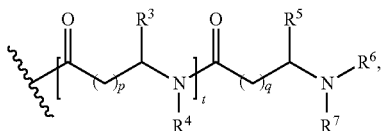

wherein the wavy line indicates the attachment to the adjacent oxygen atom in any one of formulae (I), (II), (IIa), (III), and (IIIa);

subscript t is an integer from 0 to 1;

subscripts p and q are independently an integer from 0 to 2;

$R^3$ is hydrogen or a sidechain of a natural or unnatural amino acid and $R^4$ is hydrogen, or $R^3$ and $R^4$ are combined to be a sidechain of a cyclic amino acid;

$R^5$ is hydrogen or a sidechain of a natural or unnatural amino acid and $R^6$ is hydrogen, $C_{1-6}$ alkyl, or $C_{2-6}$ alkenyl, or $R^5$ and $R^6$ are combined to be a sidechain of a cyclic amino acid; and $R^7$ is hydrogen, $C_{1-6}$ alkyl, $C_{2-6}$ alkenyl, $C_{1-6}$ alkyl-C(O)—, or $C_{2-6}$ alkenyl-C(O)—, or $R^5$ is hydrogen or a sidechain of a natural or unnatural amino acid; and $R^6$ and $R^7$ are combined to form a 3-6 membered heterocycle, optionally having an additional 1-2 heteroatoms selected from O, S, and N as ring vertices.

In some embodiments of any one of formulae (I), (II), (IIa), (III), and (IIIa), subscript t is 1. In some embodiments, subscript t is 0.

In some embodiments of any one of formulae (I), (II), (IIa), (III), and (IIIa), subscript t is 1 and subscripts p and q are independently an integer from 0 to 2. In some embodiments, subscript t is 1 and subscripts p and q are independently 0 or 1. In some embodiments, subscript t is 1 and subscripts p and q are each 0.

When subscript t is 1 and subscripts p and q are each 0, in some embodiments of any one of formulae (I), (II), (IIa), (III), and (IIIa), $R^4$ is hydrogen; and $R^3$ is a side chain of an amino acid selected from the group consisting of alanine (Ala/A), glycine (Gly/G), isoleucine (Ile/I), leucine (Leu/L), valine (Val/V), phenylalanine (Phe/F), tryptophan (Trp/W), tyrosine (Tyr/Y), aspartic acid (Asp/D), glutamic acid (Glu/E), arginine (Arg/R), histidine (His/H), lysine (Lys/K), serine (Ser/S), threonine (Thr/T), asparagine (Asn/N), glutamine (Gln/Q), methionine (Met/M) and cysteine (Cys/C). In some embodiments, $R^4$ is hydrogen; and $R^3$ is a side chain of an amino acid selected from the group consisting of alanine (Ala/A), glycine (Gly/G), isoleucine (Ile/I), leucine (Leu/L), valine (Val/V), phenylalanine (Phe/F), serine (Ser), threonine (Thr/T), asparagine (Asn/N), and glutamine (Gln/Q). In some embodiments, $R^4$ is hydrogen; and $R^3$ is a side chain of an amino acid selected from the group consisting of alanine (Ala/A), glycine (Gly/G), isoleucine (Ile/I), leucine (Leu/L), valine (Val/V), and phenylalanine (Phe/F). In some embodiments, $R^3$ and $R^4$ are combined to form proline (Pro/P).

In some embodiments of any one of formulae (I), (II), (IIa), (III), and (IIIa), $R^5$ is a side chain of an amino acid selected from the group consisting of alanine (Ala/A), glycine (Gly/G), isoleucine (Ile/I), leucine (Leu/L), valine (Val/V), phenylalanine (Phe/F), tryptophan (Trp/W), tyrosine (Tyr/Y), aspartic acid (Asp/D), glutamic acid (Glu/E), arginine (Arg/R), histidine (His/H), lysine (Lys/K), serine (Ser/S), threonine (Thr/T), asparagine (Asn/N), glutamine (Gln/Q), methionine (Met/M) and cysteine (Cys/C). In some embodiments, $R^5$ is a side chain of an amino acid selected from the group consisting of alanine (Ala/A), glycine (Gly/G), isoleucine (Ile/I), leucine (Leu/L), valine (Val/V), phenylalanine (Phe/F), serine (Ser), threonine (Thr/T), asparagine (Asn/N), and glutamine (Gln/Q). In some embodiments, $R^5$ is a side chain of an amino acid selected from the group consisting of alanine (Ala/A), glycine (Gly/G), isoleucine (Ile/I), leucine (Leu/L), valine (Val/V), and phenylalanine (Phe/F).

In some embodiments of any one of formulae (I), (II), (IIa), (III), and (IIIa), $R^6$ and $R^7$ are each independently hydrogen, $C_{1-6}$ alkyl, or $C_{2-6}$ alkenyl. In some embodiments, $R^6$ and $R^7$ are each hydrogen. In some embodiments, one of $R^6$ and $R^7$ is hydrogen and the other one is $C_{1-6}$ alkyl or $C_{2-6}$ alkenyl. In some embodiments, one of $R^6$ and $R^7$ is hydrogen and the other one is $C_{1-6}$ alkyl. In some embodiments, one of $R^6$ and $R^7$ is hydrogen and the other one is methyl, ethyl, propyl, isopropyl, butyl, pentyl, or hexyl. In some embodiments, $R^6$ and $R^7$ are each independently $C_{1-6}$ alkyl. In some embodiments, $R^6$ and $R^7$ are each independently methyl, ethyl, propyl, isopropyl, butyl, pentyl, or hexyl. In some embodiments, $R^6$ and $R^7$ are each methyl. In some embodiments, $R^6$ and $R^7$ are each independently $C_{2-6}$ alkenyl. In some embodiments, $R^6$ and $R^7$ are each —$CH_2CH=CH_2$.

In some embodiments of any one of formulae (I), (II), (IIa), (III), and (IIIa), $R^6$ is hydrogen, $C_{1-6}$ alkyl, or $C_{2-6}$ alkenyl; and $R^7$ is $C_{1-6}$ alkyl-C(O)—, or $C_{2-6}$ alkenyl-C(O)—. In some embodiments, $R^7$ is methyl-C(O)—, ethyl-C(O)—, propyl-C(O)—, isopropyl-C(O)—, butyl-C(O)—, pentyl-C(O)—, or hexyl-C(O)—. In some embodiments, $R^6$ is hydrogen; and $R^7$ is —$C(O)CH_3$.

In some embodiments of any one of formulae (I), (II), (IIa), (III), and (IIIa), $R^5$ and $R^6$ are combined to form proline (Pro/P); and $R^7$ is hydrogen, $C_{1-6}$ alkyl, $C_{2-6}$ alkenyl, $C_{1-6}$ alkyl-C(O)—, or $C_{2-6}$ alkenyl-C(O)—. In some embodiments, $R^5$ and $R^6$ are combined to form proline (Pro/P); and $R^7$ is hydrogen. In some embodiments, $R^5$ and $R^6$ are combined to form proline (Pro/P); and $R^7$ is $C_{1-6}$ alkyl. In some embodiments, $R^5$ and $R^6$ are combined to form proline (Pro/P); and $R^7$ is methyl. In some embodiments, $R^5$ and $R^6$ are combined to form proline (Pro/P); and $R^7$ is $C_{1-6}$ alkyl-C(O)—. In some embodiments, $R^5$ and $R^6$ are combined to form proline (Pro/P); and $R^7$ is —$C(O)CH_3$.

In some embodiments of any one of formulae (I), (II), (IIa), (III), and (IIIa), $R^6$ and $R^7$ are combined to form a 3-6 membered heterocycle, optionally having additional 1-2 heteroatoms selected from O, S, and N as ring vertices. In some embodiments, $R^6$ and $R^7$ are combined to form a 3-6 membered heterocycle selected from N-linked aziridinyl, N-linked azetidinyl, N-linked pyrrolidinyl, N-linked piperidinyl, N-linked piperazinyl, and N-linked morpholinyl.

In some embodiments of any one of formulae (I), (II), (IIa), (III), and (IIIa), subscript p is 1; and $R^3$ is hydrogen. In some embodiments, subscript q is 1; and $R^5$ is hydrogen. In some embodiments, subscript p is 2; and $R^3$ is hydrogen. In some embodiments, subscript q is 2; and $R^5$ is hydrogen.

In some embodiments of any one of formulae (I), (II), and (IIa), subscripts t and q are each 0, and the compound is represented by the formula (IIa-1):

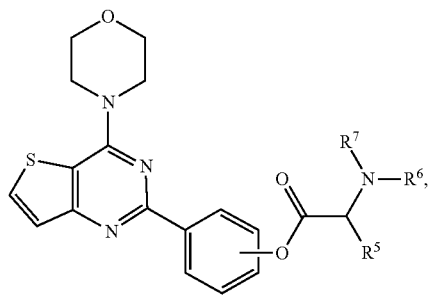

(IIa-1)

wherein $R^5$, $R^6$, and $R^7$ are as defined herein in any aspect or embodiments described herein.

In some embodiments of any one of formulae (I), (III), and (IIIa), subscripts t and q are each 0, and the compound is represented by the formula (IIIa-1):

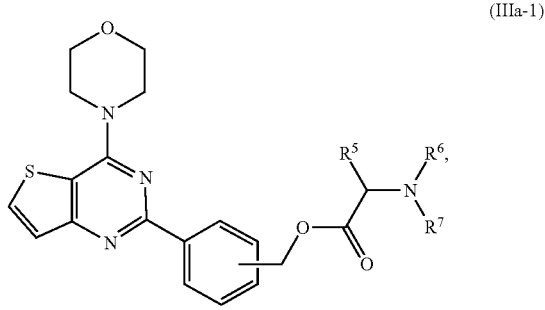

(IIIa-1)

wherein $R^5$, $R^6$, and $R^7$ are as defined herein in any aspect or embodiments described herein.

With reference to formula (IIa-1) or (IIIa-1), in some embodiments, $R^5$ is a side chain of an amino acid selected from the group consisting of alanine (Ala/A), glycine (Gly/G), isoleucine (Ile/I), leucine (Leu/L), valine (Val/V), and phenylalanine (Phe/F).

In some embodiments of formula (IIa-1) or (IIIa-1), $R^6$ and $R^7$ are each independently hydrogen, $C_{1-6}$ alkyl, or $C_{2-6}$ alkenyl. In some embodiments, $R^6$ and $R^7$ are each independently hydrogen, methyl, ethyl, propyl, isopropyl, butyl, pentyl, or hexyl. In some embodiments, $R^6$ and $R^7$ are each hydrogen. In some embodiments, $R^6$ and $R^7$ are each methyl.

In some embodiments of formula (IIa-1) or (IIIa-1), $R^6$ is hydrogen, $C_{1-6}$ alkyl, or $C_{2-6}$ alkenyl; and $R^7$ is $C_{1-6}$ alkyl-C(O)—, or $C_{2-6}$ alkenyl-C(O)—. In some embodiments, $R^7$ is methyl-C(O)—, ethyl-C(O)—, propyl-C(O)—, isopropyl-C(O)—, butyl-C(O)—, pentyl-C(O)—, or hexyl-C(O)—. In some embodiments, $R^6$ is hydrogen; and $R^7$ is —C(O)CH$_3$. In some embodiments, $R^6$ is methyl; and $R^7$ is —C(O)CH$_3$.

With reference to any one of formulae (I), (II), (IIa), (III), and (IIIa), $L^1$ is —C(O)—; and $R^1$ is an aliphatic chain of a saturated fatty acid having 8-18 carbon atoms or an unsaturated fatty acid having 10-18 carbon atoms.

In some embodiments of any one of formulae (I), (II), (IIa), (III), and (IIIa), $L^1$ is —C(O)—; and $R^1$ is an aliphatic chain of a saturated fatty acid having 8-18 carbon atoms. In some embodiments, the saturated fatty acid having 8-18 carbon atoms is selected from the group consisting of caprylic acid, pelargonic acid, capric acid, neodecanoic acid, undecylic acid, lauric acid, tridecylic acid, myristic acid, pentadecylic acid, palmitic acid, margaric acid, stearic acid, and isostearic acid. In some embodiments, $L^1$ is —C(O)—; and $R^1$ is the aliphatic chain of caprylic acid. In some embodiments, $L^1$ is —C(O)—; and $R^1$ is the aliphatic chain of pelargonic acid. In some embodiments, $L^1$ is —C(O)—; and $R^1$ is the aliphatic chain of capric acid. In some embodiments, $L^1$ is —C(O)—; and $R^1$ is the aliphatic chain of neodecanoic acid. In some embodiments, $L^1$ is —C(O)—; and $R^1$ is the aliphatic chain of undecylic acid. In some embodiments, $L^1$ is —C(O)—; and $R^1$ is the aliphatic chain of lauric acid. In some embodiments, $L^1$ is —C(O)—; and $R^1$ is the aliphatic chain of tridecylic acid. In some embodiments, $L^1$ is —C(O)—; and $R^1$ is the aliphatic chain of myristic acid. In some embodiments, $L^1$ is —C(O)—; and $R^1$ is the aliphatic chain of pentadecylic acid. In some embodiments, $L^1$ is —C(O)—; and $R^1$ is the aliphatic chain of palmitic acid. In some embodiments, $L^1$ is —C(O)—; and $R^1$ is the aliphatic chain of margaric acid. In some embodiments, $L^1$ is —C(O)—; and $R^1$ is the aliphatic chain of stearic acid. In some embodiments, $L^1$ is —C(O)—; and $R^1$ is the aliphatic chain of isostearic acid.

In some embodiments of any one of formulae (I), (II), (IIa), (III), and (IIIa), $L^1$ is —C(O)—; and $R^1$ is an aliphatic chain of an unsaturated fatty acid having 10-18 carbon atoms. In some embodiments, the unsaturated fatty acid having 10-18 carbon atoms is a mono-unsaturated fatty acid having 10-18 carbon atoms, a di-unsaturated fatty acid having 18 carbon atoms, or a poly-unsaturated fatty acid having 18 carbon atoms.

In some embodiments of any one of formulae (I), (II), (IIa), (III), and (IIIa), $L^1$ is —C(O)—; and $R^1$ is an aliphatic chain of a mono-unsaturated fatty acid having 10-18 carbon atoms. In some embodiments, the mono-unsaturated fatty acid having 10-18 carbon atoms is selected from the group consisting of caproleic acid, lauroleic acid, myristoleic acid, palmitoleic acid, sapienic acid, oleic acid, elaidic acid, and vaccenic acid. In some embodiments, $L^1$ is —C(O)—; and $R^1$ is the aliphatic chain of caproleic acid. In some embodiments, $L^1$ is —C(O)—; and $R^1$ is the aliphatic chain of lauroleic acid. In some embodiments, $L^1$ is —C(O)—; and $R^1$ is the aliphatic chain of myristoleic acid. In some embodiments, $L^1$ is —C(O)—; and $R^1$ is the aliphatic chain of palmitoleic acid. In some embodiments, $L^1$ is —C(O)—; and $R^1$ is the aliphatic chain of sapienic acid. In some embodiments, $L^1$ is —C(O)—; and $R^1$ is the aliphatic chain of oleic acid. In some embodiments, $L^1$ is —C(O)—; and $R^1$ is the aliphatic chain of elaidic acid. In some embodiments, $L^1$ is —C(O)—; and $R^1$ is the aliphatic chain of vaccenic acid.

In some embodiments of any one of formulae (I), (II), (IIa), (III), and (IIIa), $L^1$ is —C(O)—; and $R^1$ is an aliphatic chain of a di-unsaturated fatty acid having 18 carbon atoms. In some embodiments, $L^1$ is —C(O)—; and $R^1$ is the aliphatic chain of linoleic acid.

In some embodiments of any one of formulae (I), (II), (IIa), (III), and (IIIa), $L^1$ is —C(O)—; and $R^1$ is an aliphatic chain of a poly-unsaturated fatty acid having 18 carbon atoms. In some embodiments, the poly-unsaturated fatty acid having 18 carbon atoms is selected from the group consisting of alpha-linolenic acid, gamma-linolenic acid, columbinic acid, pinolenic acid, and stearidonic acid. In some embodiments, $L^1$ is —C(O)—; and $R^1$ is the aliphatic chain of alpha-linolenic acid. In some embodiments, $L^1$ is —C(O)—; and $R^1$ is the aliphatic chain of gamma-linolenic acid. In some embodiments, $L^1$ is —C(O)—; and $R^1$ is the aliphatic chain of columbinic acid. In some embodiments, $L^1$ is —C(O)—; and $R^1$ is the aliphatic chain of pinolenic acid. In some embodiments, $L^1$ is —C(O)—; and $R^1$ is the aliphatic chain of stearidonic acid.

Exemplified compounds of formula (I) are listed in Table 1.

TABLE 1
Compounds of formula (I)
| No. | Structure | No. | Structure |
|---|---|---|---|
| 1.001 | 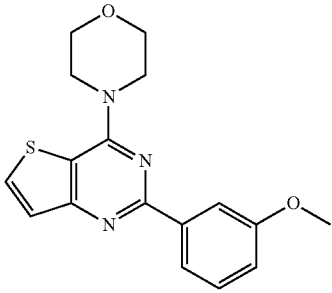 [SMILES: COc1cccc(-c2nc(N3CCOCC3)c3sccc3n2)c1] | 1.002 | 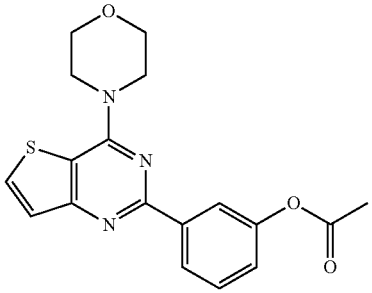 [SMILES: CC(=O)Oc1cccc(-c2nc(N3CCOCC3)c3sccc3n2)c1] |
| 1.003 | 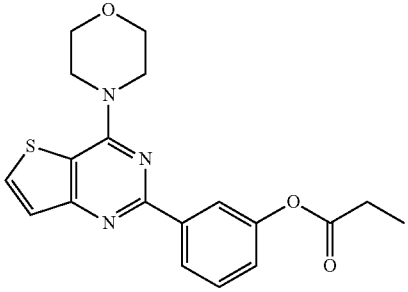 [SMILES: CCC(=O)Oc1cccc(-c2nc(N3CCOCC3)c3sccc3n2)c1] | 1.004 | 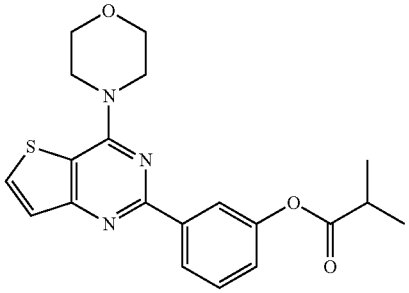 [SMILES: CC(C)C(=O)Oc1cccc(-c2nc(N3CCOCC3)c3sccc3n2)c1] |
| 1.005 | 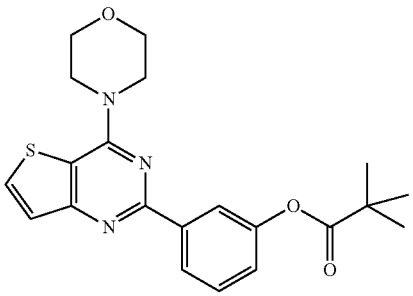 [SMILES: CC(C)(C)C(=O)Oc1cccc(-c2nc(N3CCOCC3)c3sccc3n2)c1] | 1.006 | 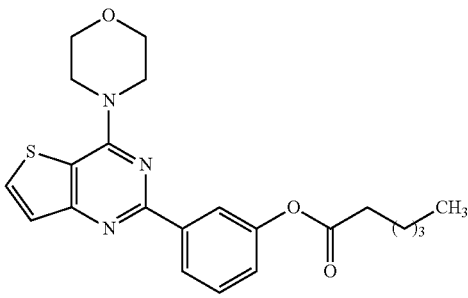 |
| 1.007 | 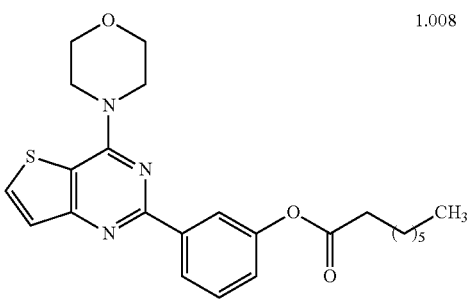 | 1.008 | 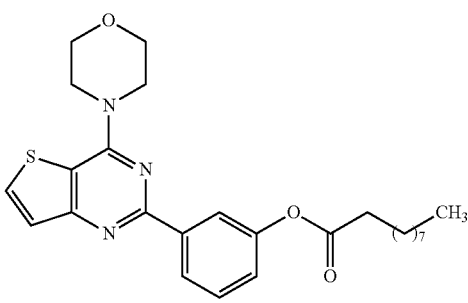 |
| 1.009 | 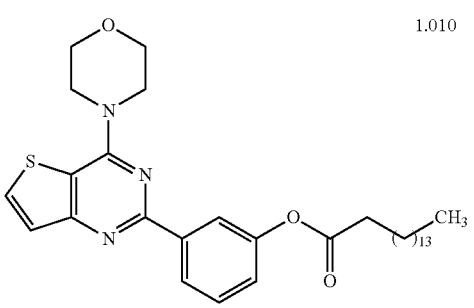 | 1.010 | 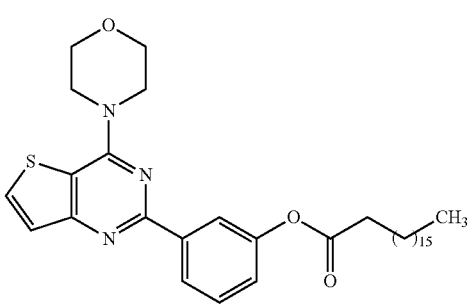 |

TABLE 1-continued

Compounds of formula (I)

| No. | Structure | No. | Structure |
|---|---|---|---|
| 1.011 | 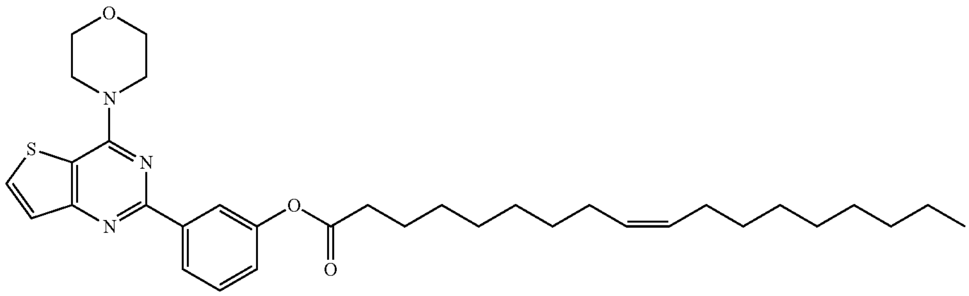 [SMILES: CCCCCCCC/C=C\CCCCCCCC(=O)Oc1cccc(-c2nc(N3CCOCC3)c3sccc3n2)c1] | | |
| 1.012 | 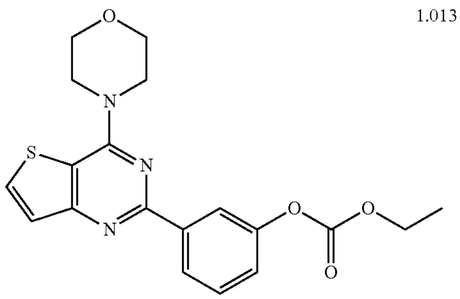 | 1.013 | 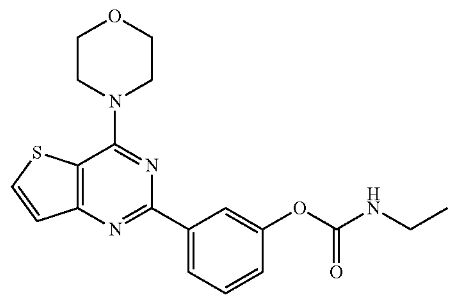 [SMILES: CCNC(=O)Oc1cccc(-c2nc(N3CCOCC3)c3sccc3n2)c1] |
| 1.014 | 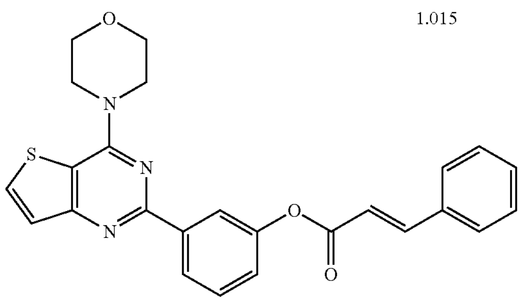 [SMILES: O=C(/C=C/c1ccccc1)Oc1cccc(-c2nc(N3CCOCC3)c3sccc3n2)c1] | 1.015 | 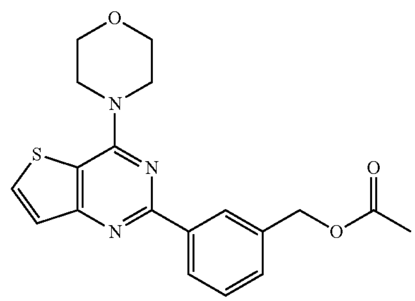 [SMILES: CC(=O)OCc1cccc(-c2nc(N3CCOCC3)c3sccc3n2)c1] |

In some embodiments, the compound of any one of formulae (I), (II), and (IIa) has the formula:

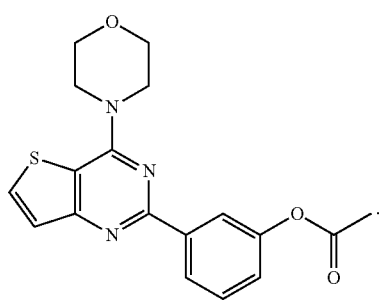

In some embodiments, the compound of any one of formulae (I), (III), and (IIIa) has the formula:

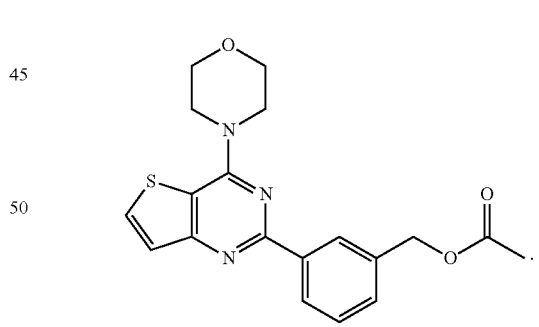

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess double bonds; tautomers, geometric isomers and individual isomers are encompassed within the scope of the present invention. The compounds of the present invention do not include those which are known in art to be too unstable to synthesize and/or isolate.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17 ($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

IV. Topical Formulation

In another aspect, the present invention provides a topical formulation for the treatment of vascular malformations. The topical formulation includes a) a compound having formula (I), and b) one or more topical excipients, wherein the compound having formula (I) is defined and described herein.

In some embodiments, the one or more topical excipients are selected from the group consisting of one or more solvents, one or more penetration enhancers, one or more gelling agents, and combinations thereof.

As will be appreciated, some excipients of the topical formulations described herein can possess multiple functions. For example, a given substance may act as both a solvent and a penetration enhancer. In some such cases, the function of a given substance can be considered singular, even though its properties may allow multiple functionality.

In some embodiments, the one or more solvents or penetration enhancers are selected from the group consisting of $C_{2-6}$ alcohol, a $C_{2-6}$ alkylene glycol, a di-($C_{2-6}$ alkylene) glycol, a polyethylene glycol, $C_{1-3}$ alkyl-$(OCH_2CH_2)_{1-5}$—OH, DMSO, a fatty alcohol, a fatty acid, and a fatty ester.

In some embodiments, the one or more solvents or penetration enhancers include $C_{2-6}$ alcohol. In some embodiments, the $C_{2-6}$ alcohol is selected from the group consisting of ethanol, propanol, isopropanol, n-butanol, isobutanol, 2-butanol, tert-butanol, and combinations thereof. In some embodiments, the $C_{2-6}$ alcohol is ethanol or isopropanol. In some embodiments, the $C_{2-6}$ alcohol is ethanol. In some embodiments, the one or more solvents or penetration enhancers include ethanol. In some embodiments, the one or more solvents or penetration enhancers do not include ethanol.

In some embodiments, the $C_{2-6}$ alcohol is present in an amount of 0% to about 80% by weight of the formulation. In some embodiments, the $C_{2-6}$ alcohol is absent. In some embodiments, ethanol is absent.

In some embodiments, the one or more solvents or penetration enhancers include a glycol selected from a $C_{2-6}$ alkylene glycol, a di-($C_{2-6}$ alkylene) glycol, a polyethylene glycol, or combinations thereof. In some embodiments, the $C_{2-6}$ alkylene glycol is propylene glycol. In some embodiments, the one or more solvents or penetration enhancers include a glycol selected from a di-($C_{2-6}$ alkylene) glycol, a polyethylene glycol, or combinations thereof. In some embodiments, the one or more solvents or penetration enhancers include di-($C_{2-6}$ alkylene) glycol and a polyethylene glycol. In some embodiments, the $C_{2-6}$ alkylene glycol is propylene glycol. In some embodiments, the di-($C_{2-6}$ alkylene) glycol is dipropylene glycol. In some embodiments, the polyethylene glycol is PEG200, PEG300, PEG400, PEG600, or PEG900. In some embodiments, the one or more solvents or penetration enhancers include propylene glycol, dipropylene glycol, PEG200, PEG300, PEG400, PEG600, PEG900, or combinations thereof. In some embodiments, the one or more solvents or penetration enhancers include dipropylene glycol, PEG200, PEG300, PEG400, PEG600, PEG900, or combinations thereof. In some embodiments, the one or more solvents or penetration enhancers include dipropylene glycol. In some embodiments, the one or more solvents or penetration enhancers include dipropylene glycol and PEG400.

In some embodiments, the glycol is present in an amount of about 5% to about 60% by weight of the base formulation. In some embodiments, the glycol is present in an amount of from 5% to 50%, from 5% to 40%, from 5% to 30%, from 5% to 20%, from 5% to 15%, from 20% to 60%, from 20% to 50%, from 20% to 40%, from 30% to 60%, from 30% to 50%, from 30% to 40%, from 40% to 60%, from 40% to 50%, or from 50% to 60% by weight of the base formulation. In some embodiments, the glycol is present in an amount of about 5% by weight of the base formulation. In some embodiments, the glycol is present in an amount of about 10% by weight of the base formulation. In some embodiments, the glycol is present in an amount of about 20% by weight of the base formulation. In some embodiments, the glycol is present in an amount of about 30% by weight of the base formulation. In some embodiments, the glycol is present in an amount of about 35% by weight of the base formulation. In some embodiments, the glycol is present in an amount of about 40% by weight of the base formulation. In some embodiments, the glycol is dipropylene glycol, PEG400, or combination thereof. In some embodiments, the glycol is dipropylene glycol. In some embodiments, the glycol is PEG400. In some embodiments, the glycol is dipropylene glycol and PEG400. In some embodiments, dipropylene glycol and/or PEG400 are present in an amount of about 10% by weight of the base formulation. In some embodiments, dipropylene glycol and/or PEG400 are present in an amount of about 20% by weight of the base formulation. In some embodiments, dipropylene glycol and/or PEG400 are present in an amount of about 30% by weight of the base formulation. In some embodiments, dipropylene glycol and/or PEG400 are present in an amount of about 35% by weight of the base formulation. In some embodiments, dipropylene glycol and/or PEG400 are present in an amount of about 40% by weight of the base formulation. In some embodiments, dipropylene glycol is present in an amount of about 5% by weight of the base formulation and PEG400 is present in an amount of about 30% by weight of the base formulation. In some embodiments, dipropylene glycol is present in an amount of about 5% by weight of the base formulation and PEG400 is present in an amount of about 35% by weight of the base formulation. In some embodiments, dipropylene glycol is present in an amount of about 5% by weight of the base formulation and PEG400 is present in an amount of about 40% by weight of the base formulation.

In some embodiments, the one or more solvents or penetration enhancers include $C_{1-3}$ alkyl-$(OCH_2CH_2)_{1-5}$—OH. In some embodiments, the $C_{1-3}$ alkyl-$(OCH_2CH_2)_{1-5}$—OH is 2-(2-ethoxyethoxy)ethanol (i.e., sold under the name Transcutol®). In some embodiments, the one or more solvents or penetration enhancers include 2-(2-ethoxyethoxy)ethanol.

In some embodiments, 2-(2-ethoxyethoxy)ethanol is present in an amount of about 1% to about 50% by weight of the base formulation. In some embodiments, 2-(2-ethoxyethoxy)ethanol is present in an amount of from 5% to 50%, from 10% to 50%, from 10% to 40%, or form 10% to 30% by weight of the base formulation. In some embodiments, 2-(2-ethoxyethoxy)ethanol is present in an amount of about 20% by weight of the base formulation. In some embodiments, 2-(2-ethoxyethoxy)ethanol is present in an amount of about 25% by weight of the base formulation.

In some embodiments, the one or more solvents or penetration enhancers include includes a fatty alcohol. As used herein, the term "fatty alcohol refers to an aliphatic alcohol that is saturated or unsaturated. In some embodiments, the fatty alcohol is in a mixture of different fatty alcohols. In some embodiments, the fatty alcohol has between about 12-20, 14-20, 12-18, 14-18, or 16-18 carbons on average. Suitable fatty alcohols include, but are not limited to, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, or mixtures thereof. In some embodiments, the solvent or penetration enhancer includes one or more fatty alcohols selected from capric alcohol, lauryl alcohol, myristyl alcohol, cetyl alcohol, palmitoleyl alcohol, stearyl alcohol, oleyl alcohol, arachidyl alcohol, heneicosyl alcohol, behenyl alcohol, erucyl alcohol, and lignoceryl alcohol. In some embodiments, the one or more solvents or penetration enhancers include oleyl alcohol.

In some embodiments, fatty alcohol is present in an amount of about 0.5% to about 20% by weight of the base formulation. In some embodiments, fatty alcohol is present in an amount of from 1% to 20%, from 1% to 15%, 1% to 10%, from 5% to 20%, from 5% to 15%, or from 5% to 10% by weight of the base formulation. In some embodiments, fatty alcohol is present in an amount of about 10% by weight of the base formulation. In some embodiments, oleyl alcohol is present in an amount of from 0.5% to 20%, from 1% to 20%, from 1% to 15%, 1% to 10%, from 5% to 20%, from 5% to 15%, or from 5% to 10% by weight of the base formulation. In some embodiments, oleyl alcohol is present in an amount of about 10% by weight of the base formulation.

In some embodiments, the one or more solvents or penetration enhancers include a fatty acid. As used herein, the term "fatty acid refers to an aliphatic acid that is straight or branched and saturated or unsaturated. In some embodiments, the fatty acid is in a mixture of different fatty acids. In some embodiments, the fatty acid has between about 8 to about 30 carbons on average. In some embodiments, the fatty acid has about 12-20, 14-20, 12-18, 14-18, or 16-18 carbons on average. Suitable fatty acids include, but are not limited to, capric acid, neodecanoic acid, undecylic acid, lauric acid, tridecylic acid, myristic acid, pentadecylic acid, palmitic acid, margaric acid, stearic acid, isostearic acid, nonadecylic acid, arachidic acid, heneicosylic acid, behenic acid, tricosylic acid, lignoceric acid, caproleic acid, lauroleic acid, myristoleic acid, palmitoleic acid, sapienic acid, oleic acid, elaidic acid, vaccenic acid, gadoleic acid, eicosenoic acid, erucic acid, brassidic acid, nervonic acid, linoleic acid, eicosadienoic acid, docosadienoic acid, alpha-linolenic acid, gamma-linolenic acid, columbinic acid, pinolenic acid, alpha-eleostearic acid, beta-eleostearic acid, mead acid, dihomo-γ-linolenic acid, eicosatrienoic acid, stearidonic acid, arachidonic acid, eicosapentaenoic acid, docosapentaenoic acid, docosahexaenoic acid, or mixtures thereof. In some embodiments, the fatty acid is selected from capric acid, neodecanoic acid, lauric acid, myristic acid, palmitic acid, stearic acid, isostearic acid, behenic acid, caproleic acid, lauroleic acid, myristoleic acid, palmitoleic acid, oleic acid, erucic acid, linoleic acid, linolenic acid, hydroxystearic acid, 12-hydroxystearic acid, cetostearic acid, isostearic acid, sesquioleic acid, sesqui-9-octadecanoic acid, sesquisooctadecanoic acid, behenic acid, isobehenic acid, arachidonic acid, and combinations thereof. In some embodiments, the one or more solvents or penetration enhancers include one or more fatty acids selected from neodecanoic acid, isostearic acid, caproleic acid, lauroleic acid, myristoleic acid, palmitoleic acid, oleic acid, linoleic acid, and linolenic acid. In some embodiments, the one or more solvents or penetration enhancers include one or more fatty acids selected from neodecanoic acid, isostearic acid, and oleic acid. In some embodiments, the one or more solvents or penetration enhancers include neodecanoic acid. In some embodiments, the one or more solvents or penetration enhancers include isostearic acid. In some embodiments, the one or more solvents or penetration enhancers include oleic acid. In some embodiments, the one or more solvents or penetration enhancers include linoleic acid. In some embodiments, the one or more solvents or penetration enhancers include linolenic acid.

In some embodiments, the fatty acid is present in an amount of about 0.5% to about 15% by weight of the base formulation. In some embodiments, fatty acid is present in an amount of from 1% to 15%, from 2% to 15%, from 3% to 15%, from 2% to 15%, from 2% to 10%, or from 5% to 15% by weight of the base formulation. In some embodiments, oleic acid is present in an amount of about 0.5% to about 15% by weight of the base formulation. In some embodiments, oleic acid is present in an amount of about 2% by weight of the base formulation. In some embodiments, oleic acid is present in an amount of about 5% by weight of the base formulation. In some embodiments, oleic acid is present in an amount of about 10% by weight of the base formulation.

In some embodiments, the one or more solvents or penetration enhancers include a fatty ester. In some embodiments, the fatty ester is a glyceryl fatty ester, ethylene glycol monoester and diester of a fatty acid, propylene glycol monoester and diester of a fatty acid, a sorbitan ester, a $C_{1-6}$ alkyl ester of a fatty acid, di-($C_{1-6}$ alkyl) ester of adipic acid, sebacic acid, or combinations thereof.

In some embodiments, the fatty ester is a glyceride. In some embodiments, the glyceride is monoglycerides, diglycerides, or triglycerides. The glycerides may be optionally substituted with sulfonic acid groups, or pharmaceutically acceptable salts thereof. Suitable fatty acids for deriving glycerides of fatty acids include, but are not limited to, those described herein. In some embodiments, the glyceride is a mono-glyceride of a fatty acid having 12 to 18 carbon atoms. In some embodiments, the glyceride is glyceryl stearate. In some embodiments, the glyceride is glycerol monolaurate, glycerol monocaprate, glycerol monocaprylate, glycerol monostearate, or glycerol monooleate. In some embodiments, the glyceride is glycerol monooleate. In some embodiments, the glyceride is a triglyceride of a fatty acid having 12 to 18 carbon atoms.

In some embodiments, the one or more solvents or penetration enhancers include a glyceride. In some embodiments, the one or more solvents or penetration enhancers include a monoglyceride. In some embodiments, the one or more solvents or penetration enhancers include glycerol monooleate.

In some embodiments, the fatty ester is an ethylene glycol monoester of a fatty acid, a propylene glycol monoester of a fatty acid, or a $C_{1-6}$ alkyl ester of a fatty acid. In some embodiments, the fatty ester is an ethylene glycol monoester, a propylene glycol monoester, or a $C_{1-4}$ alkyl ester of a fatty acid. Suitable fatty acids for deriving any one of the ethylene glycol monoester, propylene glycol monoester, and the $C_{1-4}$ alkyl ester of fatty acids include, but are not limited to, those described herein. In some embodiments, the fatty ester is an ethylene glycol monoester, a propylene glycol monoester, or a $C_{1-4}$ alkyl ester of a fatty acid having 12 to 18 carbon atoms. Non-limiting examples of esters of a fatty acid include a laurate, a myristate, a palmitate, a stearate, or an oleate. In some embodiments, the fatty ester is methyl laurate. In some embodiments, the fatty ester is isopropyl myristate. In some embodiments, the fatty ester is isopropyl palmitate. In some embodiments, the fatty ester is ethylene glycol monostearate. In some embodiments, the fatty ester is propylene glycol monostearate. In some embodiments, the fatty ester is ethylene glycol monooleate. In some embodiments, the fatty ester is propylene glycol monooleate.

In some embodiments, the fatty ester is a sorbitan ester. Suitable fatty acids for deriving the sorbitan esters include, but are not limited to, those described herein. Suitable sorbitan esters include, but are not limited to, the Span™ series (available from Uniqema), which includes products sold under the names Span™ 20 (Sorbitan monolaurate), 40 (Sorbitan monopalmitate), 60 (sorbitan monostearate), 65 (sorbitan tristearate), 80 (sorbitan monooleate), and 85 (sorbitan trioleate).

In some embodiments, the fatty ester is a di-($C_{1-4}$ alkyl) ester of adipic acid (i.e., an adipate) or di-($C_{1-4}$ alkyl) ester of sebacic acid (i.e., a sebacate). In some embodiments, the fatty ester is diisopropyl adipate. In some embodiments, the fatty ester is diethyl sebacate.

In some embodiments, the one or more solvents or penetration enhancers are selected from the group consisting of a di-($C_{2-6}$ alkylene) glycol, a polyethylene glycol, $C_{1-3}$ alkyl-$(OCH_2CH_2)_{1-5}$—OH, DMSO, a fatty alcohol, and a fatty acid. In some embodiments, the one or more solvents or penetration enhancers are selected from the group consisting of DMSO, oleic acid, oleyl alcohol, 2-(2-ethoxyethoxy)ethanol, dipropylene glycol, and PEG400. In some embodiments, the one or more solvents or penetration enhancers are selected from the group consisting of DMSO, oleic acid, 2-(2-ethoxyethoxy)ethanol, dipropylene glycol, and PEG400. In some embodiments, the one or more solvents or penetration enhancers are selected from the group consisting of DMSO, oleic acid, 2-(2-ethoxyethoxy)ethanol, dipropylene glycol, and PEG400.

In some embodiments, the one or more solvents or penetration enhancers do not include DMSO. In some embodiments, the one or more solvents or penetration enhancers include DMSO. In some embodiments, DMSO is present in an amount of less than 50%, less than 40%, less than 30%, or less than 20% by weight of the base formulation. In some embodiments, DMSO is present in an amount of from 30% to 50%, from 20% to 50%, from 10% to 50%, from 30% to 40%, from 20% to 40%, from 10% to 40%, from 20% to 30%, from 10% to 30%, or from 10% to 20% by weight of the base formulation. In some embodiments, DMSO is present in an amount of from 30% to 50%, from 20% to 50%, from 30% to 40%, from 20% to 40%, or from 20% to 30% by weight of the base formulation. In some embodiments, DMSO is present in an amount of from 20% to 40% or from 20% to 30% by weight of the base formulation. In some embodiments, DMSO is present in an amount of about 30% by weight of the base formulation.

Polymer thickeners (gelling agents) that may be used in the invention include those known to one skilled in the art, such as hydrophilic and hydroalcoholic gelling agents frequently used in the cosmetic and pharmaceutical industries. In some embodiments, the one or more gelling agents are carbomers (sold under the name Carbopol®), carboxymethyl cellulose, ethylcellulose, gelatin, hydroxyethyl cellulose, hydroxypropyl cellulose, magnesium aluminum silicate (sold under the name Veegum®), methylcellulose, poloxamers (sold under the name Pluronic®), polyvinyl alcohol, sodium alginate, tragacanth, xanthan gum, or combinations thereof. In some embodiments, the one or more gelling agents include hydroxypropyl cellulose. In some embodiments, the hydroxypropyl cellulose has a molecular weight selected from the group consisting of 40,000 Da, 80,000 Da, 100,000 Da, 140,000 Da, 180,000 Da, 280,000 Da, 370,000 Da, 700,000 Da, 850,000 Da, 1,000,000 Da, 1,150,000 Da, and 2,500,000 Da. In some embodiments, the hydroxypropyl cellulose has the molecular weight selected from the group consisting of 140,000 Da, 180,000 Da, 280,000 Da, 370,000 Da, 700,000 Da, 850,000 Da, 1,000,000 Da, and 1,150,000 Da. In some embodiments, the hydroxypropyl cellulose has the molecular weight selected from the group consisting of 700,000 Da, 850,000 Da, 1,000,000 Da, and 1,150,000 Da.

The hydroxypropyl cellulose (HPC) as described herein include products sold under the names Nisso SSL, Nisso SL, Nisso L, Nisso LM, Nisso LMM, Nisso M, Nisso H, Nisso VH, Klucel™ ELF, Klucel™ EF, Klucel™ LF, Klucel™ JF, Klucel™ GF, Klucel™ MF, and Klucel™ HF. Nisso SSL has an average molecular weight of 40,000 Da; Nisso SL has an average molecular weight of 100,000 Da; Nisso L has an average molecular weight of 140,000 Da; Nisso LM has an average molecular weight of 180,000 Da; Nisso LMM has an average molecular weight of 280,000 Da; Nisso M has an average molecular weight of 700,000 Da; Nisso H has an average molecular weight of 1,000,000 Da; and Nisso VH has an average molecular weight of 2,500,000 Da. Suitable particle sizes of Nisso HPC (i.e., Nisso SSL, Nisso SL, Nisso L, Nisso LM, Nisso LMM, Nisso M, Nisso H, and Nisso VH) in the topical formulation include regular powder (40 mesh), fine powder (100 mesh), and super fine powder (300 mesh). See Technical date sheets of Nisso HPCs, the entirety of which is incorporated herein by reference for all purpose. In some embodiments, the hydroxypropyl cellulose is Nisso H. Klucel™ ELF has an average molecular weight of 40,000 Da; Klucel™ EF has an average molecular weight of 80,000 Da; Klucel™ LF has an average molecular weight of 95,000 Da; Klucel™ JF has an average molecular weight of 140,000 Da; Klucel™ GF has an average molecular weight of 370,000 Da; Klucel™ MF has an average molecular weight of 850,000 Da; and Klucel™ HF has an average molecular weight of 1,150,000 Da. Suitable particle sizes of Klucel™ HPC in the topical formulation include regular grade and fine grade. See Technical date sheets of Klucel™ HPC products, the entirety of which is incorporated herein by reference for all purpose. In some embodiments, the hydroxypropyl cellulose is Klucel™ HF.

When the one or more gelling agents are present, in some embodiments, the topical formulation has a viscosity of 5,000 to 100,000 cP. When the one or more gelling agents are present, in some embodiments, the topical formulation has a viscosity of 5,000 to 50,000 cP. When the one or more gelling agents are present, in some embodiments, the topical formulation has a viscosity of 5,000 to 15,000 cP. When the hydroxypropyl cellulose is present, in some embodiments, the topical formulation has a viscosity of 5,000 to 100,000 cP. When the hydroxypropyl cellulose is present, in some embodiments, the topical formulation has a viscosity of 5,000 to 50,000 cP. When the hydroxypropyl cellulose is present, in some embodiments, the topical formulation has a viscosity of 5,000 to 15,000 cP.

In some embodiments, the one or more gelling agents are present in an amount of from about 0.5% to about 30% by weight of the base formulation, while the topical formulation has a viscosity of 5,000 to 100,000 cP. In some embodiments, the one or more gelling agents are present in an amount of from about 0.5% to about 30% by weight of the base formulation, while the topical formulation has a viscosity of 5,000 to 50,000 cP. In some embodiments, the one or more gelling agents are present in an amount of from about 0.5% to about 30% by weight of the base formulation, while the topical formulation has a viscosity of 5,000 to 15,000 cP. In some embodiments, the hydroxypropyl cellulose is present in an amount of from about 0.5% to about 5%, from about 5% to about 10%, from about 10% to about 20%, or from about 20% to about 30% by weight of the base formulation, while the topical formulation has a viscosity of 5,000 to 100,000 cP. When a hydroxypropyl cellulose having an average molecular weight of less than 700,000 Da is used, in some embodiments, the hydroxypropyl cellulose is present in an amount of about 5% to about 30% by weight of the base formulation, while the topical formulation has a viscosity of 5,000 to 100,000 cP. In some embodiments, the hydroxypropyl cellulose is present in an amount of from 0.5% to 4%, from 0.5% to 3%, from 0.5% to 2%, from 1% to 5%, from 1% to 4%, from 1% to 3%, from 1% to 2%, or from 2% to 5% by weight of the base formulation, while the topical formulation has a viscosity of 5000 to 15000 cP. In some embodiments, the hydroxypropyl cellulose having an average molecular weight selected from 700,000 Da and 1,150,000 Da is present in an amount of about 2% by weight of the base formulation. In some embodiments, the hydroxypropyl cellulose having an average molecular weight selected from 700,000 Da and 1,150,000 Da is present in an amount of about 1% by weight of the base formulation.

In some embodiments, the topical formulation includes a stabilizer. The stabilizer as described herein include an agent or a buffer that stabilizes the formulation. Suitable buffering agents for use with the invention include, but are not limited to, acetate buffers, citrate buffers, phosphate buffers, lactic acid buffers, and borate buffers. Suitable agent to stabilize the formulation include an antioxidant. Suitable antioxidant agents for use with the invention include, but are not limited to, citric acid, butylated hydroxytoluene (BHT), butylated hydroxyanisole (BHA), tocophenerol, Coenzyme Q10 (CoQ10), idebenone, lycopene, ascorbic acid, epigallocatechin 3-gallate (EGCG), and silymarin.

In some embodiments, the topical formulation is substantially free of oxygen.

In some embodiments, the compound of formula (I) or a pharmaceutically acceptable salt thereof is in an anhydrous form. In some embodiments, the compound of formula (I) or a pharmaceutically acceptable salt thereof is in a hydrous form. In some embodiments, the compound of formula (I) or a pharmaceutically acceptable salt thereof is a mixture of an anhydrous and hydrate forms.

In some embodiments, the compound of formula (I) used in preparing the topical formulation of the present invention is in a salt-free form.

In some embodiments, the compound of formula (I) is present in an amount of from 0.05% to 15%, from 0.5% to 12%, from 0.5% to 10%, from 1% to 10%, from 2% to 10%, from 5% to 10%, or from 2 to 5% by weight of the base formulation on a salt-free and anhydrous basis. In some embodiments, the compound of formula (I) is present in an amount of about 1% by weight of the base formulation on a salt-free and anhydrous basis. In some embodiments, the compound of formula (I) is present in an amount of about 5% by weight of the base formulation on a salt-free and anhydrous basis. In some embodiments, the compound of formula (I) is present in an amount of about 10% by weight of the base formulation on a and anhydrous basis. In some embodiments, the compound of formula (I) is present at a saturated concentration in the topical formulation.

In some embodiments, ethanol is absent in the topical formulation. In some embodiments, DMSO is absent in the topical formulation.

In some embodiments, the topical formulation (FI) comprises:
a) from 0.5% to 10% by weight of the compound of formula (I) or a hydrate, solvate, and/or pharmaceutically acceptable salt thereof, on a salt-free and anhydrous basis;
b) from 50% to 90% by weight of a $C_{2-6}$ alcohol;
c) from 1% to 150% by weight of a fatty acid, a fatty alcohol, a fatty ester, or combinations thereof;
d) from 5% to 15% by weight of a $C_{2-6}$ alkylene glycol, a di-($C_{2-6}$ alkylene) glycol, a polyethylene glycol, or combinations thereof; and
e) from 0% to 5% by weight of hydoxypropyl cellulose,
wherein the total weight of the one or more topical excipients from b) to d) is 100%.

In some embodiments, the topical formulation (FI-1) comprises:
a) from 0.5% to 10% by weight of the compound of formula (I) or a hydrate, solvate, and/or pharmaceutically acceptable salt thereof, on a salt-free and anhydrous basis;
b) from 60% to 90% by weight of a $C_{2-6}$ alcohol;
c) from 1% to 15% by weight of a fatty acid; and
d) from 5% to 15% by weight of a di-($C_{2-6}$ alkylene) glycol,
wherein the total weight of the one or more topical excipients from b) to d) is 100%.

In some embodiments, the topical formulation (FI-2) comprises:
a) from 0.5% to 10% by weight of the compound of formula (I) or a hydrate, solvate, and/or pharmaceutically acceptable salt thereof, on a salt-free and anhydrous basis;
b) from 60% to 90% by weight of a $C_{2-6}$ alcohol;
c) from 1% to 15% by weight of a fatty acid;
d) from 5% to 15% by weight of a di-($C_{2-6}$ alkylene) glycol; and
e) from 1% to 3% by weight of hydoxypropyl cellulose,
wherein the total weight of the one or more topical excipients from b) to d) is 100%.

In some embodiments, the topical formulation (FI-3) comprises:
a) from 0.5% to 10% by weight of the compound of formula (I) or a hydrate, solvate, and/or pharmaceutically acceptable salt thereof, on a salt-free and anhydrous basis;
b) from 60% to 90% by weight of a $C_{2-6}$ alcohol;
c) from 1% to 15% by weight of a fatty alcohol;
d) from 5% to 15% by weight of a di-($C_{2-6}$ alkylene) glycol; and
e) from 1% to 3% by weight of hydoxypropyl cellulose,
wherein the total weight of the one or more topical excipients from b) to d) is 100%.

In some embodiments, the topical formulation (FI-4) comprises:
a) from 0.5% to 10% by weight of the compound of formula (I) or a hydrate, solvate, and/or pharmaceutically acceptable salt thereof, on a salt-free and anhydrous basis;
b) from 60% to 90% by weight of a $C_{2-6}$ alcohol;
c) from 1% to 15% by weight of a fatty ester;
d) from 5% to 15% by weight of a di-($C_{2-6}$ alkylene) glycol; and
e) from 1% to 3% by weight of hydoxypropyl cellulose,
wherein the total weight of the one or more topical excipients from b) to d) is 100%.

In some embodiments of any one of the above formulations (FI), (FI-1), (FI-2), (FI-3), and (FI-4), the $C_{2-6}$ alcohol is ethanol; the fatty acid is oleic acid; the fatty alcohol is oleyl alcohol; the fatty ester is glycerol monooleate; the di-($C_{2-6}$ alkylene) glycol is dipropylene glycol; and the hydoxypropyl cellulose is the product sold under the name Klucel™ HF.

In some embodiments, the topical formulation (FII) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 2% to 15% by weight of a fatty acid, a fatty alcohol, a fatty ester, or combinations thereof;
d) from 10% to 30% by weight of $C_{1-3}$ alkyl-$(OCH_2CH_2)_{1-5}$—OH;
e) from 30% to 50% by weight of a $C_{2-6}$ alkylene glycol, a di-($C_{2-6}$ alkylene) glycol, a polyethylene glycol, or combinations thereof; and
f) from 0.5% to 5% by weight of hydoxypropyl cellulose,
wherein the total weight of the one or more topical excipients from b) to e) is 100%.

In some embodiments, the topical formulation (FII-1) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 5% to 15% by weight of a fatty acid, a fatty alcohol, a fatty ester, or combinations thereof;
d) from 10% to 30% by weight of $C_{1-3}$ alkyl-$(OCH_2CH_2)_{1-5}$—OH;
e) from 30% to 50% by weight of a $C_{2-6}$ alkylene glycol, a di-($C_{2-6}$ alkylene) glycol, a polyethylene glycol, or combinations thereof; and
f) from 0.5% to 5% by weight of hydoxypropyl cellulose, wherein the total weight of the one or more topical excipients from b) to e) is 100%.

In some embodiments, the topical formulation (FII-2) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 5% to 15% by weight of a fatty acid;
d) from 10% to 30% by weight of $C_{1-3}$ alkyl-$(OCH_2CH_2)_{1-5}$—OH;
e) from 30% to 50% by weight of a di-($C_{2-6}$ alkylene) glycol; and
f) from 0.5% to 5% by weight of hydoxypropyl cellulose, wherein the total weight of the one or more topical excipients from b) to e) is 100%.

In some embodiments, the topical formulation (FII-3) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 5% to 15% by weight of a fatty alcohol;
d) from 10% to 30% by weight of $C_{1-3}$ alkyl-$(OCH_2CH_2)_{1-5}$—OH;
e) from 30% to 50% by weight of a di-($C_{2-6}$ alkylene) glycol; and
f) from 0.5% to 5% by weight of hydoxypropyl cellulose, wherein the total weight of the one or more topical excipients from b) to e) is 100%.

In some embodiments, the topical formulation (FII-4) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 2% to 15% by weight of a fatty acid or fatty alcohol;
d) from 10% to 30% by weight of $C_{1-3}$ alkyl-$(OCH_2CH_2)_{1-5}$—OH;
e) from 30% to 50% by weight of a di-($C_{2-6}$ alkylene) glycol and a polyethylene glycol; and
f) from 0.5% to 5% by weight of hydoxypropyl cellulose, wherein the total weight of the one or more topical excipients from b) to e) is 100%.

In some embodiments, the topical formulation (FII-5) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 2% to 15% by weight of a fatty acid or fatty alcohol;
d) from 10% to 30% by weight of $C_{1-3}$ alkyl-$(OCH_2CH_2)_{1-5}$—OH;
e) from 3% to 10% by weight of a di-($C_{2-6}$ alkylene) glycol;
f) from 25% to 45% by weight of a polyethylene glycol; and
g) from 0.5% to 5% by weight of hydoxypropyl cellulose, wherein the total weight of the one or more topical excipients from b) to f) is 100%.

In some embodiments, the topical formulation (FII-6) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 2% to 15% by weight of a fatty acid or fatty alcohol;
d) from 10% to 30% by weight of $C_{1-3}$ alkyl-$(OCH_2CH_2)_{1-5}$—OH;
e) from 3% to 5% by weight of a di-($C_{2-6}$ alkylene) glycol;
f) from 25% to 45% by weight of a polyethylene glycol; and
g) from 0.5% to 5% by weight of hydoxypropyl cellulose, wherein the total weight of the one or more topical excipients from b) to f) is 100%.

In some embodiments of any one of formulations (FII) to (FII-6), the fatty acid is oleic acid; the fatty alcohol is oleyl alcohol; the fatty ester is glycerol monooleate; $C_{1-3}$ alkyl-$(OCH_2CH_2)_{1-5}$—OH is 2-(2-ethoxyethoxy)ethanol (sold under the name Transcutol®), the di-($C_{2-6}$ alkylene) glycol is dipropylene glycol; a polyethylene glycol is PEG400; and the hydoxypropyl cellulose is the product sold under the name Klucel™ HF.

In some embodiments, the topical formulation (FII-7) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 5% to 15% by weight of oleic acid;
d) from 10% to 30% by weight of 2-(2-ethoxyethoxy)ethanol;
e) from 30% to 50% by weight of dipropylene glycol; and
f) from 0.5% to 5% by weight of hydoxypropyl cellulose, wherein the total weight of the one or more topical excipients from b) to e) is 100%.

In some embodiments, the topical formulation (FII-8) comprises:
a) about 10% by weight of the compound of formula (I) or a hydrate, solvate, and/or pharmaceutically acceptable salt thereof, on a salt-free and anhydrous basis;
b) about 30% by weight of DMSO;
c) about 10% by weight of oleic acid;
d) about 20% by weight of 2-(2-ethoxyethoxy)ethanol;
e) about 40% by weight of dipropylene glycol; and
f) about 2% by weight of hydoxypropyl cellulose, wherein the total weight of the one or more topical excipients from b) to e) is 100%.

In some embodiments, the topical formulation (FII-9) comprises:
a) about 10% by weight of 3-(4-morpholinothieno[3,2-d]pyrimidin-2-yl)phenyl acetate or a hydrate, solvate, and/or pharmaceutically acceptable salt thereof, on a salt-free and anhydrous basis;
b) about 30% by weight of DMSO;
c) about 10% by weight of oleic acid;
d) about 20% by weight of 2-(2-ethoxyethoxy)ethanol;
e) about 40% by weight of dipropylene glycol; and
f) about 2% by weight of hydoxypropyl cellulose,
wherein the total weight of the one or more topical excipients from b) to e) is 100%.

In some embodiments, the topical formulation (FII-10) comprises:
a) about 10% by weight of the compound of formula (I) or a hydrate, solvate, and/or pharmaceutically acceptable salt thereof, on a salt-free and anhydrous basis;
b) about 30% by weight of DMSO;
c) about 10% by weight of oleic acid;
d) about 20% by weight of 2-(2-ethoxyethoxy)ethanol;
e) about 40% by weight of dipropylene glycol; and
f) about 1% by weight of hydoxypropyl cellulose,
wherein the total weight of the one or more topical excipients from b) to e) is 100%.

In some embodiments, the topical formulation (FII-11) comprises:
a) about 10% by weight of 3-(4-morpholinothieno[3,2-d]pyrimidin-2-yl)phenyl acetate or a hydrate, solvate, and/or pharmaceutically acceptable salt thereof, on a salt-free and anhydrous basis;
b) about 30% by weight of DMSO;
c) about 10% by weight of oleic acid;
d) about 20% by weight of 2-(2-ethoxyethoxy)ethanol;
e) about 40% by weight of dipropylene glycol; and
f) about 1% by weight of hydoxypropyl cellulose,
wherein the total weight of the one or more topical excipients from b) to e) is 100%.

In some embodiments, the topical formulation (FII-12) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 2% to 15% by weight of oleic acid or oleyl alcohol;
d) from 10% to 30% by weight of 2-(2-ethoxyethoxy)ethanol;
e) from 3% to 5% by weight of dipropylene glycol;
f) from 25% to 45% by weight of PEG400; and
g) from 0.5% to 5% by weight of hydoxypropyl cellulose,
wherein the total weight of the one or more topical excipients from b) to f) is 100%.

In some embodiments, the topical formulation (FII-13) comprises:
a) about 10% by weight of the compound of formula (I) or a hydrate, solvate, and/or pharmaceutically acceptable salt thereof, on a salt-free and anhydrous basis;
b) about 30% by weight of DMSO;
c) about 10% by weight of oleyl alcohol;
d) about 20% by weight of 2-(2-ethoxyethoxy)ethanol;
e) about 5% by weight of dipropylene glycol;
f) about 35% by weight of PEG400; and
g) about 2% by weight of hydoxypropyl cellulose,
wherein the total weight of the one or more topical excipients from b) to f) is 100%.

In some embodiments, the topical formulation (FII-14) comprises:
a) about 10% by weight of 3-(4-morpholinothieno[3,2-d]pyrimidin-2-yl)phenyl acetate or a hydrate, solvate, and/or pharmaceutically acceptable salt thereof, on a salt-free and anhydrous basis;
b) about 30% by weight of DMSO;
c) about 10% by weight of oleyl alcohol;
d) about 20% by weight of 2-(2-ethoxyethoxy)ethanol;
e) about 5% by weight of dipropylene glycol;
f) about 35% by weight of PEG400; and
g) about 2% by weight of hydoxypropyl cellulose,
wherein the total weight of the one or more topical excipients from b) to f) is 100%.

In some embodiments, the topical formulation (FII-15) comprises:
a) about 10% by weight of the compound of formula (I) or a hydrate, solvate, and/or pharmaceutically acceptable salt thereof, on a salt-free and anhydrous basis;
b) about 33% by weight of DMSO;
c) about 2% by weight of oleic acid;
d) about 22% by weight of 2-(2-ethoxyethoxy)ethanol;
e) about 5% by weight of dipropylene glycol;
f) about 38% by weight of PEG400; and
g) about 2% by weight of hydoxypropyl cellulose,
wherein the total weight of the one or more topical excipients from b) to f) is 100%.

In some embodiments, the topical formulation (FII-16) comprises:
a) about 10% by weight of 3-(4-morpholinothieno[3,2-d]pyrimidin-2-yl)phenyl acetate or a hydrate, solvate, and/or pharmaceutically acceptable salt thereof, on a salt-free and anhydrous basis;
b) about 30% by weight of DMSO;
c) about 10% by weight of oleyl alcohol;
d) about 20% by weight of 2-(2-ethoxyethoxy)ethanol;
e) about 5% by weight of dipropylene glycol;
f) from 35% by weight of PEG400; and
g) about 2% by weight of hydoxypropyl cellulose,
wherein the total weight of the one or more topical excipients from b) to f) is 100%.

In some embodiments, the topical formulation (FII-17) comprises:
a) about 10% by weight of 3-(4-morpholinothieno[3,2-d]pyrimidin-2-yl)phenyl acetate or a hydrate, solvate, and/or pharmaceutically acceptable salt thereof, on a salt-free and anhydrous basis;
b) about 33% by weight of DMSO;
c) about 2% by weight of oleic acid;
d) about 22% by weight of 2-(2-ethoxyethoxy)ethanol;
e) about 5% by weight of dipropylene glycol;
f) from 38% by weight of PEG400; and
g) about 2% by weight of hydoxypropyl cellulose,
wherein the total weight of the one or more topical excipients from b) to f) is 100%.

In some embodiments of any one of the above formulations (FII-7) to (FII-17), the hydoxypropyl cellulose is the product sold under the name Klucel™ HF.

In some embodiments, the hydoxypropyl cellulose is absent in any one of the above formulations (FII), (FII-1) to (FII-17).

In some embodiments, the topical formulation (FIII) comprises:
a) from 0.5% to 15% by weight of the compound of formula (I) or a hydrate, solvate, and/or pharmaceutically acceptable salt thereof, on a salt-free and anhydrous basis;

b) from 20% to 30% by weight of DMSO;
c) from 5% to 15% by weight of a fatty acid, a fatty alcohol, a fatty ester, or combinations thereof;
d) from 10% to 30% by weight of $C_{1-3}$ alkyl-$(OCH_2CH_2)_{1-5}$—OH; and
e) from 30% to 50% by weight of a $C_{2-6}$ alkylene glycol, a di-($C_{2-6}$ alkylene) glycol, a polyethylene glycol, or combinations thereof, wherein the total weight of the one or more topical excipients from b) to e) is 100%.

In some embodiments, the topical formulation (FIII-1) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 5% to 15% by weight of a fatty acid;
d) from 10% to 30% by weight of $C_{1-3}$ alkyl-$(OCH_2CH_2)_{1-5}$—OH; and
e) from 30% to 50% by weight of a di-($C_{2-6}$ alkylene) glycol, wherein the total weight of the one or more topical excipients from b) to e) is 100%.

In some embodiments of any one of formulations (FIII) and (FIII-1), the fatty acid is oleic acid; the fatty alcohol is oleyl alcohol; the fatty ester is glycerol monooleate; $C_{1-3}$ alkyl-$(OCH_2CH_2)_{1-5}$—OH is 2-(2-ethoxyethoxy)ethanol (sold under the name Transcutol®); and the di-($C_{2-6}$ alkylene) glycol is dipropylene glycol.

In some embodiments, the topical formulation (FIII-2) comprises:
a) from 0.5% to 15% by weight of the compound of formula (I) or a hydrate, solvate, and/or pharmaceutically acceptable salt thereof, on a salt-free and anhydrous basis;
b) from 20% to 30% by weight of DMSO;
c) from 5% to 15% by weight of oleic acid;
d) from 10% to 30% by weight of 2-(2-ethoxyethoxy)ethanol; and
e) from 30% to 50% by weight of dipropylene glycol, wherein the total weight of the one or more topical excipients from b) to e) is 100%.

In some embodiments, the topical formulation (FIII-3) comprises:
a) about 3% by weight of the compound of formula (I) or a hydrate, solvate, and/or pharmaceutically acceptable salt thereof, on a salt-free and anhydrous basis;
b) about 30% by weight of DMSO;
c) about 10% by weight of oleic acid;
d) about 20% by weight of 2-(2-ethoxyethoxy)ethanol; and
e) about 40% by weight of dipropylene glycol, wherein the total weight of the one or more topical excipients from b) to e) is 100%.

In some embodiments, the topical formulation (FIII-4) comprises:
a) about 10% by weight of 3-(4-morpholinothieno[3,2-d]pyrimidin-2-yl)phenyl acetate or a hydrate, solvate, and/or pharmaceutically acceptable salt thereof, on a salt-free and anhydrous basis;
b) about 30% by weight of DMSO;
c) about 10% by weight of oleic acid;
d) about 20% by weight of 2-(2-ethoxyethoxy)ethanol; and
e) about 40% by weight of dipropylene glycol, wherein the total weight of the one or more topical excipients from b) to e) is 100%.

In some embodiments of any one of the above formulations (FIII-2) to (FIII-4), the topical formulation further includes tocopherol.

In some embodiments, the topical formulations as described herein have a visual appearance as clear, transparent, or monophasic. In some embodiments, the visual appearance of the topical formulation is maintained over a period of 10 days at a temperature of 80° C. In some embodiments, the visual appearance of the topical formulation is maintained over a period of 6 months at a temperature of 40° C. and a relative humidity of 75%.

When one or more gelling agents are present, the topical gel formulations as described herein have stable viscosity for a period of 10 days at a temperature of 80° C. or over a period of 6 months at a temperature of 40° C. and a relative humidity of 75%. In some embodiments, the viscosity of the topical gel formulation is maintained from 5,000 to 100,000 cps over a period of 10 days at a temperature of 80° C. or over a period of 6 months at a temperature of 40° C. and a relative humidity of 75%. In some embodiments, the viscosity of the topical gel formulation is maintained from 5,000 to 50,000 cps over a period of 10 days at a temperature of 80° C. or over a period of 6 months at a temperature of 40° C. and a relative humidity of 75%. In some embodiments, the viscosity of the topical gel formulation is maintained from 5,000 to 15,000 cps over a period of 10 days at a temperature of 80° C. or over a period of 6 months at a temperature of 40° C. and a relative humidity of 75%.

The purity of the compound of formula (I) in the formulation can be determined by an analytical method, for example a HPLC method. In some embodiments, the compound of formula (I) has a purity of 95% to 105% present in the topical formulation at time zero (i.e., day 0).

The topical formulations as described herein provide suitable physical stability of the compound of formula (I) for a period of 10 days at a temperature of 80° C. or over a period of 6 months at a temperature of 40° C. and a relative humidity of 75%. In some embodiments, the relative purity of the compound having formula (I) in the formulation has a decrease of less than 10% over a period of 10 days at a temperature of 80° C. or over a period of 6 months at a temperature of 40° C. and a relative humidity of 75%. In some embodiments, the relative purity of the compound having formula (I) in the formulation has a decrease of less than 5% over a period of 10 days at a temperature of 80° C. or over a period of 6 months at a temperature of 40° C. and a relative humidity of 75%. In some embodiments, the relative purity of the compound having formula (I) in the formulation has a decrease of less than 2% over a period of 10 days at a temperature of 80° C. or over a period of 6 months at a temperature of 40° C. and a relative humidity of 75%. In some embodiments, the relative purity of the compound having formula (I) in the formulation has a decrease of less than 1% over a period of 10 days at a temperature of 80° C. or over a period of 6 months at a temperature of 40° C. and a relative humidity of 75%.

It is believed that the compound of formula (I) can hydrolyze to a corresponding compound of formula (IV) under certain conditions, as shown below:

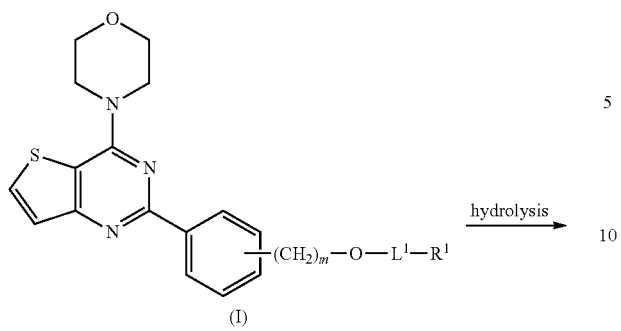

(I)

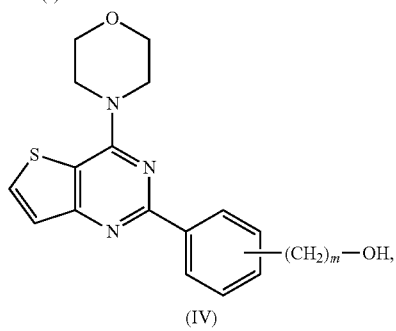

(IV)

wherein subscript m, L$^1$, and R$^1$ are as defined and described herein.

In some embodiments, the hydrolysis of the compound having formula (I) in the formulation to a corresponding compound having formula (IV) is less than 10% over a period of 10 days at a temperature of 80° C. or over a period of 6 months at a temperature of 40° C. and a relative humidity of 75%. In some embodiments, the hydrolysis of the compound having formula (I) in the formulation to a corresponding compound having formula (IV) is less than 5% over a period of 10 days at a temperature of 80° C. or over a period of 6 months at a temperature of 40° C. and a relative humidity of 75%. In some embodiments, the hydrolysis of the compound having formula (I) in the formulation to a corresponding compound having formula (IV) is less than 2% over a period of 10 days at a temperature of 80° C. or over a period of 6 months at a temperature of 40° C. and a relative humidity of 75%. In some embodiments, the hydrolysis of the compound having formula (I) in the formulation to a corresponding compound having formula (IV) is less than 1% over a period of 10 days at a temperature of 80° C. or over a period of 6 months at a temperature of 40° C. and a relative humidity of 75%.

The topical formulations as described herein provide enhanced skin permeation as compared to the compound of formula (IV) in the formulation with the same composition (i.e., the same one or more topical excipients). The skin permeability can be assessed by skin flux experiments in various animal skin models. In some embodiments, the skin flux of the compound having formula (I) has an increase of from 2 to 5 fold as compared to a skin flux of the corresponding compound having formula (IV) in the same topical formulation. In some embodiments, the skin flux of the compound having formula (I) has an increase of about 2 fold, as compared to a skin flux of the corresponding compound having formula (IV) in the same topical formulation.

In some embodiments, the compound of formula (I) in the formulation is represented by formula (IIa):

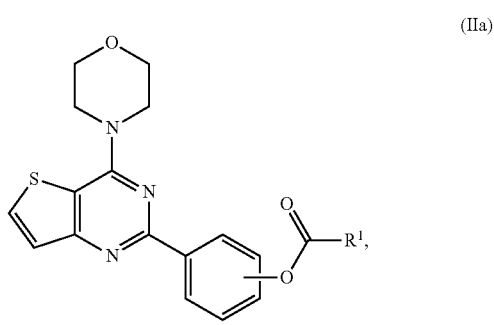

(IIa)

wherein R$^1$ or —C(O)R$^1$ as L$^1$-R$^1$ are as defined and described herein.

In some embodiments, the compound of formula (I) in the formulation is represented by any one of formulae (IIb), (IIc), and (IId):

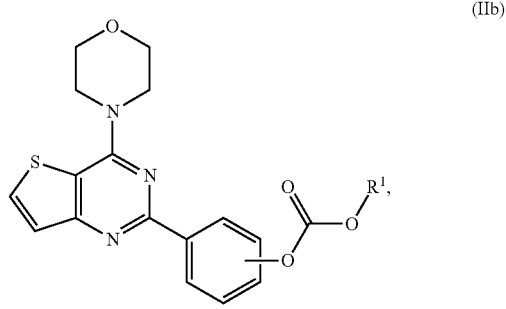

(IIb)

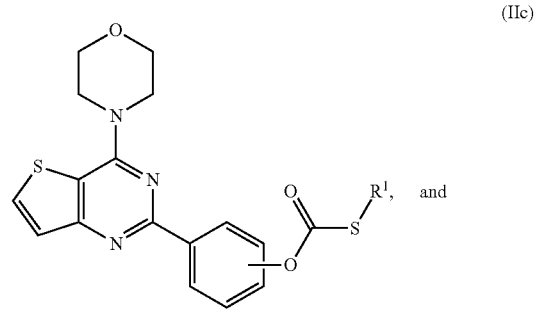

(IIc)

and

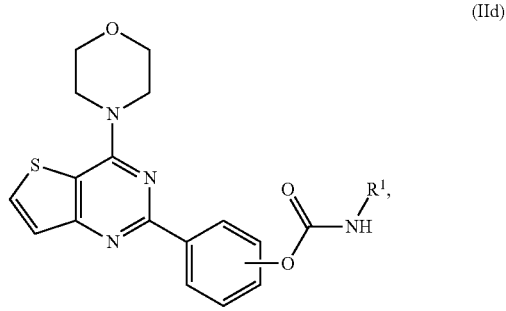

(IId)

wherein R$^1$ is as defined herein in any aspect or embodiments described herein.

In some embodiments, the compound of formula (I) in the formulation is represented by the formula:

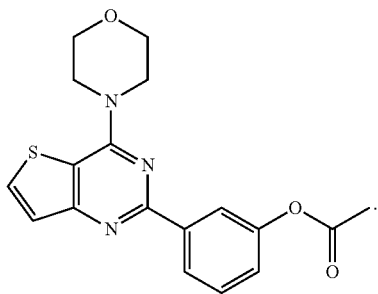

In some embodiments, the compound of formula (I) in the formulation is represented by formula (IIIa):

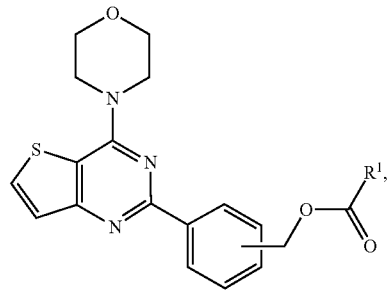
(IIIa)

wherein R¹ or —C(O)—R¹ as L¹-R¹ are as defined herein in any aspect or embodiments described herein.

In some embodiments, the compound of formula (I) in the formulation is represented by any one of formulae (IIIb), (IIIc), and (IIId):

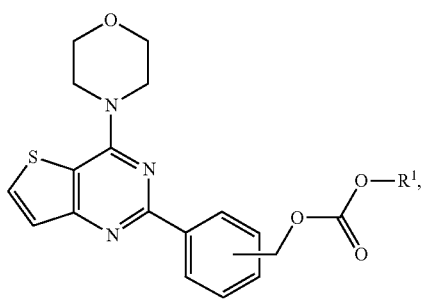
(IIIb)

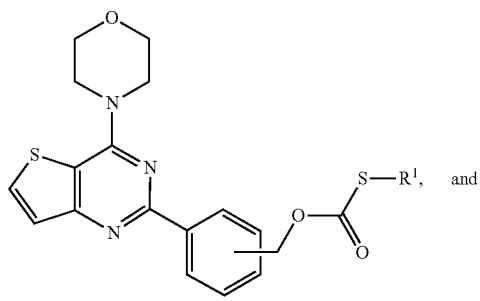
(IIIc)
and

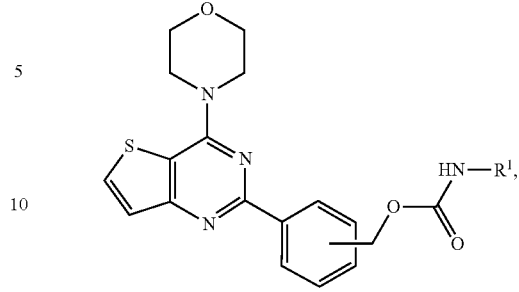
(IIId)

wherein R¹ is as defined herein in any aspect or embodiments described herein.

In some embodiments, the compound of formula (I) in the formulation is represented by the formula:

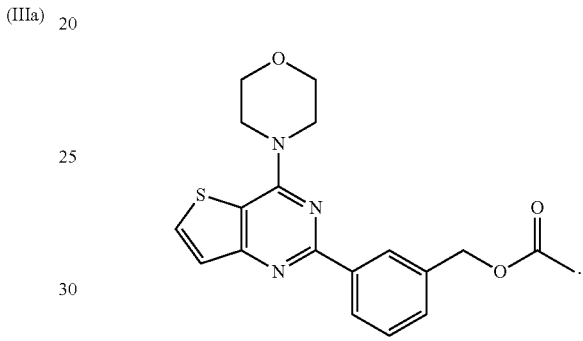

In some embodiments, the hydrolysis of 3-(4-morpholinothieno[3,2-d]pyrimidin-2-yl)phenyl acetate in the formulation to 3-(4-morpholinothieno[3,2-d]pyrimidin-2-yl)phenol is less than 10% over a period of 10 days at a temperature of 80° C. or over a period of 6 months at a temperature of 40° C. and a relative humidity of 75%. In some embodiments, the hydrolysis of 3-(4-morpholinothieno[3,2-d]pyrimidin-2-yl)phenyl acetate in the formulation to 3-(4-morpholinothieno[3,2-d]pyrimidin-2-yl)phenol is less than 5% over a period of 10 days at a temperature of 80° C. or over a period of 6 months at a temperature of 40° C. and a relative humidity of 75%. In some embodiments, the hydrolysis of 3-(4-morpholinothieno[3,2-d]pyrimidin-2-yl)phenyl acetate in the formulation to 3-(4-morpholinothieno[3,2-d]pyrimidin-2-yl)phenol is less than 2% over a period of 10 days at a temperature of 80° C. or over a period of 6 months at a temperature of 40° C. and a relative humidity of 75%. In some embodiments, the hydrolysis of 3-(4-morpholinothieno[3,2-d]pyrimidin-2-yl)phenyl acetate in the formulation to 3-(4-morpholinothieno[3,2-d]pyrimidin-2-yl)phenol is less than 1% over a period of 10 days at a temperature of 80° C. or over a period of 6 months at a temperature of 40° C. and a relative humidity of 75%.

In some embodiments, the hydrolysis of 3-(4-morpholinothieno[3,2-d]pyrimidin-2-yl)benzyl acetate in the formulation to (3-(4-morpholinothieno[3,2-d]pyrimidin-2-yl)phenyl)methanol is less than 10% over a period of 10 days at a temperature of 80° C. or over a period of 6 months at a temperature of 40° C. and a relative humidity of 75%. In some embodiments, the hydrolysis of 3-(4-morpholinothieno[3,2-d]pyrimidin-2-yl)benzyl acetate in the formulation to (3-(4-morpholinothieno[3,2-d]pyrimidin-2-yl)phenyl)methanol is less than 5% over a period of 10 days at a temperature of 80° C. or over a period of 6 months at a temperature of 40° C. and a relative humidity of 75%. In some embodiments, the hydrolysis of 3-(4-morpholinothieno[3,2-d]pyrimidin-2-yl)banzyl acetate in the formulation to (3-(4-morpholinothieno[3,2-d]pyrimidin-2-yl)phenyl)methanol is less than 2% over a period of 10 days at a temperature of 80° C. or over a period of 6 months at a temperature of 40° C. and a relative humidity of 75%. In some embodiments, the hydrolysis of 3-(4-morpholinothieno[3,2-d]pyrimidin-2-yl)benzyl acetate in the formulation to (3-(4-morpholinothieno[3,2-d]pyrimidin-2-yl)phenyl)methanol is less than 1% over a period of 10 days at a temperature of 80° C. or over a period of 6 months at a temperature of 40° C. and a relative humidity of 75%.

The topical formulation used to deliver the compound of formula (I) is a lotion, a spray, an ointment, a cream, a gel, a paste, or a patch.

In some embodiments, the topical formulation used to deliver the compound of formula (I) is a lotion or a cream. Creams and lotions that can be used as topical formulations and their preparation are disclosed in REMINGTON: THE SCIENCE AND PRACTICE OF PHARMACY 282-291 (Alfonso R. Gennaro ed. 19th ed. 1995), hereby incorporated herein by reference.

In some embodiments, the topical formulation used to deliver the compound of formula (I) is a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels for use with the invention are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002), each of which patents is hereby incorporated herein by reference.

In some embodiments, the topical formulation used to deliver the compound of formula (I) is an ointment. Ointments are oleaginous semisolids that contain little if any water. In some instances, the ointment is hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

In some embodiments, the topical administration may be achieved in the form of patches comprising the topical formulation as described herein. In some embodiments, the patch is in contact with the affected area on the skin. In some embodiments, the patch is in contact with adjacent areas on the skin to the affected area.

V. Method

In a third aspect, the present invention provides a method of treating a vascular malformation through inhibiting phosphoinositide-3-kinase (PI3K). The method includes administering to a subject in need thereof, an effective amount of the topical formulation including the compound of formula (I) and one or more topical excipients.

The term "vascular malformation," as used herein, refers to a non-malignant, congenital abnormality of blood and/or lymph vessels that may be apparent at birth or alternatively may not be apparent at birth and may present weeks, months, or years later. In some embodiments, the vascular malformation is not a hemangioma. In certain non-limiting embodiments, a vascular malformation is characterized by the presence of a single endothelial layer forming distended blood vessels of variable diameter that are surrounded by a disorganized mural cell layer containing both smooth muscle cells and pericytes.

In some embodiments, the vascular malformation may be a venous malformation, an arterial malformation, an arteriovenous malformation or a lymphatic vessel malformation. In certain non-limiting embodiments, the subject suffers from multiple vascular malformations.

Vascular malformations may be located in or adjacent to diverse areas of the body, including but not limited to the central nervous system (brain, spinal cord), skin, eye (including but not limited to the retina), ear, (facial) sinus, organs such as the lung, heart, liver, gallbladder, spleen, gastrointestinal system (esophagus, stomach, duodenum, intestine, colon, rectum), pancreas, kidney, bladder, ovary, testicle, joints, nose, lips, etc.

In some embodiments, the subject suffers from a malignancy.

In some embodiments, the subject is not known to suffer from a malignancy.

In some embodiments, the subject suffers from a multisystem genetic disorder.

In some embodiments, the subject is not known to suffer from a multisystem genetic disorder.

In some embodiments, the subject suffers from at least one vascular malformation, the surgical treatment of which would be high-risk. These would include vascular malformations in an area that is, because of its location, difficult to access without substantial risk of morbidity or mortality (for example, but not limited to, malformations in the brain, e.g., the brainstem), as well as malformations in a weakened subject where surgery is contraindicated. Further, if there are multiple lesions, medical treatment may be preferable over surgical options because of aggregate risk, efficiency, or because of risk of recurrence.

In some embodiments, the subject is at risk for occurrence or recurrence of a vascular malformation, for example because of heredity and/or a previously existing lesion.

In some embodiments, the topical formulation is administered topically in the area of the vascular malformation. In some embodiments, the topical formulation is administered topically as a lotion, a spray, an ointment, a cream, a gel, a paste, or a patch.

After topical delivery, it is believed that the compound of formula (I) is converted to a to a corresponding compound of formula (IV), as shown below:

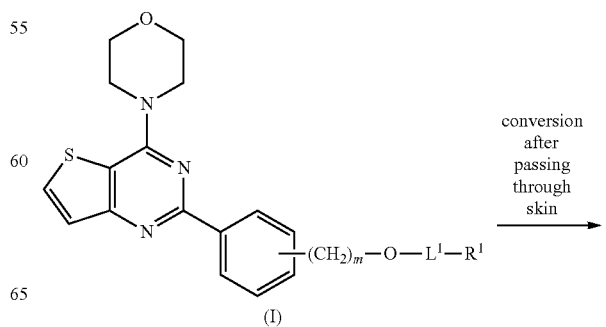

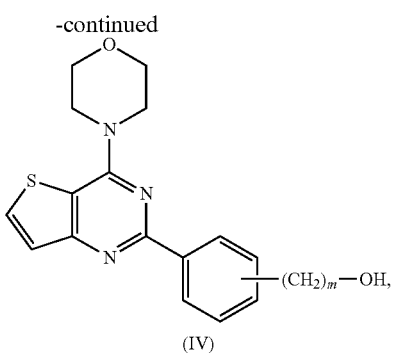

(IV)

wherein subscript m, L¹, and R¹ are as defined and described herein.

In some embodiments, the method of the present invention includes topical administration of the topical formulation including the compound of formula (I), which is capable of inhibiting one or more of the phosphoinositide 3-kinase enzymes, which are part of the PI3K/AKT pathway, thereby providing beneficial therapeutic effects for the treatment of vascular malformations.

In some embodiments, the method of the present invention includes topical administration of the topical formulation including the compound of formula (I), wherein the compound of formula (I) is substantially converted to a corresponding compound of formula (IV), which is capable of inhibiting one or more of the phosphoinositide 3-kinase enzymes, which are part of the PI3K/AKT pathway, thereby providing beneficial therapeutic effects for the treatment of vascular malformations.

In some embodiments, the conversion of the compound having formula (I) to a corresponding compound having formula (IV) after passing a skin is at least 50% over a period of 24 hours. In some embodiments, the conversion of the compound having formula (I) to a corresponding compound having formula (IV) after passing a skin is from 50% to 99%, from 60% to 90%, or from 70% to 90% over a period of 24 hours. In some embodiments, the conversion of the compound having formula (I) to a corresponding compound having formula (IV) after passing a skin is about 85% over a period of 24 hours.

When the compound having formula (I) is delivered by a non-topical route, in some embodiments, the conversion of the compound having formula (I) to a corresponding compound having formula (IV) in a subject is at least 50% over a period of 24 hours. In some embodiments, the conversion of the compound having formula (I) to a corresponding compound having formula (IV) in a subject is from 50% to 99%, from 60% to 90%, or from 70% to 90% over a period of 24 hours. In some embodiments, the conversion of the compound having formula (I) to a corresponding compound having formula (IV) in a subject is about 85% over a period of 24 hours.

In some embodiments, the compound of formula (I) in the formulation used in the method is any one of formulae (II), (IIa), (IIb), (IIc), (IId), (IIa-1), (IIIa), (IIIb), (IIIc), (IIId), (IIIa-1). In some embodiments, the compound of formula (I) in the formulation used in the method is 3-(4-morpholinothieno[3,2-d]pyrimidin-2-yl)phenyl acetate. In some embodiments, the compound of formula (I) in the formulation used in the method is 3-(4-morpholinothieno[3,2-d]pyrimidin-2-yl)benzyl acetate.

In some embodiments, the method of the present invention includes topical administration of the topical formulation including 3-(4-morpholinothieno[3,2-d]pyrimidin-2-yl)phenyl acetate that is converted to 3-(4-morpholinothieno[3,2-d]pyrimidin-2-yl)phenol, which inhibits the PI3K/AKT pathway, thereby treating the vascular malformation.

In some embodiments, the method of the present invention includes topical administration of the topical formulation including 3-(4-morpholinothieno[3,2-d]pyrimidin-2-yl)benzyl acetate that is converted to (3-(4-morpholinothieno[3,2-d]pyrimidin-2-yl)phenyl)methanol, which inhibits the PI3K/AKT pathway, thereby treating the vascular malformation.

The treatment methods of the invention may be administered alone or in conjunction with another form of pharmaceutical and/or surgical therapy. Non-limiting examples of pharmaceutical treatments and/or agents include, but are not limited, to treatment with one or more of: an anti-angiogenic agent, a steroid, an mTOR inhibitor, a beta-blocker (e.g., propranolol), and/or an agent that reduces blood pressure. In certain embodiments, "in conjunction with," means that an inhibitor of the PI3K/Akt pathway and another pharmaceutical agent, e.g., an mTOR inhibitor, are administered to a subject as part of a treatment regimen or plan. In certain embodiments, being used in conjunction does not require that the PI3K/Akt pathway inhibitor and the pharmaceutical agent are physically combined prior to administration or that they be administered over the same time frame.

VI. Examples

General Synthesis Method

The compounds provided herein can be prepared, isolated or obtained by any method apparent to those of skill in the art. Compounds provided herein can be prepared according to the Exemplary Preparation Schemes provided below. Reaction conditions, steps and reactants not provided in the Exemplary Preparation Schemes would be apparent to, and known by, those skilled in the art. As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mol (moles); mmol (millimoles); h, hr, or hrs (hours); min (minutes); rt or RT (room temperature); MS (mass spectrometry); ESI (electrospray ionization); TLC (thin layer chromatography); HPLC (high pressure liquid chromatography); THF (tetrahydrofuran); CDCl₃ (deuterated chloroform); AcOH (acetic acid); Ac₂O (acetic anhydride), DCM (dichloromethane); DMSO (dimethylsulfoxide); DMSO-d₆ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Compounds of formula (IIa) or (IIb) are prepared via key intermediate 6 according to synthesis Scheme 1, as shown in FIG. 1.

Figure 2:
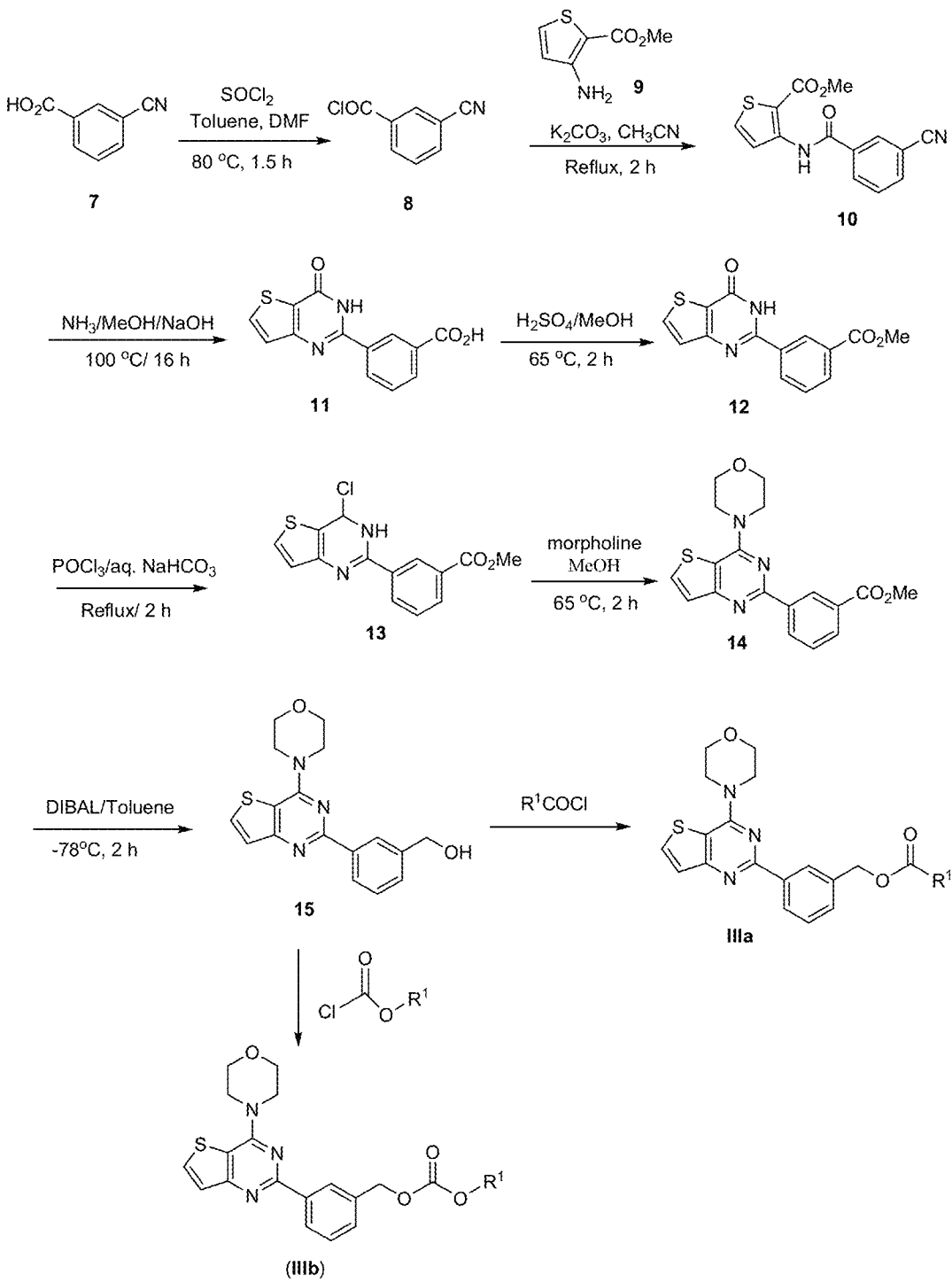
FIG. 2 shows synthesis Scheme 2 for preparing a compound of formula (IIIa) or (IIIb).

Compounds of formula (IIIa) or (IIIb) are prepared via key intermediate 15 according to synthesis Scheme 2, as shown in FIG. 2.

Example 1: 3-(4-Morpholinothieno[3,2-d]pyrimidin-2-yl)phenyl Acetate (Compound 1.002)

Step-1: Methyl 3-(3-methoxybenzamido)thiophene-2-carboxylate (3)

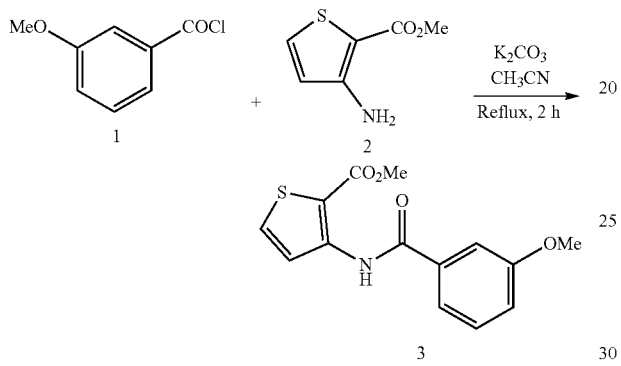

To a solution of methyl-3-amino-2-thiophenecarboxylate (2) (90 g, 0.57 mol, 1.0 equiv.) in acetonitrile (1075 mL) was added potassium carbonate (87.0 g, 0.63 mol) followed by 3-methoxybenzoyl chloride (1) (96.8 g, 0.57 mol) and the mixture was heated at reflux for 1 h. Most of the acetonitrile was evaporated under reduced pressure to provide a light yellowish solid residue. Water (2.0 L) was added and the reaction mixture was stirred for 1 h. The solid was collected by filtration, washed with water (200 mL) and dried to obtain methyl 3-(3-methoxybenzamido)thiophene-2-carboxylate (3) (156.2 g, yield: 93.65%).

Step-2: 2-(3-Methoxyphenyl)thieno[3,2-d]pyrimidin-4(3H)-one (4)

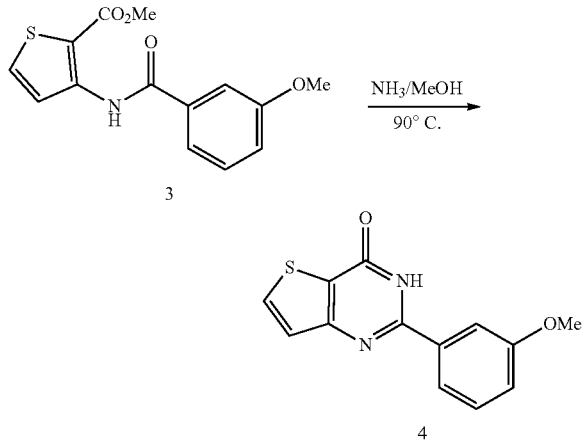

An ammonia solution in methanol (14%, 2.0 L) was added to methyl 3-(3-methoxybenzamido)thiophene-2-carboxylate (3) (100.0 g, 0.343 mol) and the mixture was heated at 70° C. for 36 h in a steel bomb at 50 psi. The solvent was removed under reduced pressure. Isopropanol (1.66 L) was added followed by aqueous sodium hydroxide solution (2 M, 2.0 L). The solution was heated under reflux for 15 h and then cooled in an ice-water bath. The reaction mixture was acidified to pH 1 using aqueous hydrochloric acid (4 M, 1.1 L) and the precipitated white solid was collected by filtration, washed with water (2.0 L) and dried at 50° C. in a vacuum oven to give 2-(3-methoxyphenyl)thieno[3,2-d]pyrimidin-4(3H)-one (4) (75.1 g, yield: 84.7%).

Step-3: 4-Chloro-2-(3-methoxyphenyl)thieno[3,2-d]pyrimidine (5)

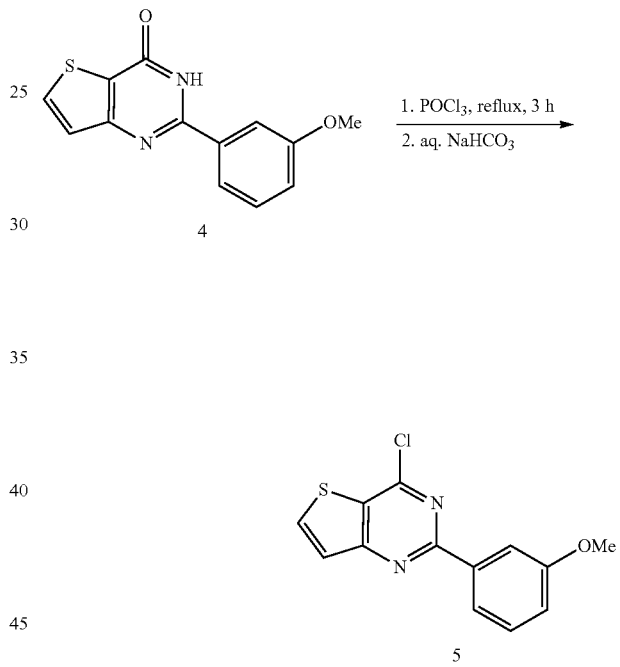

To 2-(3-methoxyphenyl)thieno[3,2-d]pyrimidin-4(3H)-one (4) (150.0 g, 0.58 mol) was added phosphorus oxychloride (750 mL) and the dark mixture was heated at reflux for 5 h. Most of the excess phosphorus oxychloride was removed by distillation under reduced pressure. The remaining oily residue was added to saturated aqueous sodium bicarbonate (4.0 L) below 20° C. The reaction mixture was stirred for 2 h at 20° C. The resulting solid was collected by filtration, washed thoroughly with water (0.5 L) and dried in a vacuum oven at 50° C. for 24 h to obtain 4-chloro-2-(3-methoxyphenyl)thieno[3,2-d]pyrimidine (5) (122.5 g, 76.3%). A remaining sticky material (in the flask) was dissolved in dichloromethane (1.5 L) and the solution was stirred with saturated aqueous sodium bicarbonate (1.5 L) below 20° C. The dichloromethane layer was separated, dried over $Na_2SO_4$ and concentrated to obtain a second crop of compound 5 (29.4 g, 18.3%) for an overall yield of 151.9 g (94.6%).

Step-4: 4-(2-(3-Methoxyphenyl)thieno[3,2-d]pyrimidin-4-yl)morpholine (Compound 1.001)

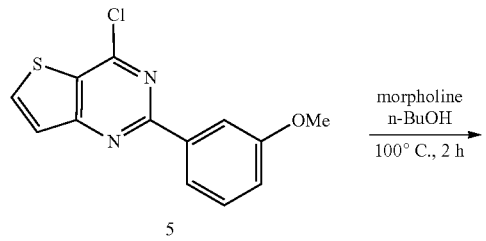

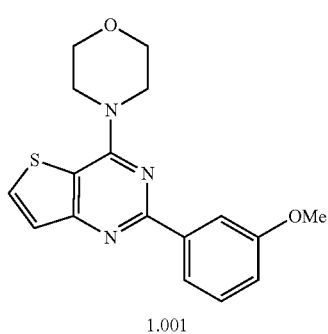

Morpholine (165.27 g, 1.897 mol) was added to a stirred suspension of 4-chloro-2-(3-methoxyphenyl)thieno[3,2-d]pyrimidine (5) (150.0 g, 0.542 mol) in methanol (3.75 L). The reaction mixture was heated at reflux for 2 h. Most of the methanol (85-90% of original volume) was evaporated under reduced pressure. The resulting solid was collected by filtration then suspended in water (2.0 L) and stirred for 1 h. The solid was collected by filtration, washed with water (100 mL) and dried at 60° C. in a vacuum oven to obtain 4-(2-(3-methoxyphenyl)thieno[3,2-d]pyrimidin-4-yl)morpholine (1.001) (151.0 g, 85%).

Step-5: 3-(4-Morpholinothieno[3,2-d]pyrimidin-2-yl)phenol (6)

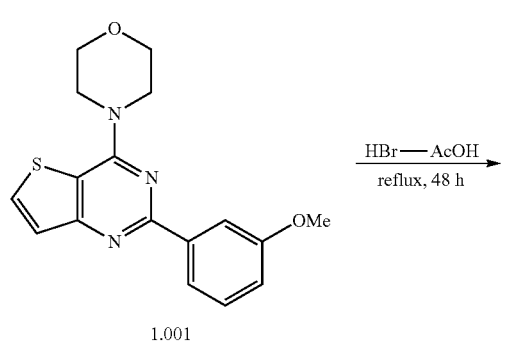

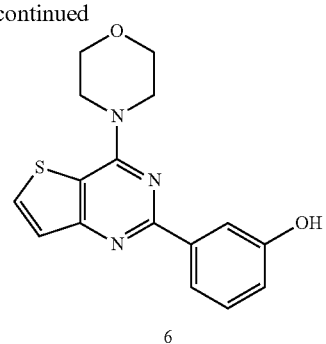

Aqueous HBr (48%, 900 mL) was added to a suspension of 4-(2-(3-methoxyphenyl) thieno[3,2-d]pyrimidin-4-yl) morpholine (1.001) (150.0 g, 0.458 mol) in acetic acid (900 mL) and the reaction mixture was heated at reflux for 24 h. The reaction mixture was cooled to 20° C. The precipitated solid was collected by filtration and washed with demineralized water (1.0 L). The solid was mixed with saturated aqueous solution of sodium bicarbonate (0.75 L) and stirred at room temperature for 1.0 h. The solid was collected by filtration, washed thoroughly with water (0.75 L) and dried at 50° C. in a vacuum oven to obtain crude 3-(4-morpholinothieno[3,2-d]pyrimidin-2-yl)phenol (6) (103.1 g, yield: 71.8%).

DMSO (388 mL) was added to crude 6 (77.7 g) at room temperature. The mixture was stirred at 50° C. for 30 minutes to dissolve the solid completely. The solution was cooled to 35° C. and filtered through 0.45-micron filter. Demineralized water (1.3 L) was added to the filtrate and stirred for 2 h. The precipitated white solid was filtered, washed with water (0.5 L), dried in a vacuum oven at 60° C. to obtain pure 6 (75.2 g, 96.7%).

Step-6: 3-(4-Morpholinothieno[3,2-d]pyrimidin-2-yl)phenyl Acetate (Compound 1.002)

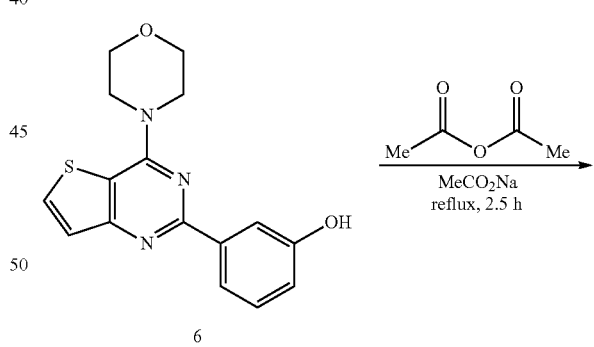

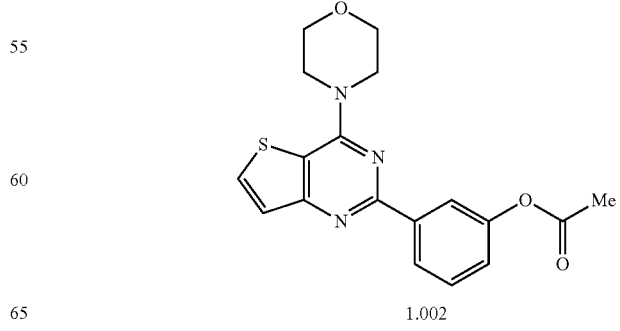

A mixture of 3-(4-morpholinothieno[3,2-d]pyrimidin-2-yl)phenol (6) (10.0 g, 31.9 mmol), sodium acetate (0.65 g, 0.25 eq., 3.86 mol) and acetic anhydride (6.52 g, 2.0 eq., 63.82 mmol) in ethyl acetate (250 mL) was heated to 80° C. for 2.5 h. The reaction mixture was cooled to 40° C. Activated charcoal (2.5 g) was added and stirred for 1 h at 40° C. The reaction mixture was filtered through a hyflow bed and the solid was rinsed with ethyl acetate (50 mL). The filtrate was washed with saturated aqueous sodium bicarbonate (100 mL) then with demineralized water (100 mL), dried over $Na_2SO_4$, filtered through 0.45-micron filter and the solid was rinsed with ethyl acetate (50 mL). The filtrate was concentrated to remove about 70-80% of the original volume. n-Heptane (20 mL) was added and the solvent was fully evaporated under reduced pressure to obtain 3-(4-morpholinothieno[3,2-d]pyrimidin-2-yl)phenyl acetate (1.002) (9.1 g, 80.2%) as an off white solid.

Example 2: 3-(4-Morpholinothieno[3,2-d]pyrimidin-2-yl)phenyl Hexanoate (Compound 1.006)

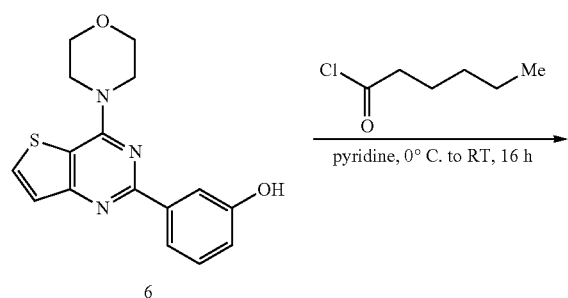

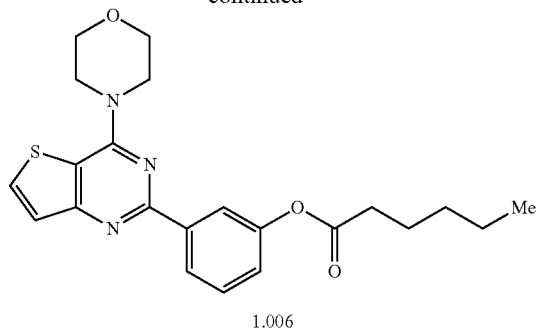

1.006

Hexanoyl chloride (12.88 g, 95.73 mmol) was added dropwise to a solution of 6 (10.0 g, 31.9 mmol) in pyridine (410.0 mL) at 0° C. The reaction mixture was warmed up to room temperature and stirred for 16 h. Analysis indicated that the reaction mixture contained about 95% of unreacted starting material. Hexanoyl chloride (4.0 g) was added at 0° C. and the reaction mixture was stirred for 24 h at room temperature. TLC analysis showed that about 50% to 60% of unreacted 6 was still remaining. The reaction mixture was concentrated under vacuum. Methylene chloride (2×500 mL) was added to the residue followed by saturated aqueous $NaHCO_3$ solution (1.0 L). After stirring the mixture for 15 min, stirring was stopped and the organic layer was separated and dried over anhydrous sodium sulfate. The solution was filtered and the solvent was evaporated under reduced pressure. The resulting crude product was purified by column chromatography on silica gel using 0-30% EtOAc in n-heptane as eluent to obtain 3-(4-morpholinothieno[3,2-d]pyrimidin-2-yl)phenyl hexanoate (1.006) as a yellow sticky semi-solid (2.4 g, yield: 18.3%).

Example 3: 3-(4-Morpholinothieno[3,2-d]pyrimidin-2-yl)phenyl Decanoate (Compound 1.008)

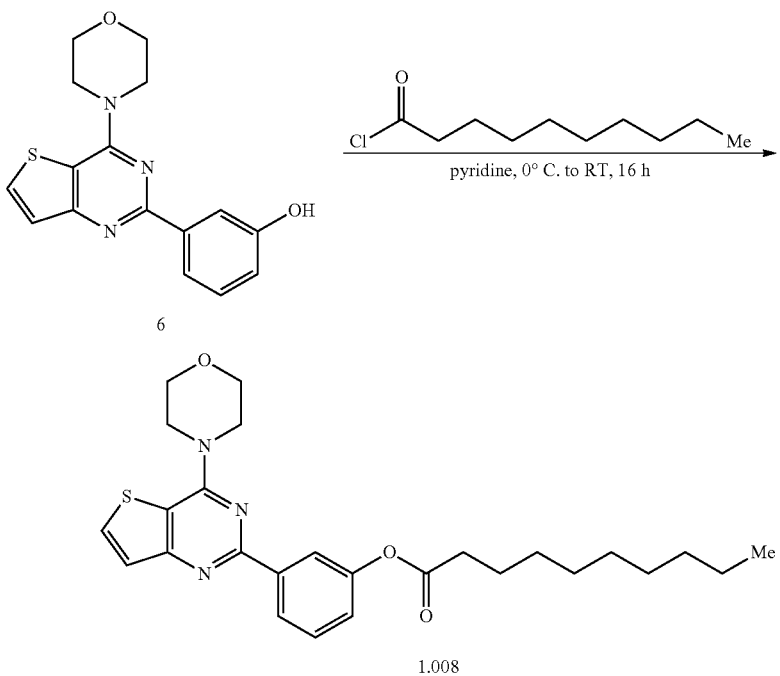

Decanoyl chloride (18.2 g, 95.73 mmol) was added dropwise to a solution of 6 (10.0 g, 31.91 mmol) in pyridine (410.0 mL) at 0° C. The reaction mixture was warmed to room temperature and stirred for 16 h. The reaction mixture was concentrated under vacuum. The crude product (9.0 g) was dissolved in ethyl acetate (250 ml). Saturated NaHCO₃ solution (2×500 mL) was added to the solution and stirred for 30 minutes at room temperature. The organic layer was separated and dried over anhydrous Na₂SO₄. The solvent was evaporated under reduced pressure to provide the crude product. The crude product was purified by column chromatography on silica gel using 15% ethyl acetate in n-heptane to obtain 3-(4-morpholinothieno[3,2-d]pyrimidin-2-yl)phenyl decanoate (1.008) (10.0 g, 67.0%) as a yellowish liquid.

The product (9.0 g) was dissolved in EtOAc (250 mL) and the solution was mixed with saturated aqueous NaHCO₃ (500 mL) and stirred for 30 min. The organic layer was separated, dried (Na₂SO₄) and the solvent was evaporated under reduced pressure. The resulting product was further purified by column chromatography on silica gel using 15% EtOAc in n-heptane to give pure compound 1.008 (8.0 g, 88.9%) as a colorless sticky compound (overall yield: 59.6%).

Oleic acid (10.63 g, 37.65 mmol), EDC HCl (6.72 g, 35.10 mmol), DMAP (0.97 g, 7.98 mmol) were added to a solution of 6 (10.0 g, 31.91 mmol) in DCM (310 mL). The reaction mixture was stirred at room temperature for 15 h. Saturated NaHCO₃ solution (1.0 L) was added to the reaction mixture and stirred for 15 min. The layers were separated. The aqueous layer was extracted with methylene chloride (2×500 mL) and the extract was combined with the organic layer. The combined CH₂Cl₂ was dried over Na₂SO₄, filtered and the solvent was evaporated under reduced pressure to provide the crude product. The crude product was purified by column chromatography on silica gel using 0-30% ethyl acetate in n-heptane as eluent to provide 3-(4-morpholinothieno[3,2-d]pyrimidin-2-yl)phenyl oleate (1.011) as a colorless liquid (8.7 g, 47.18%).

Example 5: Ethyl (3-(4-morpholinothieno[3,2-d]pyrimidin-2-yl)phenyl) Carbonate (Compound 1.012)

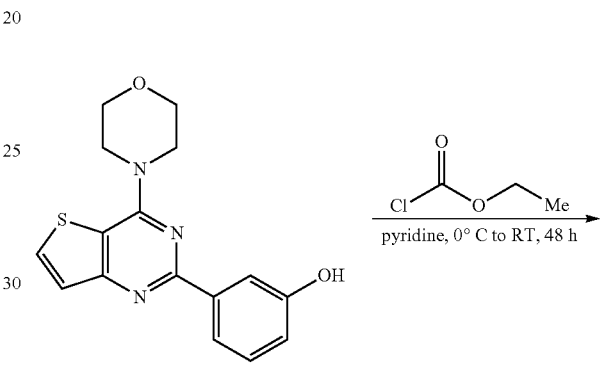

Example 4: 3-(4-Morpholinothieno[3,2-d]pyrimidin-2-yl)phenyl Oleate (Compound 1.011)

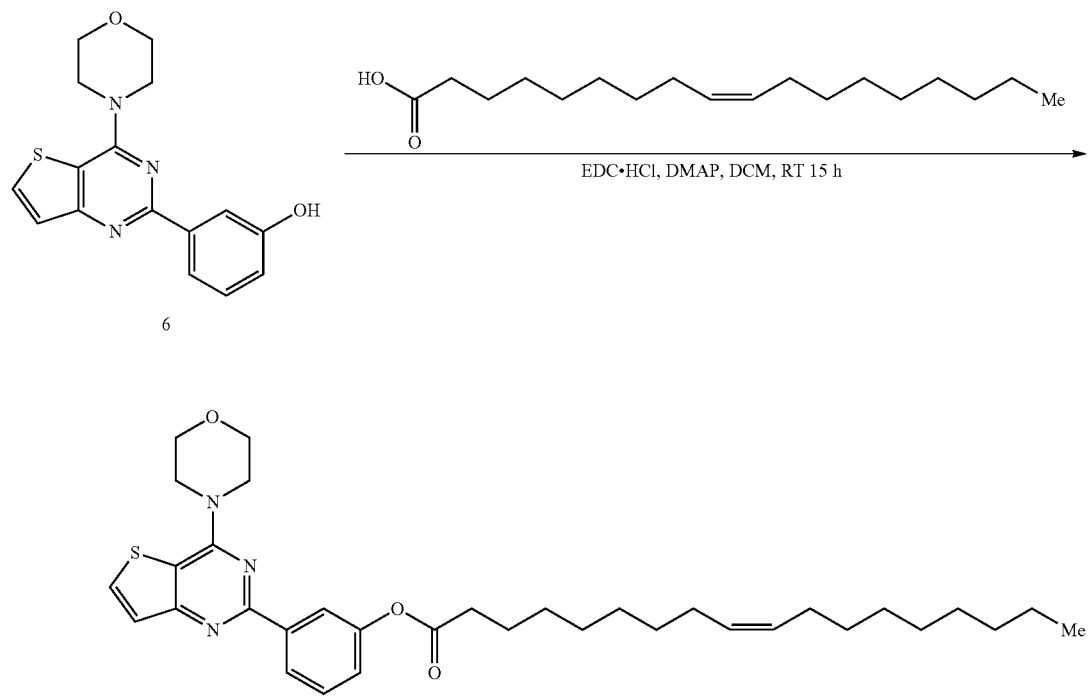

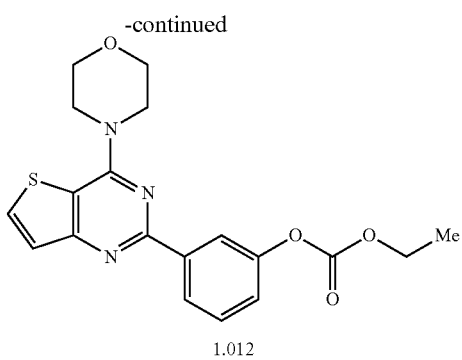

1.012

Ethyl chloroformate (10.38 g, 95.73 mmol) was added to a stirred solution of 3-(4-morpholinothieno[3,2-d]pyrimidin-2-yl)phenol (6) (10.0 g, 31.91 mmol) in pyridine (410 mL) at 0° C. The reaction mixture was warmed to room temperature and stirred for 48 h. The reaction mixture was concentrated under reduced pressure. Saturated aqueous sodium bicarbonate (1.0 L) was added to the residue and the product was extracted with DCM (2×500.0 mL). The combined organic extract was washed with water (2×500 mL), dried over sodium sulfate, filtered and concentrated under reduced pressure to obtain the crude product. The crude product was purified by column chromatography on silica gel using 0-30% EtOAc in n-heptane as eluent to afford ethyl (3-(4-morpholinothieno [3,2-d]pyrimidin-2-yl)phenyl) carbonate (1.012) as a white solid (8.0 g, 65.0%).

Example 6: 3-(4-Morpholinothieno[3,2-d]pyrimidin-2-yl)phenyl Cinnamate (Compound 1.014)

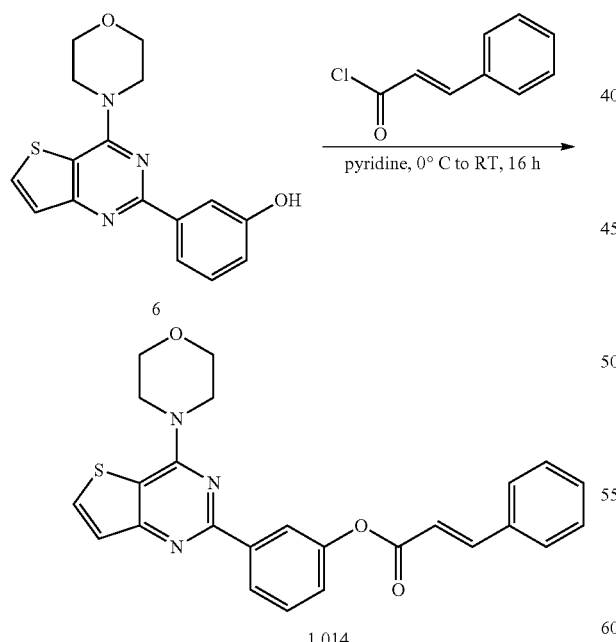

1.014

Cinnamoyl chloride (15.94 g, 95.73 mmol) was added dropwise to a solution of 6 (10.0 g, 31.9 mmol) in pyridine (410 mL) at 0° C. The reaction mixture was warmed to room temperature and stirred for 16 h. The reaction mixture was concentrated under reduced pressure. Methylene chloride (2×500 mL) was added to dissolve the residue. The methylene chloride solution was washed with saturated aqueous $NaHCO_3$ solution (1.0 L). The organic layer was separated and dried over anhydrous sodium sulfate, filtered and evaporated under reduced pressure to provide the crude product. The crude product was purified by column chromatography on silica gel using 0-30% ethyl acetate in n-heptane as eluent to obtain ethyl 3-(4-morpholinothieno[3,2-d]pyrimidin-2-yl)phenyl cinnamate (1.014) as a white solid in two crops (crop 1: 1.2 g and crop 2: 11.0 g; total 12.2 g, overall yield: 86.2%).

Example 7: 3-(4-Morpholinothieno[3,2-d]pyrimidin-2-yl)benzyl acetate (Compound 1.015)

Step 1: 3-cyanobenzoyl chloride (8)

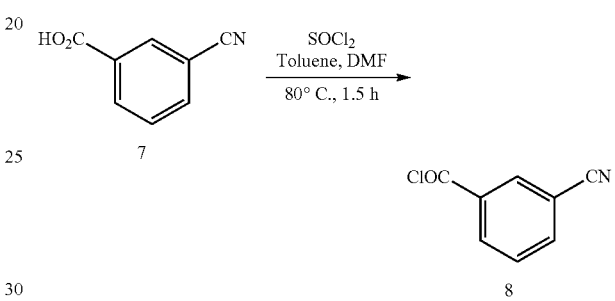

DMF (9 mL) and thionyl chloride (500 mL) were added to a stirred solution of 3-cynobenzoic acid (7) (1hge300 g, 679.8 mmol, 1.0 equiv.) in toluene (1.0 L) at room temperature. The resulting mixture was stirred for 1.5 h at 80° C. The progress of reaction was monitored by TLC (Mobile phase: 40% EtOAc in n-heptane). The solvent was evaporated under reduced pressure to afford 3-cyanobenzoyl chloride (8) as a yellow liquid (105.35 g, 93.6%).

Step 2: Methyl 3-(3-cyanobenzamide)thiophene-2-carboxylate (10)

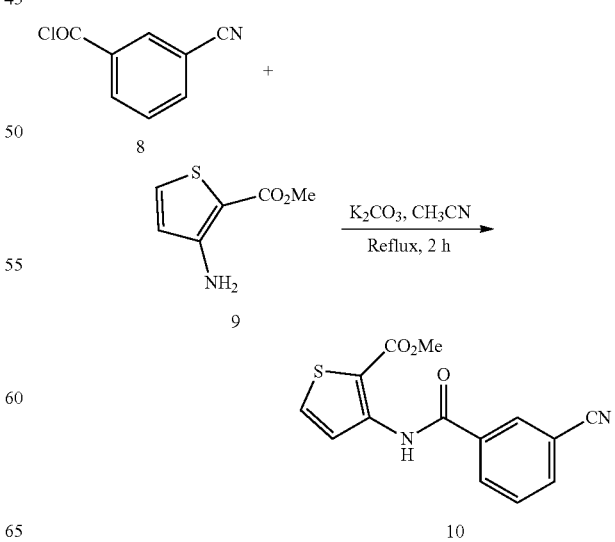

To a solution of methyl-3-amino-2-thiophenecarboxylate (9) (100 g, 636.17 mmol, 1.0 equiv.) in acetonitrile (1.0 L) was added potassium carbonate (96.71 g, 699.79 mmol, 1.1 equiv.) followed by 3-cyanobenzoyl chloride (8) (105.34 g, 636.17 mmol, 1.0 equiv.) and the mixture was heated under reflux for 2 h. Progress of reaction was monitor by TLC (Mobile phase: 35% EtOAc in n-heptane). A light-yellow precipitate appeared. Most of the acetonitrile was evaporated under reduced pressure to obtain a light yellowish solid. The mixture was diluted with water (1.2 L) and stirred for 0.5 h. The solid was collected by filtration, washed with water (0.4 L) and dried at 50° C. to obtain methyl 3-(3-cyanobenzamido)thiophene-2-carboxylate (10) (172.0 g, 94.2%).

Step 3: 3-(4-oxo-3,4-dihydrothieno[3,2-d]pyrimidin-2-yl)benzoic acid (11)

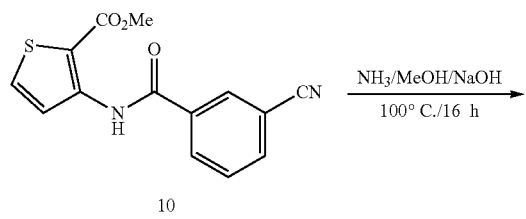

10

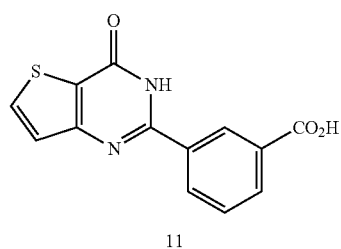

11

To a stirred solution of methyl 3-(3-cyanobenzamido)thiophene-2-carboxylate (10) (229.0 g, 799.83 mmol, 1.0 equiv.) in methanol (4.5 L) was cooled to 10° C. Ammonia was purged into the solution to make 11% ammoniacal solution then the mixture was heated at 100° C. for 16 h in a steel bomb at 200 psi. The progress of the reaction was monitor by TLC (Mobile phase: 5% MeOH in DCM). The solvent was then removed under vacuo and 2M aqueous sodium hydroxide (4.5 L) was added. The solution was heated at 80° C. for 1 h. The progress of reaction was monitor by TLC (Mobile phase: 5% MeOH in DCM). The mixture was cooled to 10° C. The reaction mixture was acidified to pH 1 using 4 M hydrochloric acid (4.5 L) and the white precipitate was collected by filtration and washed with water (2.2 L). The wet cake was stirred in isopropyl alcohol (572.5 mL) for 1 h at room temperature and the resulting solid was collected by filtration, dried at 60° C. to give compound 3-(4-oxo-3,4-dihydrothieno[3,2-d]pyrimidin-2-yl)benzoic acid (11) (206.0 g, 94.6%).

Step 4: Methyl 3-(4-oxo-3,4-dihydrothieno[3,2-d]pyrimidin-2-yl)benzoate (12)

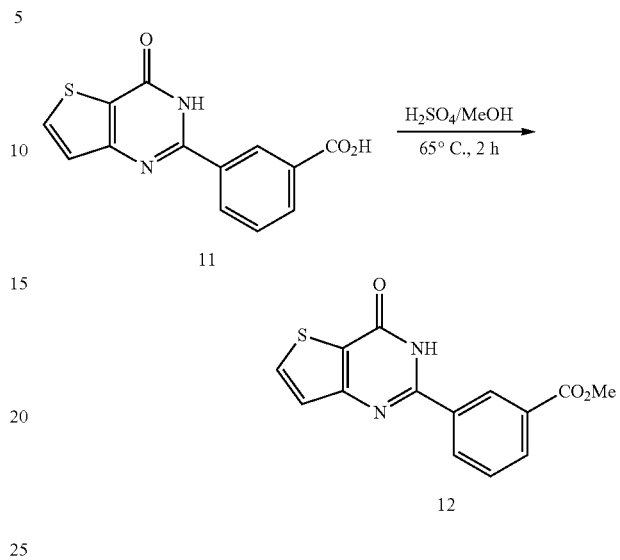

To a solution of 3-(4-oxo-3,4-dihydrothieno[3,2-d]pyrimidin-2-yl)benzoic acid (11) (205.0 g, 752.9 mmol, 1.0 equiv.) in methanol (4.1 L) was added sulfuric acid (920 g, 9.38 mol, 12.46 equiv.) at room temperature and the mixture was heated under reflux for 2 h. The progress of the reaction was monitored by TLC (Mobile phase: 5% MeOH in DCM). Most of the methanol was evaporated under reduced pressure. The residue was added to chilled saturated aqueous sodium bicarbonate (2.5 L) to pH 7. The solid was collected by filtration, washed thoroughly with water (1.7 L) and dried at 50° C. to obtain light brown solid methyl 3-(4-oxo-3,4-dihydrothieno[3,2-d]pyrimidin-2-yl)benzoate (12) (161.10 g, 74.69%).

Step 5: Methyl 3-(4-chloro-3,4-dihydrothieno[3,2-d]pyrimidin-2-yl)benzoate (13)

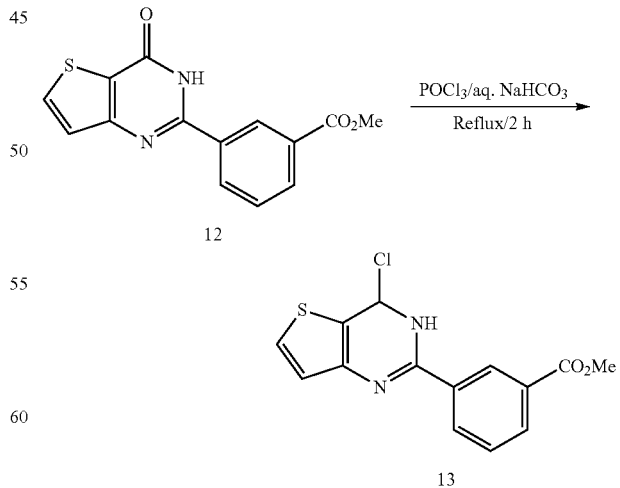

To methyl 3-(4-oxo-3,4-dihydrothieno[3,2-d]pyrimidin-2-yl)benzoate (12) (161.0 g, 562.33 mmol, 1.0 equiv.) was added POCl$_3$ (805.0 mL) and the dark mixture was heated at reflux for 2 h. The progress of the reaction was monitored by TLC (Mobile phase: 5% MeOH in DCM). Most of the phosphorus oxychloride was distilled off under reduced pressure. The oily residue was added to saturated aqueous sodium bicarbonate (3.5 L) below 20° C. and diluted with CH$_2$Cl$_2$ (8.0 L). Organic layer was separated and washed with water (3.5 L), dried using Na$_2$SO$_4$ and concentrated to obtain a light brown solid methyl 3-(4-chloro-3,4-dihydrothieno[3,2-d]pyrimidin-2-yl)benzoate (13) (115.0 g, 66.7%).

Step 6: Methyl 3-(4-morpholinothieno[3,2-d]pyrimidin-2-yl)benzoate (14)

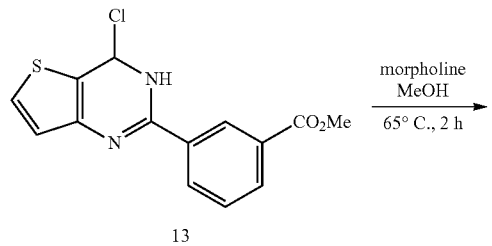

13

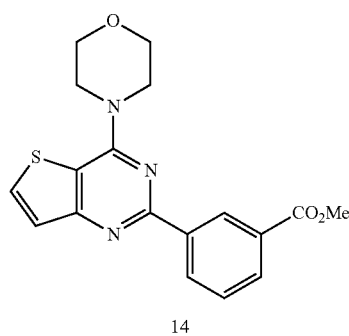

14

Morpholine (99.38 g, 1140.96 mmol, 3.5 equiv.) was added to a stirred suspension of methyl 3-(4-chloro-3,4-dihydrothieno[3,2-d]pyrimidin-2-yl)benzoate (13) (100.0 g, 325.99 mmol, 1.0 equiv.) in methanol (2.5 L). The reaction mixture was heated at reflux for 2 h. The progress of the reaction was monitored by TLC (Mobile phase: 50% ethyl acetate in n-heptane). Most of the methanol was evaporated under reduced pressure. The crude product was purified by column chromatography on silica gel (230-400 mesh size) using 20-50% EtOAc in n-heptane and then with 0-3% MeOH in DCM to afford 4-(2-(3-methoxyphenyl)thieno[3,2-d]pyrimidin-4-yl)morpholine (14) as an off white solid (93.0 g, 80.26%).

Step 7: (3-(4-Morpholinothieno[3,2-d]pyrimidin-2-yl)phenyl)methanol (15)

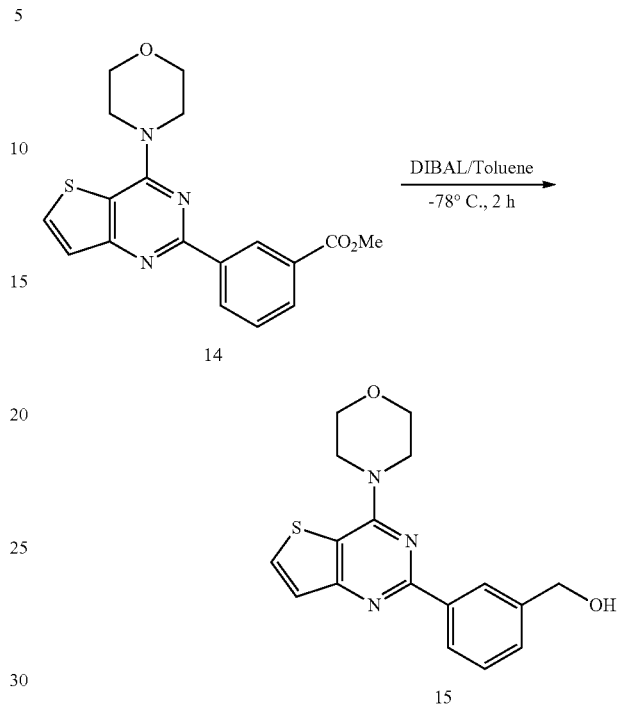

DIBAL (99.56 g, 700.08 mmol, 4.29 equiv.) was added to a solution of 4-(2-(3-methoxyphenyl) thieno[3,2-d]pyrimidin-4-yl)morpholine (14) (58.0 g, 163.19 mmol, 1.0 equiv.) in toluene (1.16 L) at −78° C. under a nitrogen atmosphere. The reaction mixture was stirred at −78° C. for 2 h. The progress of reaction was monitored by TLC (Mobile phase: 60% EtOAc in n-heptane). The reaction mixture was quenched by methanol (100 mL) at <20° C. It was then diluted with water (3.5 L) and extracted with ethyl acetate (3×2.0 L). The combined extract was washed with brine (3.5 L), dried over Na$_2$SO$_4$ and concentrated to obtain (3-(4-morpholinothieno[3,2-d]pyrimidin-2-yl)phenyl)methanol (15) as an off white solid (50.0 g, 93.6%).

Step 8: 3-(4-Morpholinothieno[3,2-d]pyrimidin-2-yl)benzyl acetate (Compound 1.015)

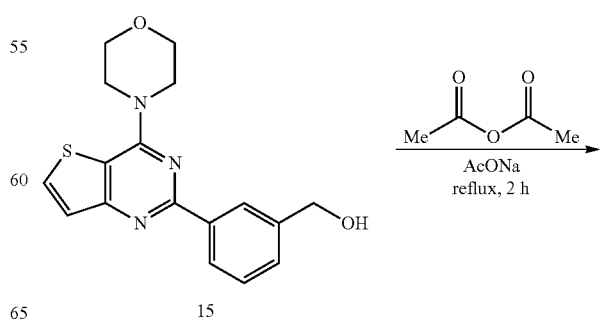

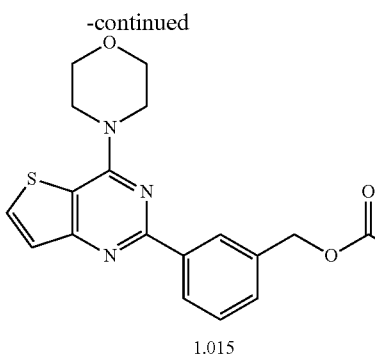

1.015

To a stirred solution of (3-(4-morpholinothieno[3,2-d]pyrimidin-2-yl)phenyl)methanol (15) (27.0 g, 82.47 mmol, 1.0 equiv.) in ethyl acetate (0.54 L) was added acetic anhydride (59.43 g, 582.24 mmol, 7.06 equiv.) and sodium acetate (33.83 g, 412.35 mmol, 5.0 equiv.) at room temperature. The reaction mixture was heated at reflux for 2 h. The progress of the reaction was monitored by TLC (Mobile phase: 60% EtOAc in n-heptane). The reaction mixture was allowed to cool to room temperature and was then diluted with water (0.9 L). The aqueous layer was extracted twice with ethyl acetate (1.25 L×2). The combined extract was washed with saturated aqueous NaHCO$_3$ (0.8 L) and brine (0.8 L) then dried over Na$_2$SO$_4$ and concentrated under reduced pressure to provide crude 3-(4-morpholinothieno[3,2-d]pyrimidin-2-yl)benzyl acetate (1.015) (27.9 g, Yield: 91.57%, HPLC area: 97.67%). Crude 1.015 (27.9 g, HPLC: 97.67%) was suspended in ethyl acetate (83.7 mL, 3 vol. equiv.) and stirred at room temperature for 2 h. The resulting solid was collected by filtration, washed with ethyl acetate (14.0 mL) and dried at room temperature to obtain 3-(4-morpholinothieno[3,2-d]pyrimidin-2-yl)benzyl acetate (1.015) (25.0 g, 82%; HPLC area: 99.25%).

Example 8: Preparation of Topical Gel Formulations

The topical gel formulations of the present invention can be prepared according to the procedure provided below. Reaction conditions and steps not provided in the procedure below would be apparent to, and known by, those skilled in the art.

Topical gel formulations were prepared using the excipients as shown in Table 2. The liquid excipients, i.e. DMSO, oleic acid, Transcutol® P, and dipropylene glycol were mixed in a 20-mL vial, by vortex agitation. The active ingredient, a compound of formula (I), for example Compound 1.002 was then added, and the vial content was sonicated for 10 minutes to dissolve the compound. The solution reached at a saturation concentration of about 105 mg/mL. Hydroxylpropyl cellulose (HPC) was added, and the vial was agitated by vortex for another ten minutes to obtain the gel formulation. The viscosity of the clear gel was measured to be in a range of about 7,000 to 10,000 centipoise (cp).

TABLE 2

Topical Gel Formulation containing Compound 1.002

| Ingredients | Function | Amount (g) | wt/wt % |
|---|---|---|---|
| DMSO | Solvent/Penetration enhancer | 3 | 30 |
| Oleic Acid (OA) | Penetration enhancer | 1 | 10 |

TABLE 2-continued

Topical Gel Formulation containing Compound 1.002

| Ingredients | Function | Amount (g) | wt/wt % |
|---|---|---|---|
| Transcutol P (2-(2-Ethoxyethoxy)ethanol) | Solvent/Penetration enhancer | 2 | 20 |
| Dipropylene glycol (DPG) | Penetration enhancer | 4 | 40 |
| Total weight of the base formulation | — | 10 | 100% |
| Hydroxylpropyl cellulose (HPC) | Gelling Agent | 0.2 | 2%[a] |
| Compound 1.002 | Active Ingredient | 1.2 | 12%[a] |

[a] the wt/wt % of HPC or Compound 1.002 is based on the weight of the base formulation.

Example 9: In Vitro Human Skin Permeation Study

Study-1: Topical Gel Formulation of Compound 1.002

The gel formulation of Example 8 was used as the donor phase to determine the permeation of Compound 1.002 through human skin and its effectiveness as a topical application. Three skin donors and three diffusion cells (for each donor) per formulation were used in the in vitro skin permeation experiments. Split thickness dermatomed (approximately at 375 µm thickness) human cadaver skin, supplied by New York Firefighters Skin Bank, NY, was used to determine the permeation rate of the tested compound (i.e., the drug) in vitro. All in vitro skin permeation studies were conducted using the Vertical Diffusion Cells assembly with consoles (Model FDC-6), and heating controllers (Logan Instruments Inc. Somerset, N.J.). Each assembly consisted of six vertical, jacketed (37° C.±0.5° C.) 12-mL Franz diffusion cells with magnetic stirrer and 1.767 cm$^2$ diffusion area.

Skin flux studies were run for a period of 48 hours. At predetermined intervals (2, 4, 8, 24 and 48 hours) after starting the experiment, the entire contents of the receiver compartment were collected for determining concentrations of the drug by HPLC. The receiver compartment was refilled with fresh receiver medium. The receiver medium was pH 7.4 phosphate buffer with 0.5 mg/ml of Oleath 20 with the saturation concentration of the drug in the receptor medium being 0.152 mg/ml. This solubility of the drug in the receiver medium was enough to ensure sink conditions throughout each collection interval.

Samples of the receptor phase were obtained at 2, 4, 8, 12, 24 and 48 h and concentrations of Compound 1.002 and 3-(4-morpholinothieno(3,2-d)pyrimidin-2-yl)phenol (metabolite of Compound 1.002, abbreviated as MTPP) were determined using a validated HPLC method. The metabolism of Compound 1.002 to MTPP takes place in the human skin by esterase enzymes.

HPLC method: Column—Gemini C-18 4.6×150 mm, 5 µm particle size; Mobile Phase—water:acetonitrile 25:75 containing 0.1% TFA; Flow Rate—1 mL/min; Detection—274 nm; Column Temperature—40° C.; and Run Time—10 min. The retention times for MTPP and Compound 1.002 were 3.9 and 7.2 minutes, respectively.

Figure 3:
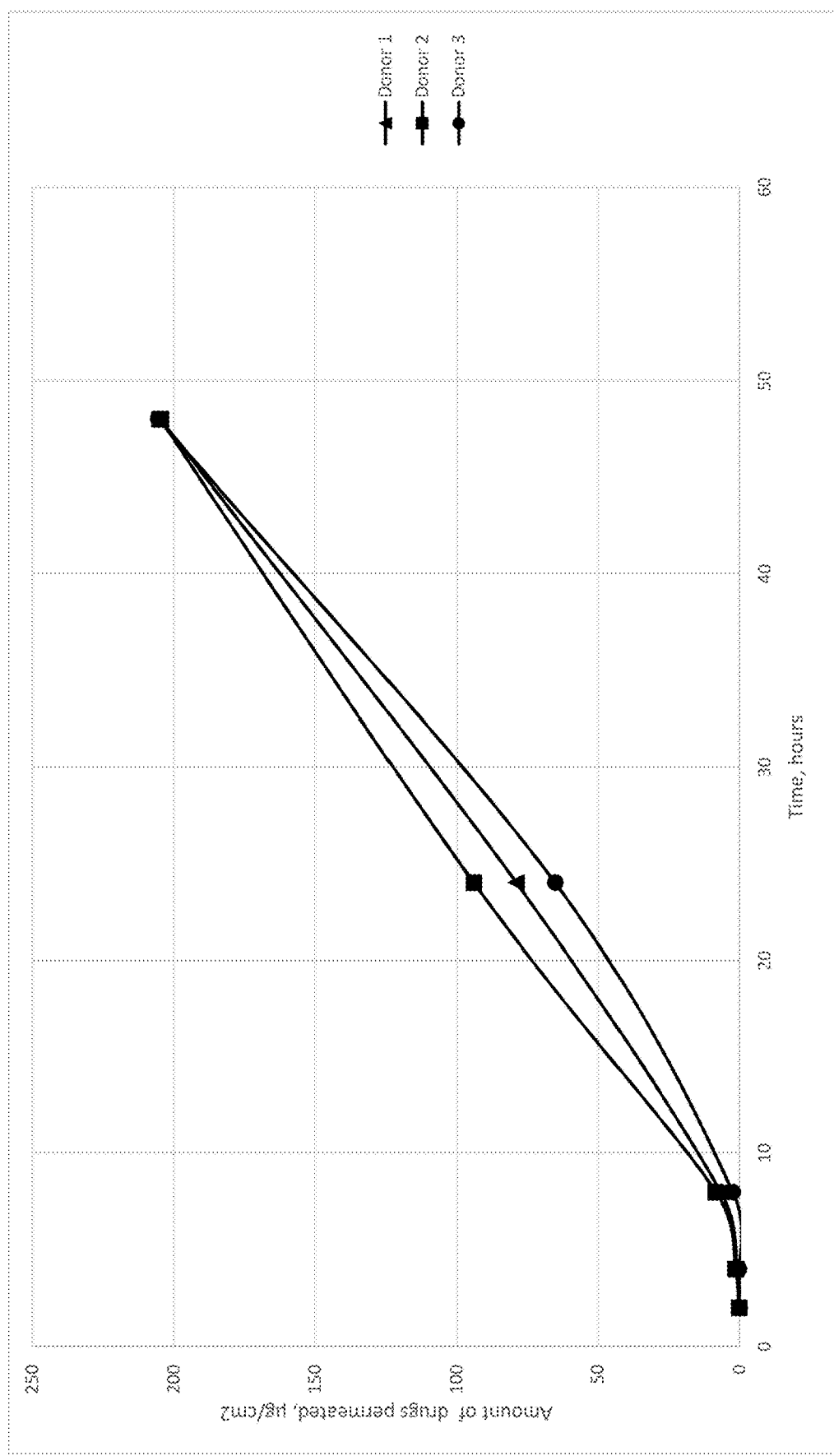
FIG. 3 shows a plot of cumulative permeation of Compound 1.002 in a topical gel formulation through human skin as a function of time.

The skin flux of drugs and cumulative amount of drugs permeated (sum of MTPP and Compound 1.002) for a period of 48 hours were calculated and are shown in Table 3. FIG. 3 represents a plot of Cumulative amount permeated versus time.

TABLE 3

Cumulative Permeation Data of Compound 1.002 through human skin (in µg/cm²)

| Donor | Time (h) | MTPP | Cmpd. 1.002 | MTPP + Cmpd. 1.002 | Hydrolysis of Cmpd. 1.002 to MTPP |
|---|---|---|---|---|---|
| Donor 1 | 2 | 0.37 | 0.00 | 0.37 | 100% |
| | 4 | 1.12 | 0.00 | 1.12 | 100% |
| | 8 | 6.68 | 0.00 | 6.68 | 100% |
| | 24 | 65.42 | 13.47 | 78.89 | 82.9% |
| | 48 | 119.80 | 85.01 | 204.81 | 58.5% |
| Donor 2 | 2 | 0.12 | 0.00 | 0.12 | 100% |
| | 4 | 1.46 | 0.00 | 1.46 | 100% |
| | 8 | 7.28 | 1.09 | 8.37 | 87.0% |
| | 24 | 78.59 | 15.44 | 94.03 | 83.6% |
| | 48 | 122.19 | 82.83 | 205.02 | 59.6% |
| Donor 3 | 2 | 0.00 | 0.00 | 0.00 | — |
| | 4 | 0.20 | 0.00 | 0.20 | 100% |
| | 8 | 2.38 | 0.00 | 2.38 | 100% |
| | 24 | 59.99 | 5.18 | 65.18 | 92.0% |
| | 48 | 134.62 | 70.87 | 205.49 | 65.5% |

Study-2: Topical Gel Formulation of Compound 1.002

Skin flux experiment of Study-1 was repeated with the same gel formulation except Compound 1.002 had a saturated concentration of 120 mg/mL. The cumulative amount of MTPP or Compound 1.002 that permeated through the skin for a 48 hour period is shown in Table 4.

TABLE 4

Cumulative Permeation Data of Compound 1.002 through human skin (in µg/cm²)

| Time (h) | MTPP | Cmpd. 1.002 | MTPP + Cmpd. 1.002 | Hydrolysis of Cmpd. 1.002 to MTPP |
|---|---|---|---|---|
| 2 | 1.33 | 0.00 | 1.33 | 100% |
| 4 | 9.17 | 0.00 | 9.17 | 100% |
| 8 | 51.85 | 0.00 | 51.85 | 100% |
| 24 | 253.97 | 0.00 | 253.97 | 100% |
| 48 | 407.48 | 78.10 | 485.58 | 83.9% |

The above Study-1 and Study-2 demonstrated that a substantial amount (e.g., 82%-100%) of Compound 1.002 permeated through the skin in the first 24-hour period was metabolized to the parent compound of 3-(4-morpholinothieno(3,2-d)pyrimidin-2-yl)phenol (abbreviated as MTPP). The first 24-hour period represents the practical in vivo application time.

Study-3: Topical Gel Formulation of MTPP and Compound 1.002

Figure 4:
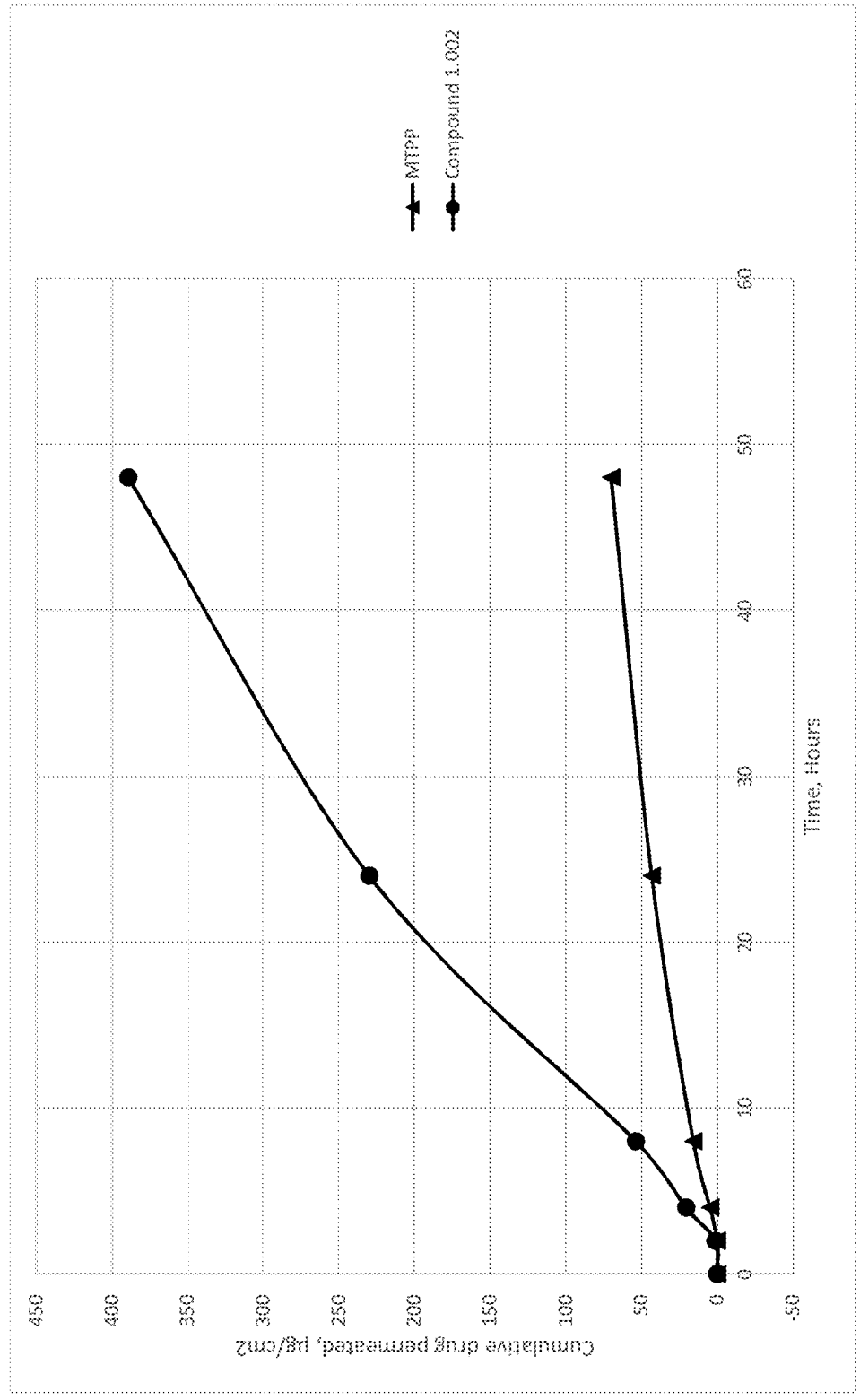
FIG. 4 shows a comparison of cumulative permeation of 3-(4-morpholinothieno(3,2-d)pyrimidin-2-yl)phenol (MTPP) and Compound 1.002 in a gel formulation through human skin.

Saturated gel formulations were prepared in accordance with the composition and procedures used in Example 8, except Compound 1.002 in one of formulations was replaced with 3-(4-morpholinothieno(3,2-d)pyrimidin-2-yl)phenol (abbreviated as MTPP). Skin flux experiments were conducted according to the procedure described in Study-1 of Example 9. The cumulative amount of MTPP or Compound 1.002 that permeated through the skin for a 48 hour period is shown in FIG. 4. It is apparent from the figure that the permeation of Compound 1.002 through human skin is about 6 times higher than that of MTPP.

Study-4: Topical Gel Formulation of MTPP and Compound 1.001

Saturated gel formulations were prepared in accordance with the composition and procedures used in Example 8, except Compound 1.002 was replaced with 3-(4-morpholinothieno(3,2-d)pyrimidin-2-yl)phenol (abbreviated as MTPP) and Compound 1.001, respectively. Skin flux experiments were conducted according to the procedure described in Study-1 of Example 9.

3-(4-morpholinothieno(3,2-d)pyrimidin-2-yl)phenol (MTPP) permeated as its intact compound. Compound 1.001, the methyl ether derivative of MTPP, was found to permeate as its intact compound in the skin flux experiments, indicating that this compound appeared not to metabolize to MTPP in the human skin. Table 5 shows the skin flux data for MTPP and Compound 1.001.

TABLE 5

Cumulative permeation data of MTPP and Compound 1.001 (in µg/cm²)

| Time (h) | MTPP | Compound 1.001 | Hydrolysis of Cmpd. 1.001 to MTPP |
|---|---|---|---|
| 2 | 0.23 | 0.0 | 0.0 |
| 4 | 4.74 | 10.2 | 0.0 |
| 8 | 15.85 | 51.8 | 0.0 |
| 24 | 43.32 | 202.1 | 0.0 |
| 48 | 70.13 | 260.4 | 0.0 |

Study-5: Topical Gel Formulation of Compound 1.006

Saturated gel formulation was prepared in accordance with the composition and procedures used in Example 8, except Compound 1.002 was replaced with Compound 1.006. Skin flux experiments were conducted according to the procedure described in Study-1 of Example 9.

Compound 1.006 was found to permeate through human skin and metabolize into MTPP, by the esterase enzymes in the skin. Tables 6A and 6B show the skin permeation data by two separate experiments. The saturated concentration of Compound 1.006 in the formulation for results presented in Table 6B was 215 mg/mL.

TABLE 6A

Cumulative permeation data of Compound 1.006 (in µg/cm²)

| Time (h) | MTPP | Compound 1.006 | Sum of MTPP and Compound 1.006 | Hydrolysis of Cmpd. 1.006 to MTPP |
|---|---|---|---|---|
| 2 | 17.8 | 0.0 | 17.8 | 100% |
| 4 | 26.0 | 0.0 | 26.0 | 100% |
| 8 | 29.7 | 1.0 | 30.7 | 96.7% |
| 24 | 50.3 | 13.0 | 63.3 | 79.5% |
| 48 | 139.4 | 30.5 | 169.9 | 82.0% |

TABLE 6B

Cumulative permeation data of Compound 1.006 (in µg/cm$^2$)

| Time (h) | MTPP | Compound 1.006 | Sum of MTPP and Compound 1.006 | Hydrolysis of Cmpd. 1.006 to MTPP |
|---|---|---|---|---|
| 2 | 2.3 | 0.0 | 2.3 | 100% |
| 4 | 7.0 | 0.5 | 7.5 | 93.3% |
| 8 | 22.4 | 0.5 | 22.9 | 97.8% |
| 24 | 58.6 | 0.6 | 59.2 | 98.9% |
| 48 | 100.9 | 0.6 | 101.5 | 99.4% |

According to the sum of drugs (i.e., MTPP and Compound 1.006), it was found that the total amount of compound 1.006 permeated was noticeably less than that of compound 1.002.

Study-6: Topical Gel Formulation of Compound 1.012

Saturated gel formulation was prepared in accordance with the composition and procedures used in Example 8, except Compound 1.002 was replaced with Compound 1.012. The saturated concentration of Compound 1.012 in the formulation was 58 mg/mL. Skin flux experiments were conducted according to the procedure described in Study-1 of Example 9.

Compound 1.012 was found to permeate through human skin and completely metabolize into MTPP, by the esterase enzymes in the skin. Table 7 show the skin permeation data.

TABLE 7

Cumulative permeation data of Compound 1.012 (in µg/cm$^2$)

| Time (h) | MTPP | Compound 1.012 | Sum of MTPP and Compound 1.012 | Hydrolysis of Cmpd. 1.012 to MTPP |
|---|---|---|---|---|
| 2 | 0.08 | 0.0 | 0.08 | 100% |
| 4 | 1.59 | 0.0 | 1.59 | 100% |
| 8 | 8.41 | 0.0 | 8.41 | 100% |
| 24 | 33.95 | 0.0 | 33.95 | 100% |
| 48 | 57.58 | 0.0 | 57.58 | 100% |

A stability study of the gel formulation including compound 1.012 was conducted at 80° C. Compound 1.012 in the formulation was found to be quite stable: 99% relative purity after 5 days and 96% relative purity after 10 days at 80° C. by HPLC analysis.

According to the sum of drugs (i.e., MTPP and Compound 1.012), it was found that the total amount of compound 1.012 permeated was noticeably less than that of compound 1.002.

Study-7: Topical Gel Formulations of Compounds 1.008, 1.011, and 1.014

A saturated gel formulation of Compound 1.008, 1.011, or 1.014 was prepared respectively using a similar procedure of Example 8. Saturation solubility was determined by observing miscibility. Skin flux experiments were conducted according to the procedure described in Study-1 of Example 9.

The skin permeation of compounds 1.008, 1.011, and 1.014 in the gel formulation were found to be less than 10% as compared to the permeation of Compound 1.002.

A stability study of a gel formulation including Compound 1.008, 1.011, or 1.014 was conducted at 80° C. All three compounds were found to be very stable at 80° C. for 10 days.

Example 10: In Vitro Skin Permeation Study—Human vs. Mouse Skin

The gel formulation of Example 8 was used to determine the skin permeation through human and mouse skin. It is important to understand the permeation difference between the two types of skin, because mouse skin is used extensively in toxicology studies as well as in early in vivo studies. The skin permeation study was performed in accordance with the method as described in Example 9.

Figure 5:
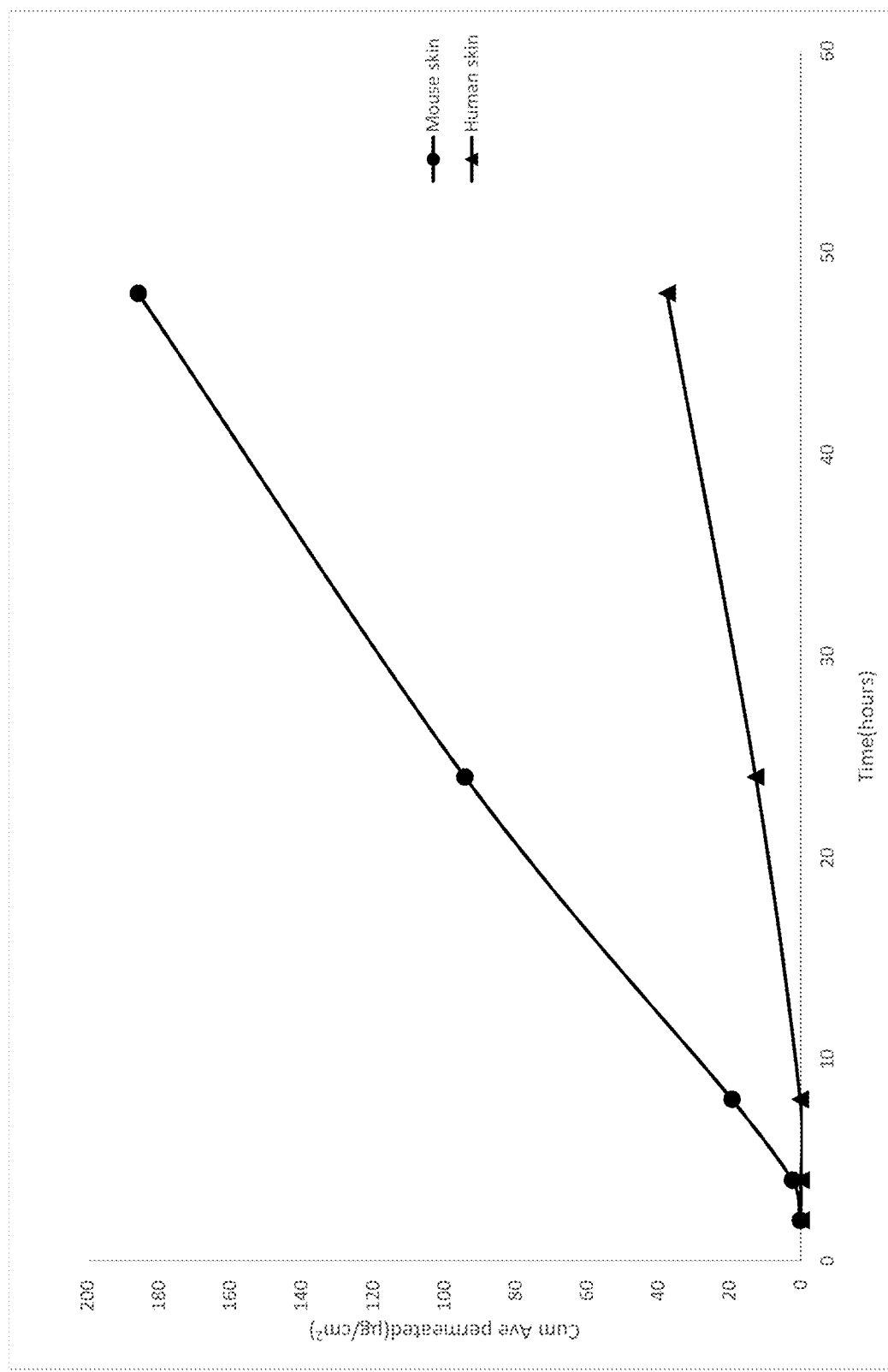
FIG. 5 shows a comparison of cumulative permeation of Compound 1.002 in a topical gel formulation through human and mouse skins.

FIG. 5 shows a comparison of skin permeation of Compound 1.002 through human and mouse skins for a period of 48 hours. Permeation through mouse skin of Compound 1.002 was approximately three times higher than the permeation through human skin, as shown in FIG. 5. The metabolism of Compound 1.002 to MTPP in both skin types proceeded equally well.

Example 11: Ethanol-Based Topical Gel Formulation

A topical gel formulation including Compound 1.002 and mainly ethanol was prepared according to the procedure described in Example 8, using the following composition:

| Ingredients | Amount (g) | wt/wt % |
|---|---|---|
| Ethanol | 9 | 90 |
| Oleic Acid (OA) | 0.2 | 2 |
| Dipropylene glycol (DPG) | 0.8 | 8 |
| Total weight of the base formulation | 10 | 100% |
| Hydroxylpropyl cellulose (HPC) | 0.2 | 2$^a$ |
| Compound 1.002 | 0.36 | 3.6$^a$ |

$^a$the wt/wt % of HPC or Compound 1.002 is based on the weight of the base formulation.

Skin permeation experiments were performed according to the procedure given in Example 9, and the results are shown in Table 8.

TABLE 8

Cumulative Permeation Data of Compound 1.002 in Ethanol-based Formulation (in µg/cm$^2$)

| Time (hours) | Skin Flux |
|---|---|
| 4 | 6.15 |
| 8 | 8.75 |
| 24 | 53.74 |
| 48 | 73.62 |

Example 12: Preparation of Topical Solution Formulations

A solution formulation was prepared, similar to the gel formulations as described in Example 8, without a thickening agent. The compositions of the formulation are listed in Table 9. The viscosity of the solution was 13.4 cp and it can be used as a topical spray or lotion.

TABLE 9

Solution formulation of Compound 1.002

| Ingredients | Amount (g) | wt/wt % |
|---|---|---|
| DMSO | 3 | 30 |
| Oleic Acid (OA) | 1 | 10 |
| Transcutol P (2-(2-Ethoxyethoxy)ethanol) | 2 | 20 |
| Dipropylene glycol (DPG) | 4 | 40 |
| Total weight of the base formulation | 10 | 100% |
| Tocopherol | 0.1 | 1.0[a] |
| Compound 1.002 | 0.30 | 3.0[a] |

[a] the wt/wt % of tocopherol or Compound 1.002 is based on the weight of the base formulation.

Example 13: Reservoir Transdermal Patches for Delivery of Compounds

Figure 6:
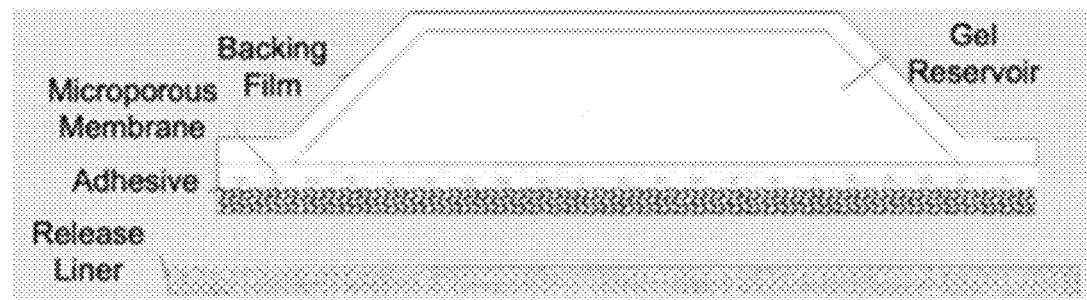
FIG. 6 shows a liquid reservoir transdermal patch system.

A liquid reservoir transdermal patch system, as shown in FIG. 6, can be fabricated and used to deliver 3-(4-morpholinothieno(3,2-d)pyrimidin-2-yl)phenol (abbreviated as MTPP) or compounds of formula (I). Transdermal patches can be used to deliver drugs up to 3.5 or 7 days from a single patch application, as compared to topical applications useful for a single day delivery.

Study-1: 3-(4-morpholinothieno(3,2-d)pyrimidin-2-yl)phenol

The following gel formulation having compositions as shown in Table 10 was prepared according to Example 8, and incorporated into the reservoir patch system.

TABLE 10

Gel formulation of MTPP for Use in Reservoir Patch

| Ingredients | Amount (g) | wt/wt % |
|---|---|---|
| DMSO | 15.0 | 30 |
| Oleic Acid (OA) | 1.0 | 2 |
| Transcutol P (2-(2-Ethoxyethoxy)ethanol) | 14.0 | 28 |
| Dipropylene glycol (DPG) | 20.0 | 40 |
| Total weight of the base formulation | 50.0 | 100% |
| Hydroxylpropyl cellulose (HPC) | 2.0 | 4 |
| MTPP | 3.0 | 6[a] |

[a] the wt/wt % of HPC or MTPP is based on the weight of the base formulation.

Figure 7:
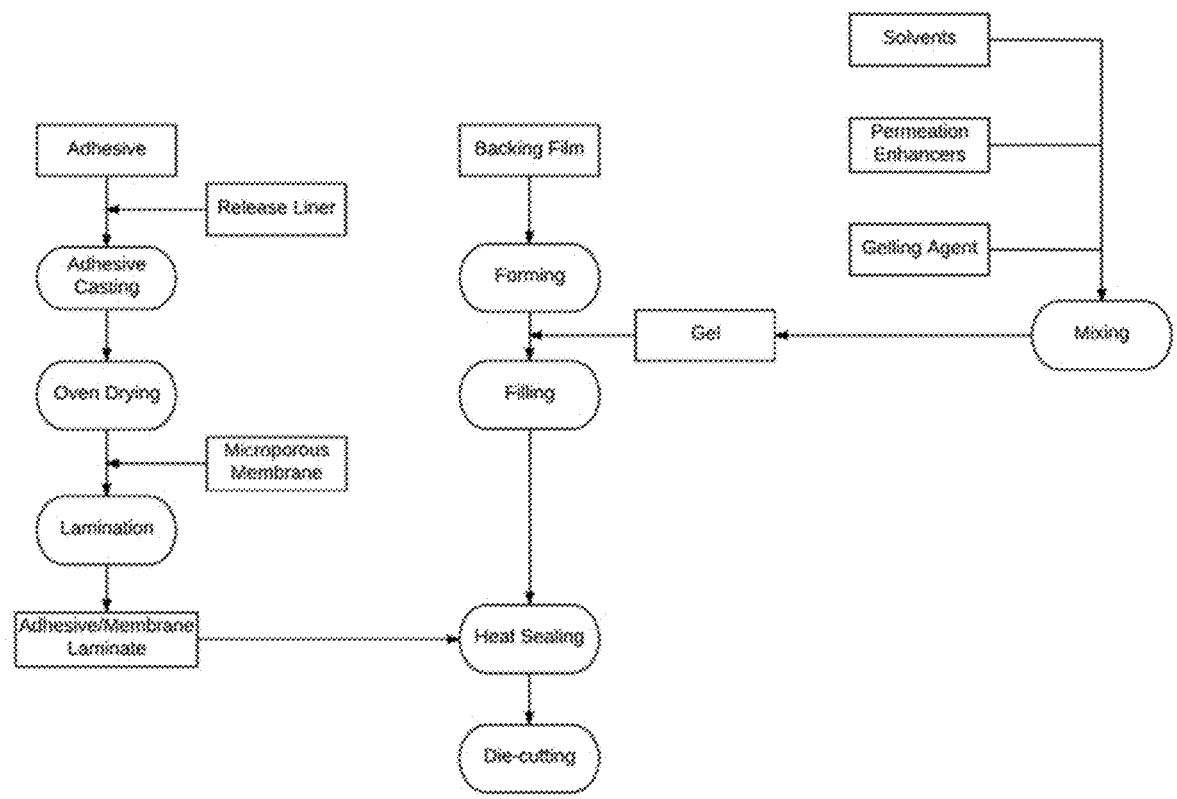
FIG. 7 represents a flow diagram of the fabrication process for the preparation of transdermal liquid reservoir patches.

Patches using the gel formulation with compositions of Table 10 were prepared in accordance with the process shown in FIG. 7. In summary the process includes: a) the preparation of the gel formulation; b) the preparation of the backing film including formation, filling and heat sealing of the patch; c) the preparation of the pressure sensitive adhesive layer; and d) the lamination of the separate layers and die-cutting of the individual patches.

Figure 8:
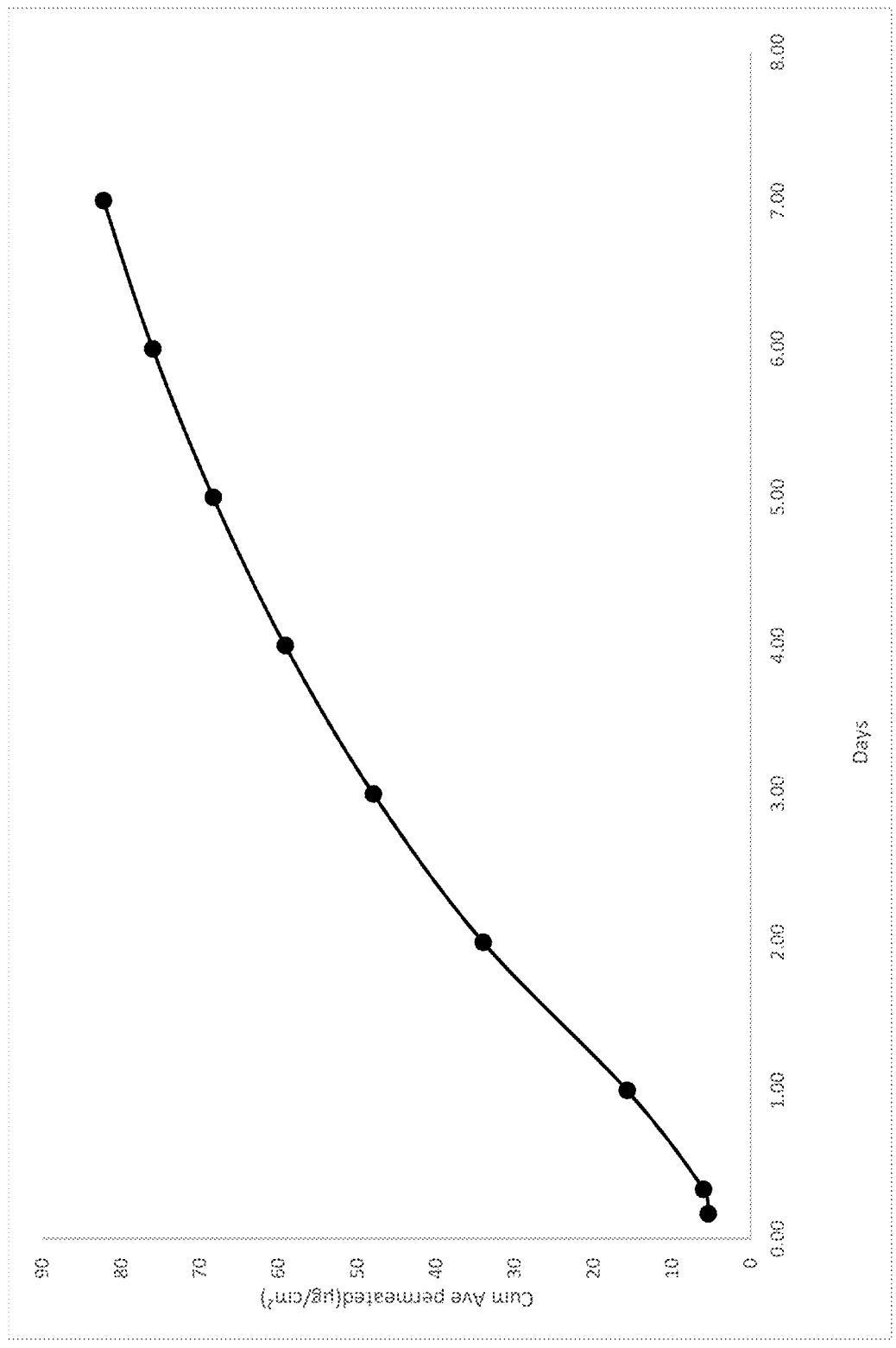
FIG. 8 shows a plot of cumulative permeation of 3-(4-morpholinothieno(3,2-d)pyrimidin-2-yl)phenol through human skin over a period of 7 days via a transdermal liquid reservoir patch.

FIG. 8 shows the obtained MTPP skin permeation data over a period of 7 days via the liquid transdermal reservoir patch containing the gel formulation of Table 10.

Study-2: Compound 1.002

Liquid reservoir transdermal patches of FIG. 6 were prepared and used for the study of delivery of Compound 1.002. The transdermal patches were used to deliver Compound 1.002 in vitro through human skin for 7 days from a single patch application. The following gel formulation having composition as shown in Table 11 was prepared according to Example 8 and incorporated into the reservoir patch system.

TABLE 11

Gel formulation of Compound 1.002 for Use in Reservoir Patch

| Ingredients | Amount (g) | wt/wt % |
|---|---|---|
| DMSO | 3 | 30 |
| Oleic Acid (OA) | 1 | 10 |
| Transcutol P (2-(2-Ethoxyethoxy)ethanol) | 2 | 20 |
| Dipropylene glycol (DPG) | 4 | 40 |
| Total weight of the base formulation | 10 | 100% |
| Hydroxylpropyl cellulose (HPC) | 0.2 | 2[a] |
| Compound 1.002 | 0.95 mg | 93 mg/mL[b] |

[a] the wt/wt % of HPC is based on the weight of the base formulation, and
[b] the concentration of Compound 1.002 is based on 1 mL of the base formulation.

Patches using the gel formulation having compositions of Table 11 were prepared in accordance with the process shown in FIG. 7. The patch was 1.8 cm$^2$ in size containing 0.3 mL of the gel formulation. The backing layer of the patch was Scotchpak® 9723, which is a laminate of polyester and polyethylene commonly used in transdermal patches. The controlling membrane was SOLUPOR® 10P05A, which is a highly porous (up to 90% porous) Ultra High Molecular Weight Polyethylene membrane with controlled pore size. The pressure sensitive adhesive in contact with the human skin was Scotchpak® 9723, which is a non-crosslinked acrylate copolymer with no functional groups.

Figure 9:
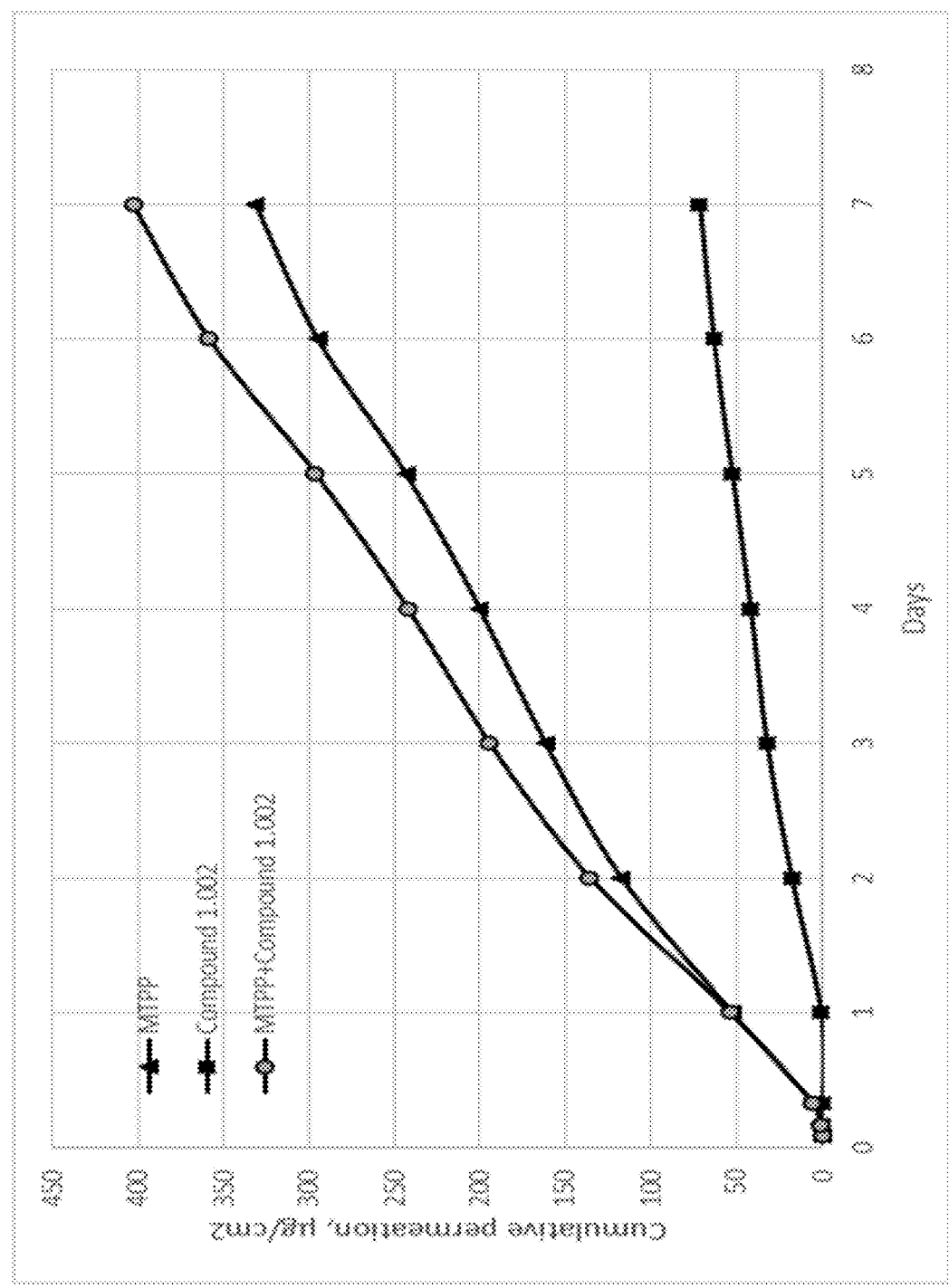
FIG. 9 shows a plot of cumulative permeation of Compound 1.002 through human skin over a period of 7 days via a transdermal liquid reservoir patch.

FIG. 9 shows the obtained skin permeation data of Compound 1.002 over a period of 7 days via the liquid transdermal reservoir patch containing the gel formulation of Table 11. Compound 1.002 was confirmed to metabolize to MTPP by estarases as it permeates through the human skin. In this study, it was found that approximately 85% of Compound 1.002 metabolized to MTPP after permeating through the human skin.

Figure 10:
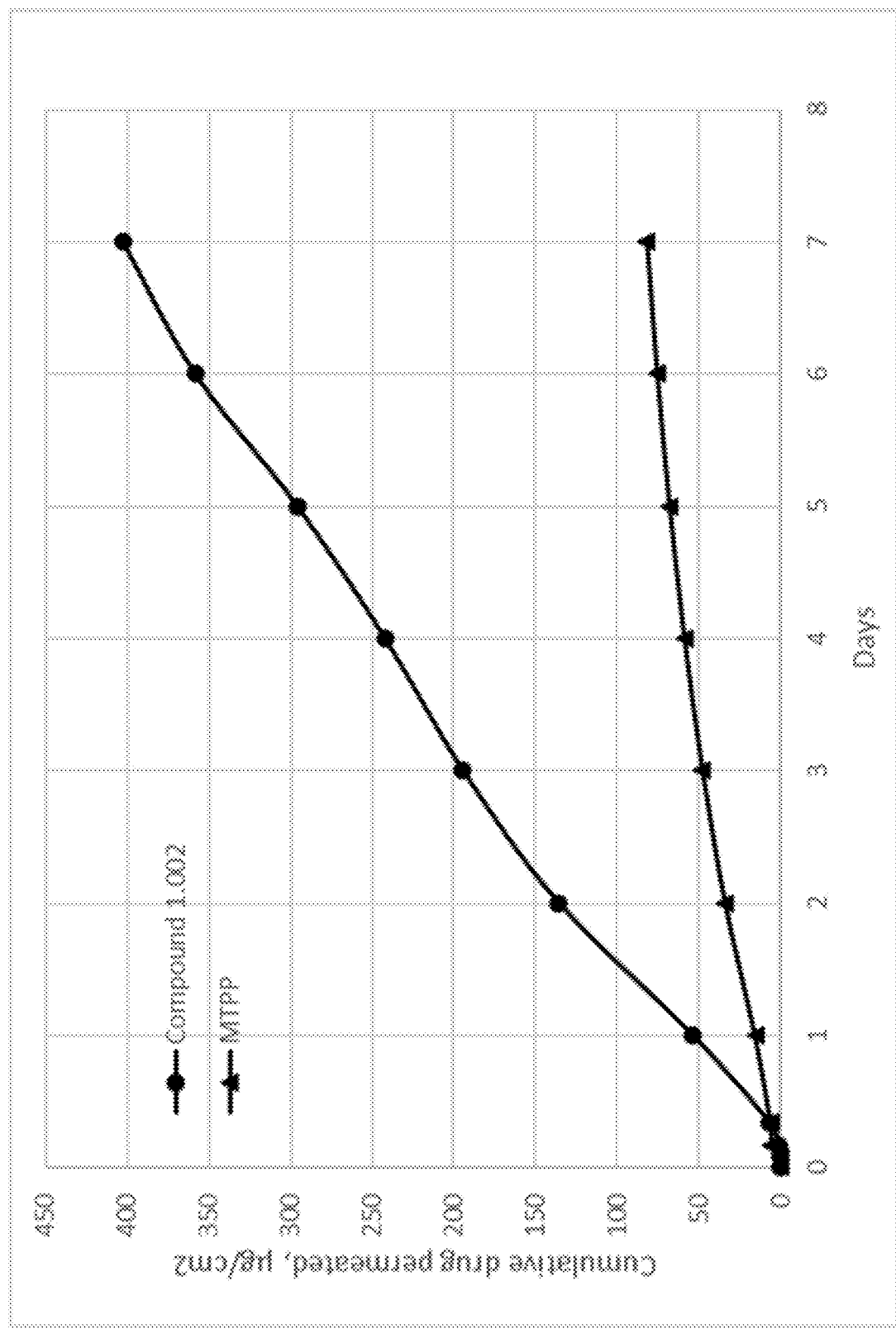
FIG. 10 shows a comparison of cumulative permeation of 3-(4-morpholinothieno(3,2-d)pyrimidin-2-yl)phenol and Compound 1.002 through human skin over a period of 7 days via a transdermal liquid reservoir patch.

FIG. 10 shows a comparison of human skin permeation of MTPP and Compound 1.002 from transdermal reservoir patches.

Example 14: In Vitro Human Skin Permeation—Effect of Enhancers

Figure 11:
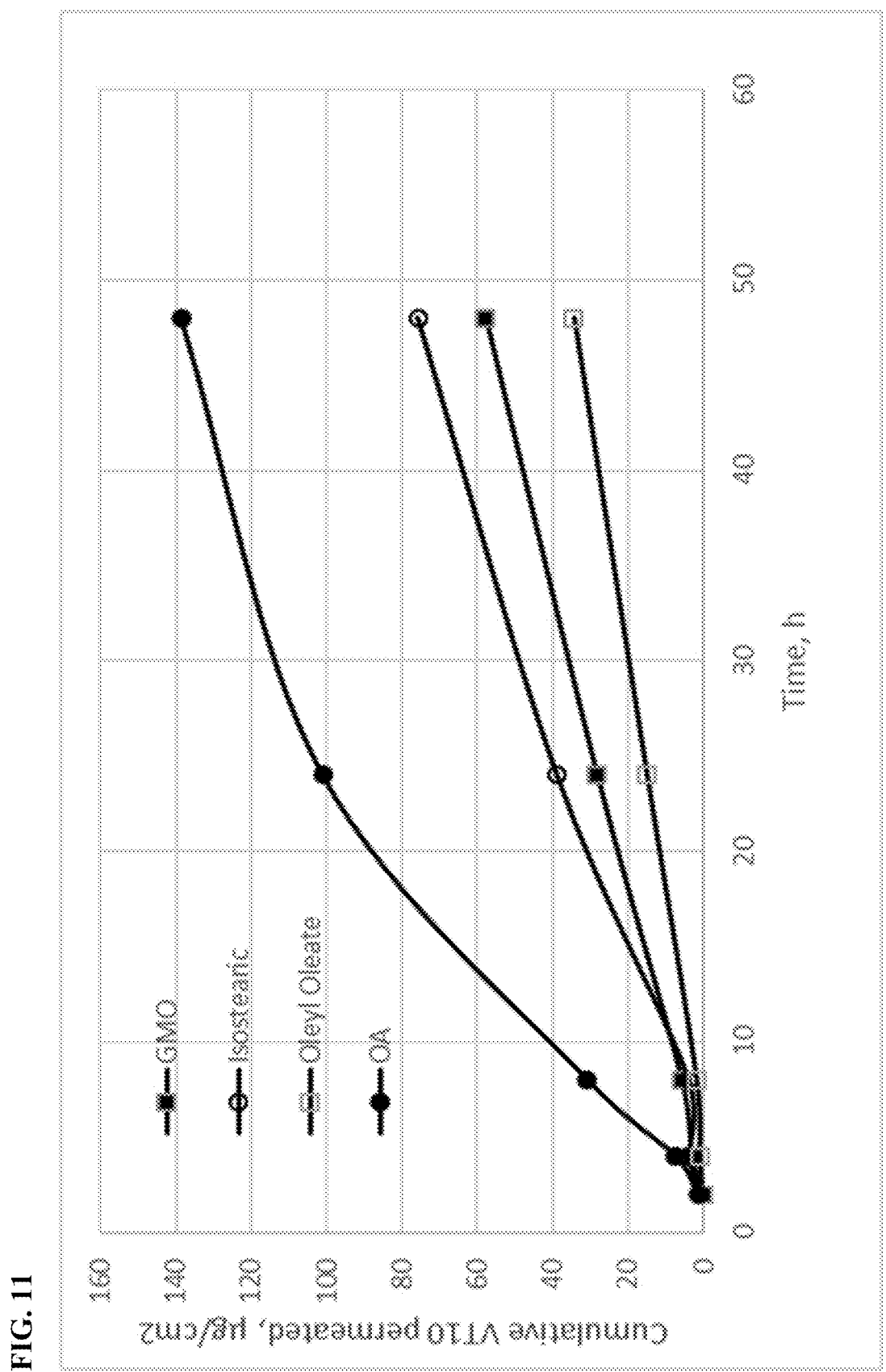
FIG. 11 shows the effect of glycerol monooleate, oleyl oleate, or isostearic acid as compared to oleic acid in the gel formulation to the skin flux of Compound 1.002 through human skin.

Study-1: Glycerol Monooleate, Oleyl Oleate, and Isostearic Acid vs. Oleic Acid The 10% oleic acid (OA) in the gel formulation of Example 8 was replaced with other skin permeation enhancers such as 10% glycerol monooleate, 10% oleyl oleate, and 10% isostearic acid; and the skin permeation was obtained using the procedure as described in Example 9. Results of the study are shown in FIG. 11.

Study-2: Neodecanoic Acid or Isostearic Acid vs. Oleic acid

Figure 12:
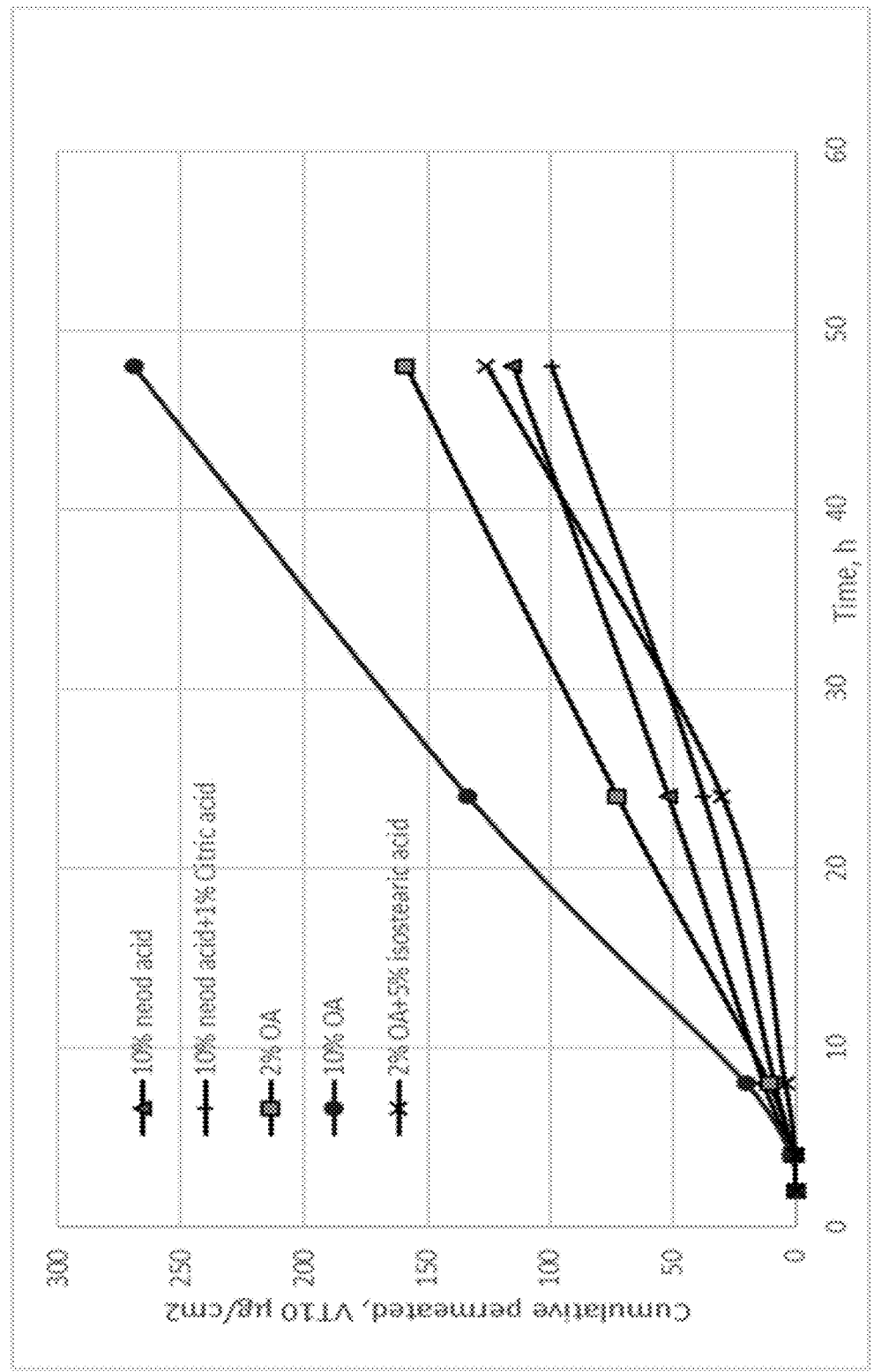
FIG. 12 shows the effect of neodecanoic acid or isostearic acid as compared to oleic acid in the gel formulation to the skin flux of Compound 1.002 through human skin.

The 10% oleic acid (OA) in the gel formulation of Example 8 was replaced with other skin permeation enhancers such as 10% neodecanoic acid (NA), 10% neodecanoic acid (NA)+1% citric acid, 2% oleic acid, and 2% oleic acid+5% isostearic acid; and the skin permeation was obtained using the procedure as described in Example 9. Results of the study are summarized in Table 12 and FIG. 12.

TABLE 12

Cumulative Permeation Data of Compound 1.002 (in μg/cm2) vs. Enhancer

| | Example 14-2A | Example 14-2B | Example 14-2C |
|---|---|---|---|
| Enhancer | 10% NA | 10% NA + 1% Citric acid | 2% OA |
| | | Sum of MTPP and Compound 1.002 | |
| Flux at 24 h | 51.9 | 37.6 | 112.2 |
| Flux at 48 h | 115.1 | 99.3 | 217.5 |

Example 15: In Vitro Human Skin Permeation—Effect of Oleic Acid

Figure 13:
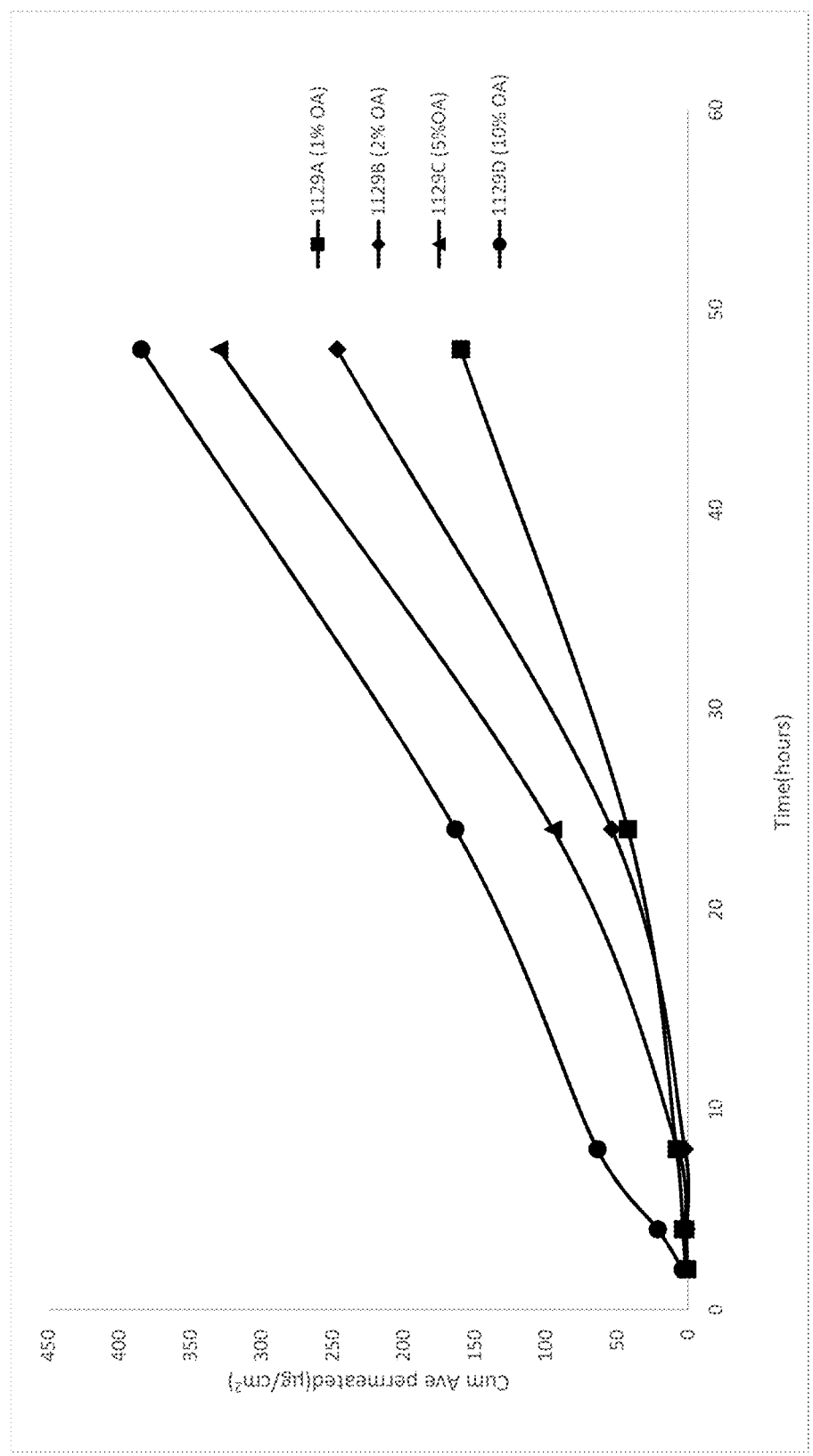
FIG. 13 shows the effect of oleic acid in the gel formulation to the skin flux of Compound 1.002 through human skin.

Four topical gel formulations of Compound 1.002 were prepared according to Example 8, in which 1%, 2%, 5% and 10% oleic acid were used, respectively. The formulation with 10% oleic acid had the same compositions as shown in Table 2. The other formulations were modifications of the 10% formulation with all ingredients reduced proportionally to take into account the lower amounts of oleic acid. Solubility of Compound 1.002 in all formulations was determined and thereafter all formulations as prepared were considered as saturated gel formulations. Majority of Compound 1.002 metabolized to MTPP, similar to the above examples as shown. The permeation data of Compound 1.002 in the above four formulations are shown in FIG. 13. It is clear that the observed flux of Compound 1.002 through human skin increases as the increase of the amount of oleic acid in the gel formulation.

Example 16: In Vitro Human Skin Permeation—Effect of Oleic Acid and Oleyl Alcohol Topical Gel formulations 16A, 16B, and 16C including Compound 1.002 were prepared according to Example 8. The compositions of the respective formulations and the amount of Compound 1.002 in each formulation are shown in Table 13. Solubility of Compound 1.002 in all three formulations reached saturation.

TABLE 13

Gel formulations

| | Formulation | | |
|---|---|---|---|
| | 16A | 16B | 16C |
| Ingredients | Amount (wt %) | | |
| DMSO | 33 | 30 | 30 |
| Oleic Acid (OA) | 2 | 10 | — |
| Oleyl alcohol | — | — | 10 |
| Transcutol P (2-(2-Ethoxyethoxy)ethanol) | 22 | 20 | 20 |
| Dipropylene glycol (DPG) | 43 | 40 | 40 |
| Total weight of the base formulation | 100% | 100% | 100% |
| Hydroxylpropyl cellulose (HPC) | 2 | 2 | 2 |
| Compound 1.002 | 10 | 9 | 9 |

Figure 14:
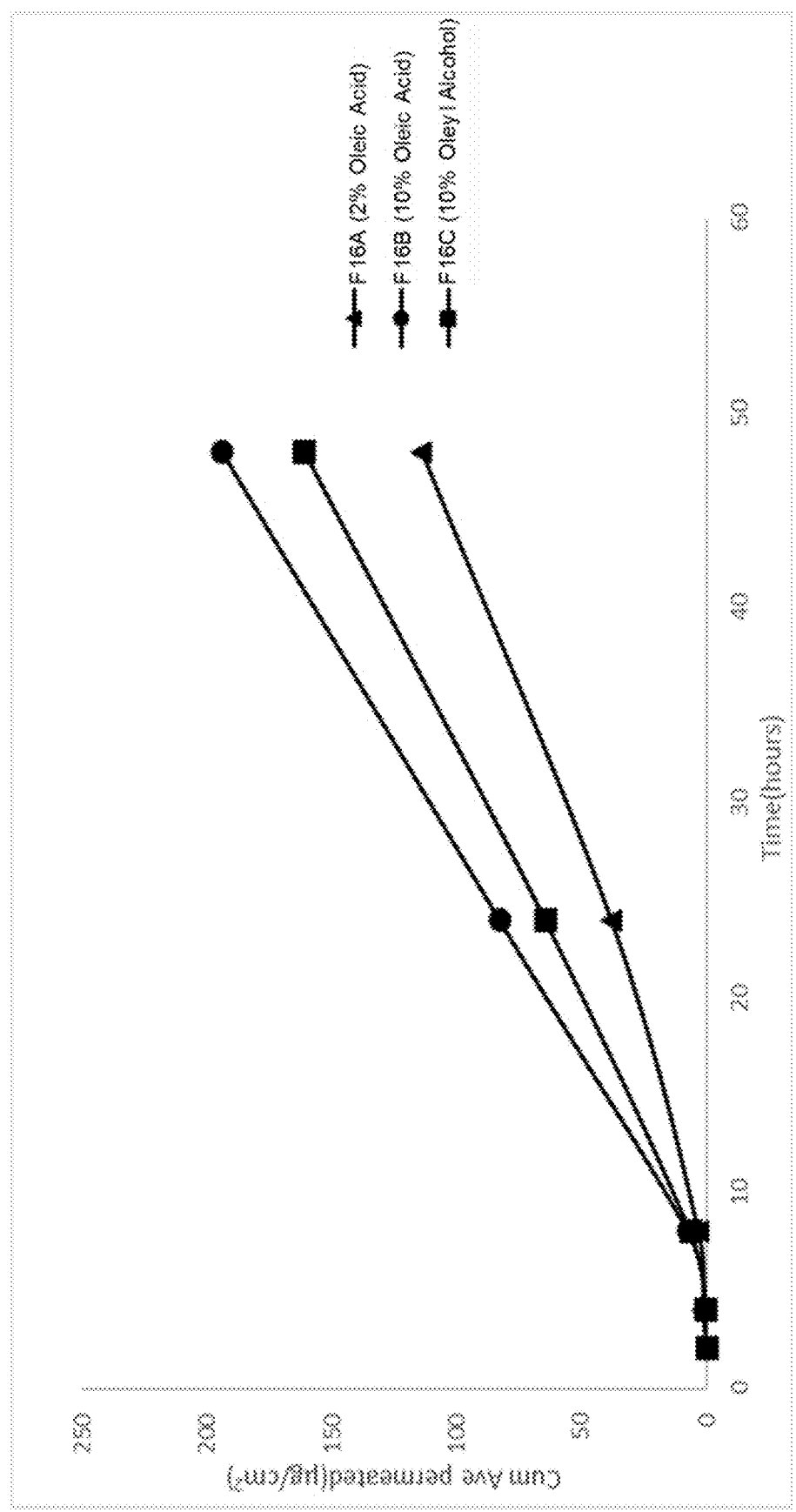
FIG. 14 shows the effect of oleic acid and oleyl alcohol in the gel formulation to the skin flux of Compound 1.002 through human skin.

The skin permeation from each of the three formulations as a function of time was obtained using procedure as described in Example 9. The permeation data as represented by the total amount of permeated (MTPP+Compound 1.002) are presented in FIG. 14. At the 24 hour time point, about 10% of the total amount of (MTPP+Compound 1.002) permeated was Compound 1.002 for three formulations. It is clear from the graphs that the formulation 16B containing 10% oleic acid performed superior to other two formulations. At 24 hours, the cumulative permeation of Compound 1.002 in formulation 16B was about 20% higher than that of the formulation 16C containing 10% oleyl alcohol.

Example 17: Topical Gel Formulation Having a Combination of Glycols

Topical gel formulation including a combination of DPG and PEG400 was prepared using the excipients as shown in Table 14 according to the procedure of Example 8, except PEG400 was also mixed with other excipients.

TABLE 14

Topical Gel Formulation of Compound 1.002 Including DPG and PEG400

| Ingredients | wt/wt % 17A | wt/wt % 17B |
|---|---|---|
| DMSO | 33 | 30 |
| Oleic Acid (OA) | 2 | — |
| Oleyl alcohol | — | 10 |
| Transcutol P (2-(2-Ethoxyethoxy)ethanol) | 22 | 20 |
| Dipropylene glycol (DPG) | 5 | 5 |
| PEG400 | 38 | 35 |
| Total weight of the base formulation | 100% | 100% |
| Hydroxylpropyl cellulose (HPC) | 2%[a] | 2%[a] |
| Compound 1.002 | 12%[a] | 12%[a] |

[a] the wt/wt % of HPC or Compound 1.002 is based on the weight of the base formulation.

The skin permeation study was performed in accordance with the method as described in Example 9.

Figure 15:
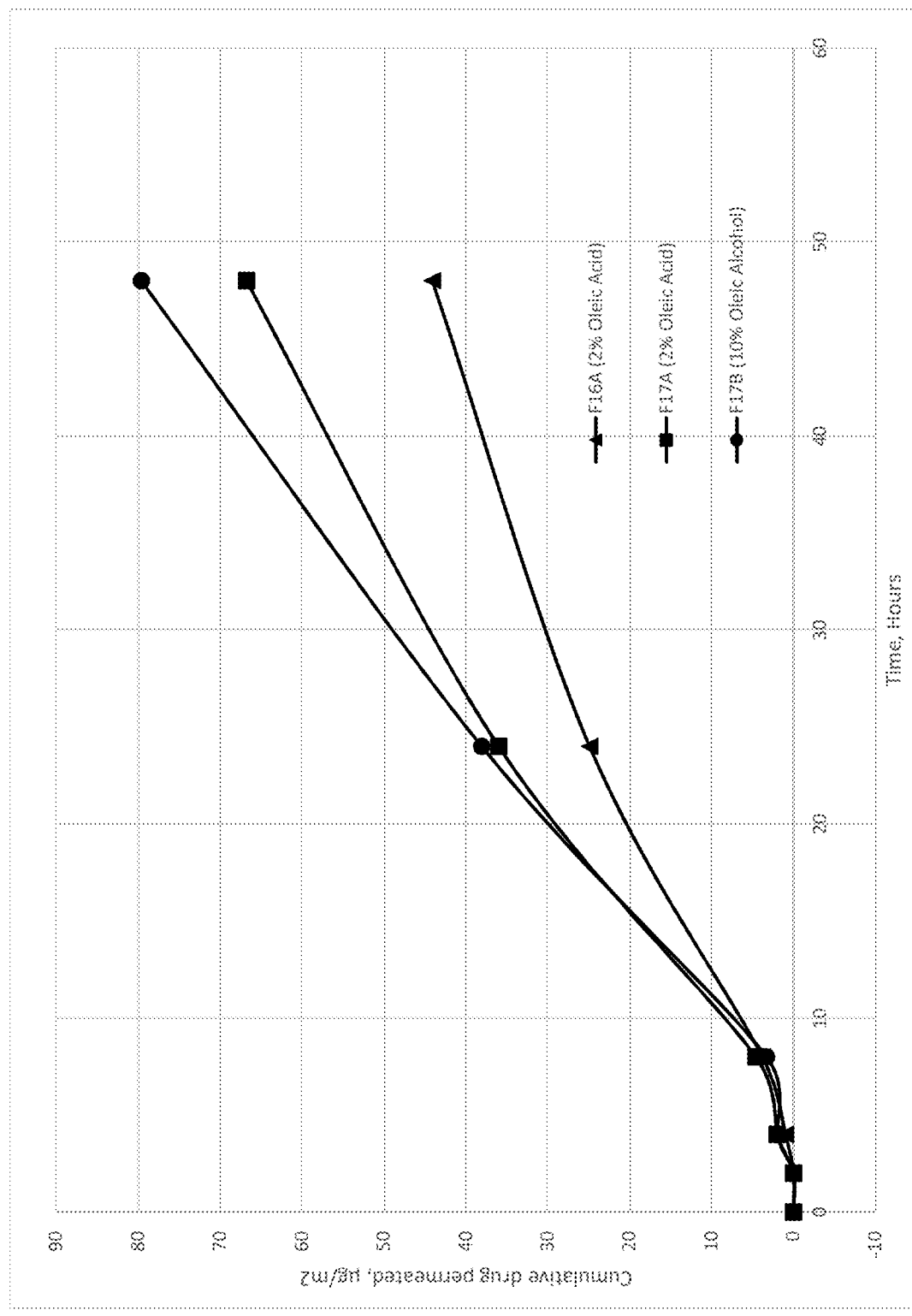
FIG. 15 shows a comparison of cumulative permeation of Compound 1.002 in gel formulations having a combination of glycols.

FIG. 15 shows a comparison of skin permeation with the gel formulation (2% oleic acid) of Example 16, 16A (2% oleic acid). It is clear from the graphs that both formulations 17A and 17B including PEG400 performed superior to the formulation 16A including DPG only. At 24 hours, formulation 17A having 2% oleic acid performed comparable to formula 17B having 10% oleyl alcohol.

Example 18: Accelerated Stability Study of Topical Gel Formulation

Study-1: Gel Formulation of Compound 1.002, 1.012, or 1.006

Topical gel formulations were prepared using excipients as shown in Table 2 according to Example 8, in which Compounds 1.002, 1.012, and 1.006 were used as the active ingredient, respectively. These gel formulations were subjected to stability study at 80° C. for 10 days. Stability under the condition of at 80° C. for 10 days is expected to be approximately equivalent to the stability for three (3) years at room temperature. A relative purity of the tested compound after being exposed for 5 days and 10 days at 80° C. was determined by HPLC, as compared to its initial purity (at day 0). Table 15 shows stability data of the tested compound in each formulation.

TABLE 15

Results of Stability Study at 80° C.

| | Day 0 | Day 5 | Day 10 |
|---|---|---|---|
| Tested Compound | Relative Purity | | |
| 1.002 | 100% | 96% | 94% |
| 1.012 | 100% | 99% | 96% |
| 1.006 | 100% | 94% | 92% |

Study-2: Gel Formulation of Compound 1.008, 1.011, or 1.014

Topical gel formulations were prepared using excipients as shown in Table 2 according to Example 8, in which Compounds 1.008, 1.011, and 1.014 were used as the active ingredient, respectively. Saturation solubility was determined by observing miscibility.

Accelerated stability studies at 80° C. were conducted for each of the formulations and all three compounds were found to be very stable at 80° C. for 10 days, as shown in Table 16 below. The values shown in the table are percent hydrolysis of the respective compounds to the parent compound MTPP.

TABLE 16

Stability of Gel Formulations of Compounds 1.008, 1.011, and 1.014

| Time point (days) | Compound 1.008 formulation | Compound 1.011 formulation | Compound 1.014 formulation |
|---|---|---|---|
| 0 | 0.00% | 0.09% | 0.00% |
| 3 | 0.20% | 0.18% | 1.32% |
| 5 | 0.28% | 0.24% | 2.09% |
| 7 | 0.39% | 0.33% | 2.43% |
| 10 | 0.56% | 0.43% | 2.94% |

Study-3: Effect of Oleic Acid

Topical gel formulations of Compound 1.002 were prepared using excipients as shown in Table 2 according to Example 8, in which the content of oleic acid varied at 1%, 2%, 5%, and 10%, respectively. These gel formulations were subjected to stability study at 80° C. for 10 days, which is expected to be approximately equivalent to the stability for three (3) years at room temperature. A purity of the tested compound on day 0, 5, 7, and 10 at 80° C. was determined by HPLC. The detected impurity of the tested compound appears to be the hydrolysis product, as MTPP. Table 17 represents stability data of Compound 1.002 in topical formulations having oleic acid at various contents.

TABLE 17

Stability Data of Compound 1.002 in Topical Formulations vs. Oleic Acid % at 80° C.

| Formulation ID | Oleic Acid (wt/wt %) | Purity of Compound 1.002 (%) | | | | Relative Purity of Compound 1.002 (%) | | | |
|---|---|---|---|---|---|---|---|---|---|
| | | Day 0 | Day 5 | Day 7 | Day 10 | Day 0 | Day 5 | Day 7 | Day 10 |
| 1123A | 1% | 99.71 | 99.20 | 98.88 | 98.92 | 100 | 99.5 | 99.2 | 99.2 |
| 1123B | 2% | 99.78 | 99.95 | 98.67 | 98.15 | 100 | 100 | 98.9 | 98.4 |
| 1123C | 5% | 99.78 | 98.13 | 97.51 | 96.75 | 100 | 98.3 | 97.7 | 97.0 |
| 1123D | 10% | 99.71 | 96.92 | 95.65 | 93.83 | 100 | 97.2 | 95.9 | 94.1 |

It was also noted that all of the above formulations remained clear after being exposed at 80° C. for 10 days without any discoloration observed.

Study-4: Gel Formulation Containing 2% Oleic Acid or 10% Oleyl Alcohol, DPG, and PEG400

Gel formulations of Example 17 were subjected to stability study at 80° C. for 10 days. Stability under the condition of at 80° C. for 10 days is expected to be approximately equivalent to the stability for three (3) years at room temperature. A relative purity of Compound 1.002 after being exposed for 5 days and 10 days at 80° C. was determined by HPLC, as compared to its initial purity (at day 0). Table 18 shows stability data of Compound 1.002 in each formulation.

TABLE 18

Results of Stability Study of Compound 1.002 at 80° C.

| Formulation | Oleic acid (%) | Oleyl alcohol (%) | Day 0 | Day 5 | Day 10 |
|---|---|---|---|---|---|
| | | | Relative Purity (%) | | |
| 17A | 2 | — | 100 | 99.4 | 98.6 |
| 17B | — | 10 | 100 | 98.8 | 96.8 |

Gel formulations of Example 17, in which Compound 1.002 was formulated at 80% degree to saturation, were subjected to freeze/thaw study (−20° C./25° C., 24 h/24 h; 3 cycles). Table 19 shows the appearance of Compound 1.002 in each formulation.

TABLE 19

Freeze/thaw study of Compound 1.002 in a Gel Formulation

| Formulation | | mg/mL | 1st cycle | 2nd cycle | 3rd cycle |
|---|---|---|---|---|---|
| 17A | 100% saturation | 105.0 | — | — | — |
| (2% oleic | 85% saturation | 89.3 | no crystals | no crystals | no crystals |
| acid) | 75% saturation | 78.8 | no crystals | no crystals | no crystals |
| 17B | 100% saturation | 130.0 | — | — | — |
| (10% oleyl | 85% saturation | 110.5 | no crystals | no crystals | no crystals |
| alcohol) | 75% saturation | 97.5 | no crystals | no crystals | no crystals |

Example 19: Six-Month Stability Study of Topical Gel Formulations Including Compound 1.002

Unless otherwise indicated, a HPLC method was used to determine the content of Compound 1.002 and impurities; ASTM D 1544 was used as the standard test method for color of gel formulations; a gas chromatographic method was used to determine the content of oleic acid; and Brookfield viscometer was used to measure viscosity (cP) of gel formulations.

A: Stability of Gel Formulations of Compound 1.002 in Glass Containers

Study-1: Gel Formulation Containing 10% Oleic Acid and DPG in HPLC Glass Vials

Topical gel formulations were prepared using excipients as shown in Table 20 according to the procedure of Example 8.

TABLE 20

Topical Gel Formulation of Compound 1.002

| Ingredients | wt/wt % |
|---|---|
| DMSO | 30 |
| Oleyl acid | 10 |
| Transcutol P (2-(2-Ethoxyethoxy)ethanol) | 20 |
| Dipropylene glycol (DPG) | 40 |
| Total weight of the base formulation | 100% |
| Hydroxylpropyl cellulose (HPC) | 2[a] |
| Compound 1.002 | 12.0[a] |

[a] the wt/wt % of HPC or Compound 1.002 is based on the total weight of the base formulation.

The gel formulation in HPLC glass vials was subjected to stability study at 40° C./75% RH for 6 months. A purity of Compound 1.002 on month 0, 1, 3, and 6 month at 40° C./75% RH was determined by HPLC. The detected impurity of Compound 1.002 appears to be the hydrolysis product, as MTPP. Table 21 represents stability data of Compound 1.002 in the topical formulation having 1000 oleic acid.

TABLE 21

Stability Data of Compound 1.002 in Topical Formulations at 40° C./75% RH

| Month | Compound 1.002 mg/mL | MTPP | Other impurity | Viscosity (cP) | Appearance |
|---|---|---|---|---|---|
| | | Relative Purity (%) | | | |
| 0 | 106.6 | 100.0 | 0.0 | 0.0 | 11,800 | Clear, no crystals |
| 1 | 106.0 | 98.4 | 1.2 | 0.4 | 12,600 | Clear, no crystals |
| 3 | 107.0 | 97.5 | 2.5 | 0.0 | 11,780 | Clear, no crystals |
| 6 | 109.1 | 95.1 | 4.9 | 0.0 | 12,760 | Clear, no crystals |

Study-2: Gel Formulation Containing 10% Oleic Alcohol, DPG, and PEG400

Topical gel formulation including 10% oleic alcohol, DPG, and PEG400 was prepared using the excipients as shown in Table 22 according to the procedure of Example 8, except PEG400 was also mixed with other excipients.

TABLE 22

Topical Gel Formulation of Compound 1.002

| Ingredients | wt/wt % 19-2A | wt/wt % 19-2B | wt/wt % 19-2C (Vehicle) |
|---|---|---|---|
| DMSO | 30 | 30 | 30 |
| Oleyl alcohol | 10 | 10 | 10 |
| Transcutol P (2-(2-Ethoxyethoxy)ethanol) | 20 | 20 | 20 |
| Dipropylene glycol (DPG) | 5 | 5 | 5 |
| PEG400 | 35 | 35 | 35 |
| Total weight of the base formulation | 100% | 100% | 100% |
| Hydroxylpropyl cellulose (HPC) | 2[a] | 2[a] | 2[a] |
| Compound 1.002 | 11.8[a] | 2.7[a] | 0 |

[a] the wt/wt % of HPC or Compound 1.002 is based on the total weight of the base formulation.

The gel formulation in glass jars was subjected to stability study at 25° C./60% RH for 6 months. A purity of Compound 1.002 on month 0, 1, 3, and 6 month at 25° C./60% RH was determined by HPLC. The detected impurity of Compound 1.002 appears to be the hydrolysis product, as MTPP. Table 23 represents stability data of Compound 1.002 in the topical formulation having 10% oleic alcohol, 5% DPG, and 35% PEG400.

TABLE 23

Stability Data of Compound 1.002 in Topical Formulations at 25° C./60% RH

Formulation 19-2A

| Month | Compound 1.002 (mg/mL) | Impurity of MTPP (%) | Drug Release at 8 h$^a$ (%) | Viscosity (cP) | Color/Visual | Moisture (%) |
|---|---|---|---|---|---|---|
| 0 | 90.9 | 0.0 | 93.5 | 6980 | 3/no crystals | — |
| 1 | 88.9 | 0.0 | 88.7 | 7220 | 3/no crystals | — |
| 3 | 96.2 | 2.4 | 88.9 | 5880 | 3/no crystals | — |
| 6 | 97.2 | 5.2 | 91.5 | 10560 | 4/no crystals | 2.18 |

Formulation 19-2B

| Month | Compound 1.002 (mg/mL) | Impurity of MTPP (%) | Drug Release at 8 h$^a$ (%) | Viscosity (cP) | Color/Visual | Moisture |
|---|---|---|---|---|---|---|
| 0 | 22.7 | — | 91.9 | 9440 | 1/no crystals | — |
| 1 | 22.3 | 4.4 | 85.7 | 9420 | 1/no crystals | — |
| 3 | 21.2 | 7.6 | 86.8 | 6100 | 2/no crystals | — |
| 6 | 23.7 | 9.3 | 89.1 | 9440 | 2/no crystals | 3.11 |

Formulation 19-2C (Vehicle)

| Month | | | | Viscosity (cP) | Color/Visual | Moisture |
|---|---|---|---|---|---|---|
| 0 | — | — | — | 8020 | 0/no crystals | — |
| 1 | — | — | — | 6820 | 0/no crystals | — |
| 3 | — | — | — | 6200 | 0/no crystals | — |
| 6 | — | — | — | 9040 | 0/no crystals | 0.95 |

$^a$"Drug Release" (also known as drug dissolution) refers to the ability of the drug (Compound 1.002 from the gel formulation) diffusing through a cellulose membrane from the donor compartment to receptor compartment. 99.5% of diffused Compound 1.002 stayed intact.

B: Stability of Gel Formulations of Compound 1.002 in Lablabo Containers

Study-3: Gel Formulation Containing 10% Oleic Alcohol and DPG in Lablabo Amcor Foil 18 mL Containers Topical gel formulation including 10% oleic alcohol and DPG was prepared using the excipients as shown in Table 24 according to the procedure of Example 8.

TABLE 24

Topical Gel Formulation of Compound 1.002

| Ingredients | wt/wt % |
|---|---|
| DMSO | 30 |
| Oleyl alcohol | 10 |
| Transcutol P (2-(2-Ethoxyethoxy)ethanol) | 20 |
| Dipropylene glycol (DPG) | 40 |
| Total weight of the base formulation | 100% |
| Hydroxylpropyl cellulose (HPC) | 2$^a$ |
| Compound 1.002 | 7.2$^a$ |

$^a$the wt/wt % of HPC or Compound 1.002 is based on the total weight of the base formulation.

The gel formulation in Lablabo Amcor Foil 18 mL containers was subjected to stability study at 40° C./75% RH for 6 months. A purity of Compound 1.002 on month 0, 1, 3, 4, 5, and 6 month at 40° C./75% RH was determined by HPLC. The detected impurity of Compound 1.002 appears to be the hydrolysis product, as MTPP. Table 25 represents stability data of Compound 1.002 in the topical formulation having 10% oleic alcohol and 40% DPG.

TABLE 25

Stability Data of Compound 1.002 in Topical Formulations at 40° C./75% RH

| | Compound 1.002 | | MTPP | | |
|---|---|---|---|---|---|
| Month | mg/mL | Relative Purity (%) | | Container weight (g) | Visual Appearance |
| 0 | 65.9 | 100 | 0.0 | 41.37 | no crystals |
| 1 | 66.5 | 98.9 | 1.1 | 41.38 | no crystals |
| 3 | 65.9 | 99.0 | 1.0 | 41.41 | no crystals |
| 4 | 66.5 | 97.0 | 3.0 | 41.41 | no crystals |
| 5 | 67.8 | 97.3 | 2.7 | 41.40 | no crystals |
| 6 | 51.1 | 90.0 | 10.0 | 41.43 | no crystals |

Study-4: Gel Formulation Containing 10% Oleic Alcohol, DPG, and PEG400 in Lablabo Amcor Foil 18 mL Containers Topical gel formulation including 10% oleic alcohol, DPG, and PEG400 was prepared using the excipients as shown in Table 26 according to the procedure of Example 8, except PEG400 was also mixed with other excipients.

TABLE 26

Topical Gel Formulation of Compound 1.002

| Ingredients | wt/wt % 19-4 A | wt/wt % 19-4B (Vehicle) |
|---|---|---|
| DMSO | 30 | 30 |
| Oleyl alcohol | 10 | 10 |
| Transcutol P (2-(2-Ethoxyethoxy)ethanol) | 20 | 20 |
| Dipropylene glycol (DPG) | 5 | 5 |
| PEG400 | 35 | 35 |
| Total weight of the base formulation | 100% | 100% |
| Hydroxylpropyl cellulose (HPC) | 2[a] | 2% |
| Compound 1.002 | 11.8[a] | 0 |

[a] the wt/wt % of HPC or Compound 1.002 is based on the total weight of the base formulation.

The gel formulation in Lablabo Amcor Foil 18 mL containers was subjected to stability study at 40° C./75% RH for 6 months. A purity of Compound 1.002 on month 0, 1, 2, 3, and 6 month at 40° C./75% RH was determined by HPLC. The detected impurity of Compound 1.002 appears to be the hydrolysis product, as MTPP. Table 27 represents stability data of Compound 1.002 in the topical formulation having 10% oleic alcohol, 5% DPG, and 35% PEG400.

TABLE 27

Stability Data of Compound 1.002 in Topical Formulations at 40° C./75% RH

Formulation 19-4A

| Month | Compound 1.002 (mg/mL) | Impurity of MTPP (%) | Viscosity (cP) | Color/Visual | Container Weight (g) 1 | 2 | 3 |
|---|---|---|---|---|---|---|---|
| 0 | 96.1 | 0.0 | 8,580 | 4/no crystals | 41.83 | 43.47 | 43.20 |
| 1 | 98.4 | 0.0 | 9,120 | 3/no crystals | 41.84 | 43.76 | 43.20 |
| 2 | 100.7 | 3.4 | 6,560 | 3/no crystals | 41.83 | 43.77 | 43.20 |
| 3 | 96.3 | 5.5 | 12,360 | 3/no crystals | 41.87 | 43.79 | 43.22 |
| 6 | 101.0 | 11.7 | 10,420 | 3/no crystals | 41.87 | 43.79 | 43.23 |
| 6 | Moisture (%) from 3 dispensers: 0.96, 0.57, and 0.49% | | | | | | |
| 6 | Moisture (%) from 1 glass jar: 2.03% | | | | | | |

Formulation 19-4B (Vehicle)

| Month | — | — | Viscosity (cP) | Color/Visual | Container Weight (g) 1 | 2 | 3 |
|---|---|---|---|---|---|---|---|
| 0 | — | — | 8,780 | 0/no crystals | 44.26 | 43.32 | 43.68 |
| 1 | — | — | 10,500 | 0/no crystals | 44.26 | 43.32 | 43.68 |
| 2 | — | — | 6,900 | 0/no crystals | 44.26 | 43.32 | 43.68 |
| 3 | — | — | 9,860 | 0/no crystals | 44.28 | 43.35 | 43.70 |
| 6 | — | — | 9,040 | 0/no crystals | 44.29 | 43.37 | 43.70 |
| 6 | Moisture (%) from 3 dispensers: 0.73, 1.33, and 0.57% | | | | | | |
| 6 | Moisture (%) from 1 glass jar: 0.95% | | | | | | |

Study-5: Gel Formulation Containing 10% Oleic Alcohol, DPG, and PEG400 in Lablabo Eliopack Foil 33 mL Containers Topical gel formulation including 10% oleic alcohol, DPG, and PEG400 was prepared using the excipients as shown in Table 26 of Study 4 according to the procedure of Example 8, except PEG400 was also mixed with other excipients.

The gel formulation in Lablabo Eliopack Foil 33 mL containers was subjected to stability study at 40° C./75% RH for 6 months. A purity of Compound 1.002 on month 0, 1, 2, 3, and 6 month at 40° C./75% RH was determined by HPLC. The detected impurity of Compound 1.002 appears to be the hydrolysis product, as MTPP. Table 28 represents stability data of Compound 1.002 in the topical formulation having 15 oleic alcohol, 5 DPG, and 35 PEG400.

TABLE 28

Stability Data of Compound 1.002 in Topical Formulations at 40° C./75% RH

Formulation 19-5A

| Month | Compound 1.002 (mg/mL) | Impurity of MTPP (%) | Viscosity (cP) | Visual | Container Weight (g) 1 | 2 | 3 |
|---|---|---|---|---|---|---|---|
| 0 | 108.1 | — | — | no crystals | 62.32 | 61.72 | 61.95 |
| 1 | 107.1 | 0.9 | — | no crystals | 62.35 | 61.75 | 61.98 |
| 2 | 107.8 | 2.5 | — | no crystals | — | — | 61.98 |
| 3 | 106.0 | 5.0 | — | no crystals | — | — | 61.90 |
| 6 | 108.9 | 7.0 | — | no crystals | — | — | 61.76 |
| 6 | Moisture (%) from 3 dispensers: 1.52, 1.19, and 1.64% | | | | | | |

Formulation 19-5B (Vehicle)

| Month | — | — | Viscosity (cP) | Visual | Container Weight (g) 1 | 2 | 3 |
|---|---|---|---|---|---|---|---|
| 0 | — | — | — | no crystals | 60.98 | 61.20 | 61.23 |
| 1 | — | — | — | no crystals | 61.00 | 61.21 | 61.25 |
| 2 | — | — | — | no crystals | 60.99 | 61.21 | 61.25 |
| 3 | — | — | — | no crystals | 61.02 | 61.24 | 61.28 |
| 6 | — | — | — | no crystals | 61.02 | 61.26 | 61.29 |
| 6 | Moisture (%) from 3 dispensers: 1.22, 0.98, and 1.21% | | | | | | |

Study-6: Gel Formulation Containing 10% Oleic Alcohol, DPG, and PEG400 in Lablabo ACS Foil 55 mL Containers Topical gel formulation including 10% oleic alcohol, DPG, and PEG400 was prepared using the excipients as shown in Table 22 of Study 2 according to the procedure of Example 8, except PEG400 was also mixed with other excipients.

The gel formulation in Lablabo ACS Foil 55 mL containers was subjected to stability study at 40° C./75% RH for 6 months. A purity of Compound 1.002 on month 0, 1, 3, and 6 month at 40° C./75% RH was determined by HPLC. The detected impurity of Compound 1.002 appears to be the hydrolysis product, as MTPP. Table 29 represents stability data of Compound 1.002 in the topical formulation having 10% oleic alcohol, 5% DPG, and 35% PEG400.

TABLE 29

Stability Data of Compound 1.002 in Topical Formulations at 40° C./75% RH

Formulation 19-6A

| Month | Compound 1.002 (mg/mL) | Impurity of MTPP (%) | Viscosity (cP) | Color/ Visual | Container Weight (g) 1 | 2 | 3 |
|---|---|---|---|---|---|---|---|
| 0 | 105.5 | — | — | 5/no crystals | 92.24 | 91.85 | 92.41 |
| 1 | 109.9 | 1.3 | — | 5/no crystals | — | 91.85 | 91.24 |
| 3 | 106.0 | 5.1 | — | 5/no crystals | — | 91.89 | 91.30 |
| 6 | 107.0 | 4.7 | — | 5/no crystals | — | 91.94 | 91.37 |
| 6 | | | Moisture (%): 1.54% | | | | |

Formulation 19-6B

| Month | Compound 1.002 (mg/mL) | Impurity of MTPP (%) | Viscosity (cP) | Color/ Visual | Container Weight (g) 1 | 2 | 3 |
|---|---|---|---|---|---|---|---|
| 0 | 52.1 | — | — | 3/no crystals | 90.87 | 91.75 | 91.14 |
| 1 | 51.5 | 5.2 | — | 3/no crystals | — | 91.87 | 91.44 |
| 3 | 51.3 | 5.7 | — | 3/no crystals | — | 91.92 | 91.29 |
| 6 | 51.0 | 10.0 | — | 6/no crystals | — | — | 91.429 |
| 6 | | | Moisture (%): 0.82% | | | | |

TABLE 29-continued

Stability Data of Compound 1.002 in Topical Formulations at 40° C./75% RH

Formulation 19-6C (Vehicle)

| Month | Viscosity (cP) | Color/ Visual | Container Weight (g) 1 | 2 | 3 |
|---|---|---|---|---|---|
| 0 | — | 0/no crystals | 90.99 | 90.62 | 91.16 |
| 1 | — | 0/no crystals | 90.98 | 90.63 | 91.16 |
| 3 | — | 0/no crystals | 91.07 | 90.79 | 91.19 |
| 6 | — | 3/no crystals | 91.18 | 90.45 | 91.24 |
| 6 | Moisture (%): 0.96% | | | | |

Example 20: Stability Study of Compound 1.002

The stability of three lots of Compound 1.002 as Active Pharmaceutical Ingredient (API) was studied for a period of 12 months. Table 30 below shows the HPLC assay results from the stability studies.

TABLE 30

Stability Data of Compound 1.002
Study Conditions/Compound 1.002 Purity by HPLC Area

| Time (Months) | Lot-1 25° C./ 60% RH | Lot-1 40° C./ 75% RH | Lot-2 40° C./ 75% RH | Lot-3 40° C./ 75% RH |
|---|---|---|---|---|
| | Compound 1.002 Purity by a HPLC Assay Method (%) | | | |
| 0 | 99.5 | 99.5 | 99.4 | 100.0 |
| 1 | — | — | 100.0 | 100.0 |
| 2 | — | — | 99.3 | 100.0 |
| 3 | 99.4 | 99.2 | 97.9 | 98.9 |
| 6 | 99.6 | 99.5 | 100.0 | 100.0 |
| 9 | 99.8 | — | — | — |
| 12 | 99.9 | — | — | — |

Example 21: Lipid Kinase Inhibitory Activity

Lipid kinase inhibitory activity of Compounds 1.002 and 1.015 was evaluated as compared to their corresponding parent compounds, namely 3-(4-morpholinothieno(3,2-d)pyrimidin-2-yl)phenol (MTPP) and (3-(4-morpholinothieno[3,2-d]pyrimidin-2-yl)phenyl)methanol (abbreviated as MTPPM).

Lipid kinases: Lipid kinases from Reaction Biology Corporation (RBC) in ADP-Glo format were used.

Assay Description: The kinase reactions utilized ATP and produced ADP as a byproduct. The ADP production was quantified by ADP-Glo luminescence detection. This assay was a 3-step reaction. First, the kinase reaction with lipid substrate was carried out in the presence of ATP, and the reaction was quenched and depleted remaining ATP with ADP-Glo™ reagent, and then finally ADP was converted to ATP which was measured using a luciferase/luciferin reaction.

Assay Procedure: The assay was performed according to the steps as follows:
1. Preparing substrate in freshly prepared reaction buffer;
2. Delivering kinase into the substrate solution and gently mixing;
3. Delivering compounds in 100% DMSO into the kinase reaction mixture by Acoustic technology (Echo550; nanoliter range), incubating for 20 minutes at room temperature;
4. Delivering ATP into the reaction mixture to initiate the reaction;
5. Incubating for 30 minutes at 30° C.;
6. Quenching the reaction with ADP-Glo reagent and incubating for 40 minutes;
7. Adding Detection Mixture and incubating for 30 minutes; and
8. Measuring luminescence.

Data Analysis: The luminescence was converted into μM ADP production based on ADP standard curves. The non-linear regression to obtain the standard curve and $IC_{50}$ values were performed using Graphpad Prism software.

Table 31 lists $IC_{50}$ values of Compounds 1.002 and 1.015 as compared to their corresponding parent compounds MTPP and MTPPM, respectively.

TABLE 31

PI3K Activity of Compounds 1.002 and 1.015

| | Kinase | $IC_{50}$ (nM) 1.002 | MTPP[a] | 1.015 | MTPPM[b] |
|---|---|---|---|---|---|
| α | PI3Ka (p110a/p85a) | 35 | 5.2 | 1928 | 7.0 |
| β | PI3Kb (p110b/p85a) | 257 | 38 | 5594 | 56 |
| γ | PI3Kg (p110g) | 544 | 90 | 131 | 61 |
| δ | PI3Kd (p110d/p85a) | 83 | 19 | 714 | 17 |
| α E542K | PI3K (p110a(E542K)/p85a) | 42 | 5.6 | 3686 | 9.0 |
| α E545K | PI3K (p110a(E545K)/p85a) | 49 | 6.3 | 4314 | 9.8 |
| α H1047R | PI3K (p110a(H1047R)/p85a) | 59 | 7.2 | 3111 | 7.8 |
| mTOR | MTOR/FRAP1 | 1415 | 218 | 3325 | 113 |

[a]MTPP stands for 3-(4-morpholinothieno(3,2-d)pyrimidin-2-yl)phenol; and
[b]MTPPM stands for (3-(4-morpholinothieno[3,2-d]pyrimrdin-2-yl)phenyl)methanol.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having formula (I):

(I)

or a hydrate, solvate, and/or a pharmaceutically acceptable salt thereof,
wherein:
subscript m is an integer from 0 to 2; and
i) $L^1$ is —C(O)—, —C(O)O—, —C(O)S—, or —C(O)NH—; and
$R^1$ is $C_{1-6}$ alkyl, $C_{1-6}$ hydroxyalkyl, $C_{1-6}$ haloalkyl, $C_{2-6}$ alkenyl, $C_{6-10}$ aryl, $C_{6-10}$ aryl-$C_{1-6}$ alkyl, or $C_{6-10}$ aryl-$C_{2-6}$ alkenyl;
ii) $L^1$-$R^1$ has the formula:

wherein
the wavy line indicates the attachment to the adjacent oxygen atom in formula (I);
subscript t is an integer from 0 to 1;
subscripts p and q are independently an integer from 0 to 2;
$R^3$ is hydrogen or a sidechain of a natural or unnatural amino acid and $R^4$ is hydrogen, or $R^3$ and $R^4$ are combined to be a sidechain of a cyclic amino acid;
$R^5$ is hydrogen or a sidechain of a natural or unnatural amino acid and $R^6$ is hydrogen, $C_{1-6}$ alkyl, or $C_{2-6}$ alkenyl, or $R^5$ and $R^6$ are combined to be a sidechain of a cyclic amino acid; and
$R^7$ is hydrogen, $C_{1-6}$ alkyl, $C_{2-6}$ alkenyl, $C_{1-6}$ alkyl-C(O)—, or $C_{2-6}$ alkenyl-C(O)—, or
$R^5$ is hydrogen or a sidechain of a natural or unnatural amino acid; and
$R^6$ and $R^7$ are combined to form a 3-6 membered heterocycle, optionally having an additional 1-2 heteroatoms selected from O, S, and N as ring vertices; or
iii) $L^1$ is —C(O)—; and
$R^1$ is an aliphatic chain of a saturated fatty acid having 8-18 carbon atoms or an unsaturated fatty acid having 10-18 carbon atoms.

2. The compound of claim 1, wherein subscript m is 0 or 1.

3. The compound of claim 1, having formula (II) or (III):

(II)

or (III)

4. The compound of claim 1, having formula (IIa):

(IIa)

5. The compound of claim 4, wherein $R^1$ is $C_{1-6}$ alkyl.

6. The compound of claim 4, wherein $R^1$ is methyl or ethyl.

7. The compound of claim 1, having the formula (IIb)

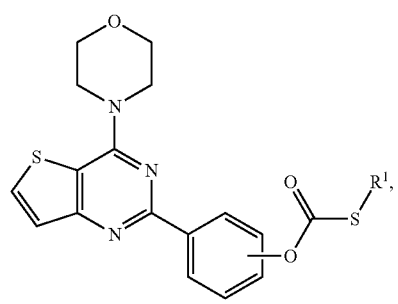
(IIc)

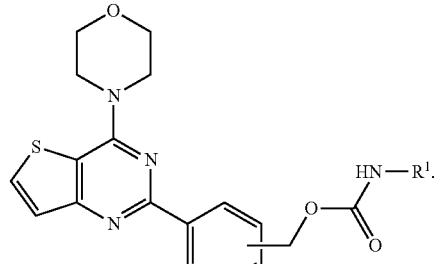
(IIId)

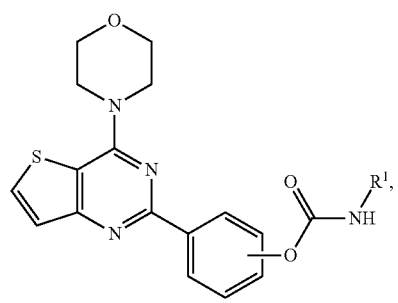
(IId)

8. The compound of claim 7, wherein $R^1$ is $C_{1-6}$ alkyl.

9. The compound of claim 7, wherein $R^1$ is methyl or ethyl.

10. The compound of claim 1, wherein $R^1$ is methyl or ethyl.

11. The compound of claim 1, wherein $R^1$ is phenyl-CH=CH—.

12. The compound of claim 1, wherein subscripts p and q are each 0.

13. The compound of claim 12, having formula (IIa-1) or (IIIa-1):

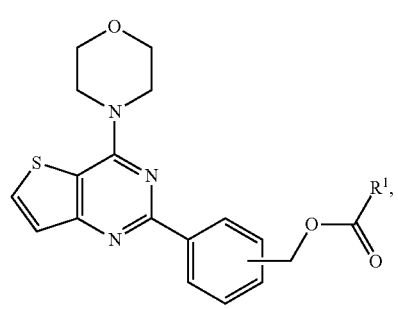
(IIIa)

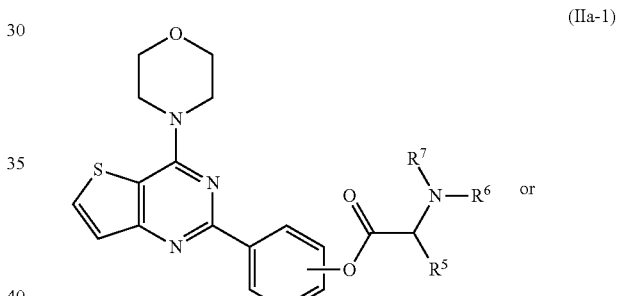
(IIa-1)

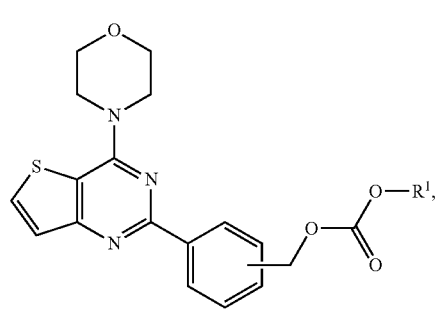
(IIIb)

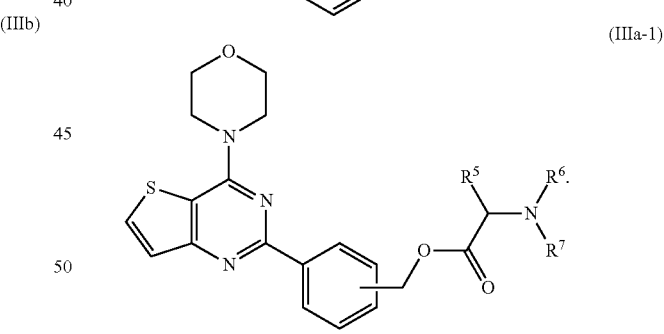
(IIIa-1)

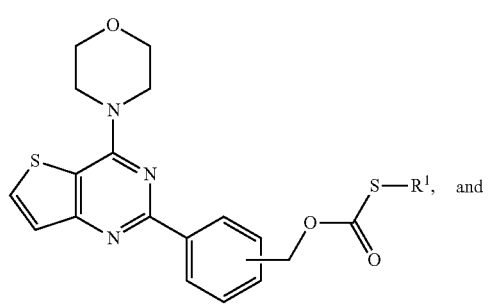
(IIIc)

14. The compound of claim 1, wherein the saturated fatty acid having 8-18 carbon atoms is selected from the group consisting of caprylic acid, pelargonic acid, capric acid, neodecanoic acid, undecylic acid, lauric acid, tridecylic acid, myristic acid, pentadecylic acid, palmitic acid, margaric acid, stearic acid, and isostearic acid.

15. The compound of claim 1, wherein the unsaturated fatty acid having 10-18 carbon atoms is selected from the group consisting of caproleic acid, lauroleic acid, myristoleic acid, palmitoleic acid, sapienic acid, oleic acid, elaidic acid, vaccenic acid, linoleic acid, alpha-linolenic acid, gamma-linolenic acid, columbinic acid, pinolenic acid, and stearidonic acid.

16. The compound of claim 1, selected from the group consisting of:
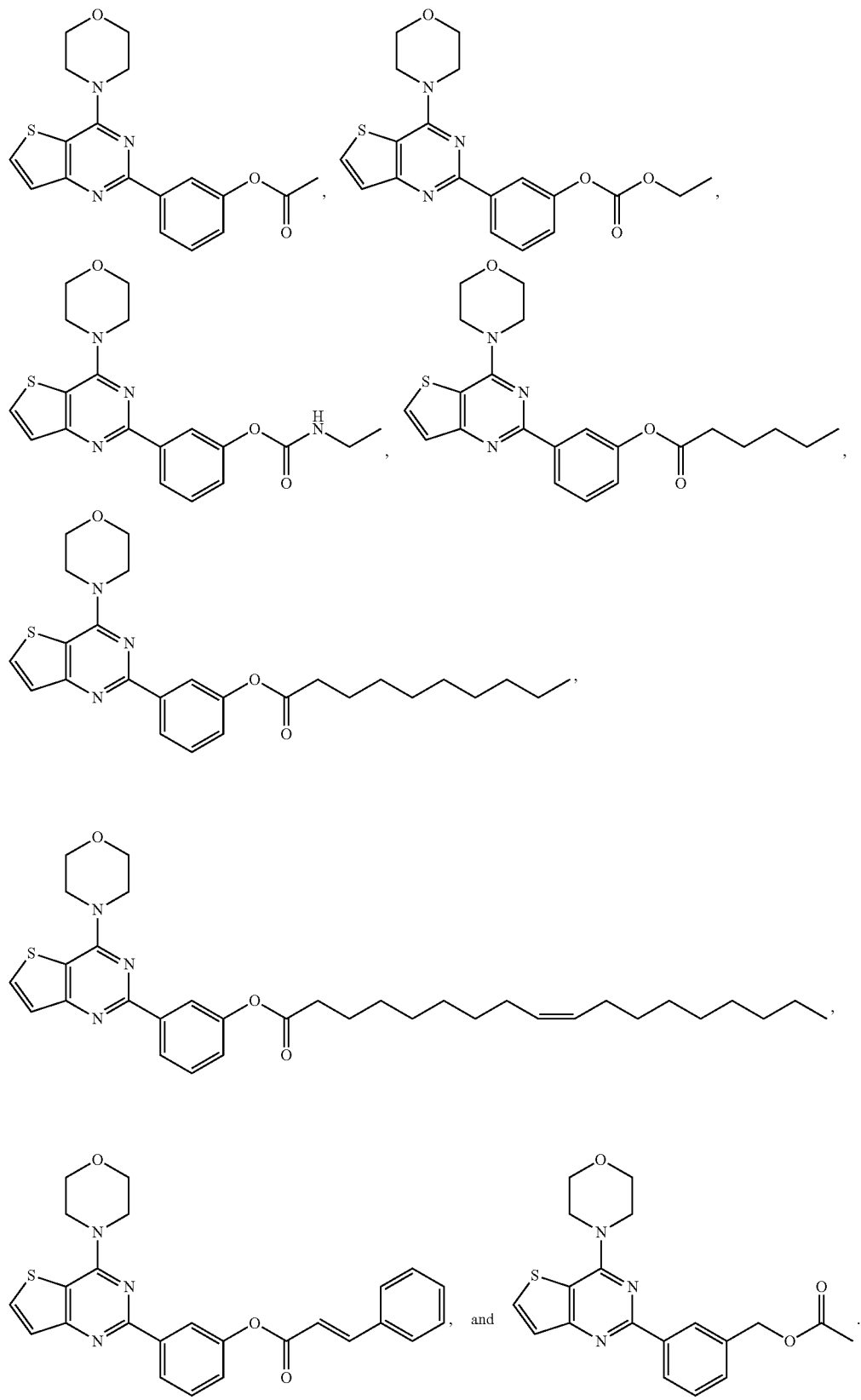

17. The compound of claim 1, represented by the formula:

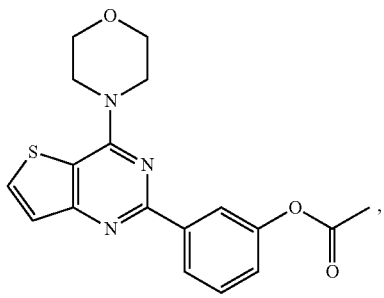 [SMILES: CC(=O)Oc1cccc(-c2nc(N3CCOCC3)c3sccc3n2)c1]

or a pharmaceutically acceptable salt thereof.

18. The compound of claim 1, represented by the formula:

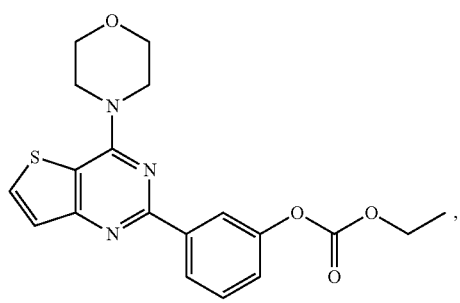 [SMILES: CCOC(=O)Oc1cccc(-c2nc(N3CCOCC3)c3sccc3n2)c1]

or a pharmaceutically acceptable salt thereof.

19. The compound of claim 1, represented by the formula:

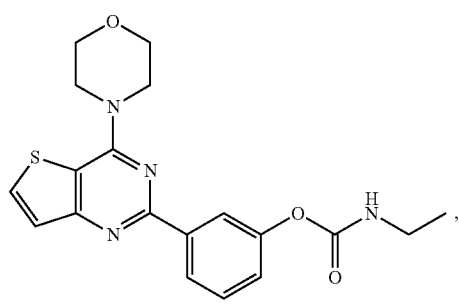 [SMILES: CCNC(=O)Oc1cccc(-c2nc(N3CCOCC3)c3sccc3n2)c1]

or a pharmaceutically acceptable salt thereof.

20. The compound of claim 1, represented by the formula:

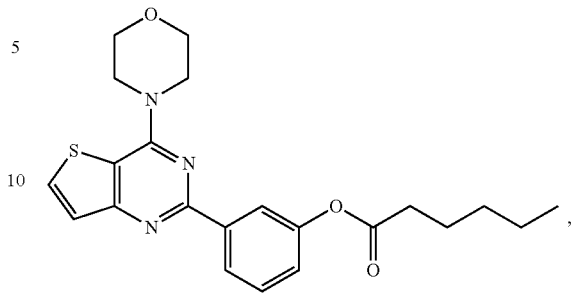

or a pharmaceutically acceptable salt thereof.

21. The compound of claim 1, represented by the formula:

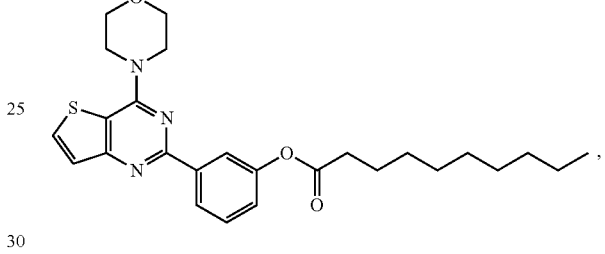

or a pharmaceutically acceptable salt thereof.

22. The compound of claim 1, represented by the formula:

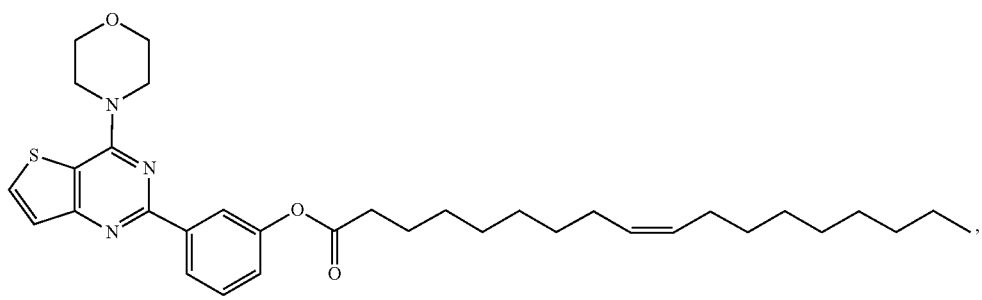 [SMILES: CCCCCCCC/C=C\CCCCCCCC(=O)Oc1cccc(-c2nc(N3CCOCC3)c3sccc3n2)c1]

or a pharmaceutically acceptable salt thereof.

23. The compound of claim 1, represented by the formula:

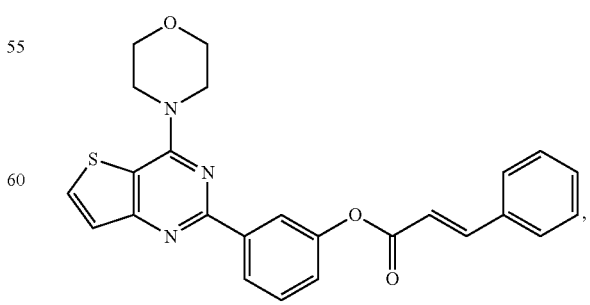

or a pharmaceutically acceptable salt thereof.

24. The compound of claim 1, represented by the formula:
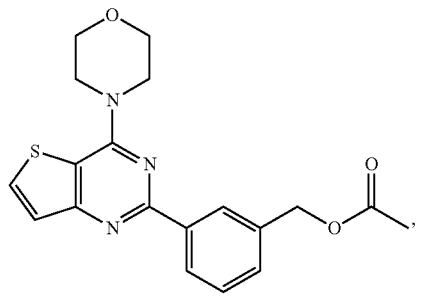
or a pharmaceutically acceptable salt thereof.
* * * * *